(12) United States Patent
Komirishetty et al.

(10) Patent No.: US 11,739,082 B2
(45) Date of Patent: Aug. 29, 2023

(54) THIOPHENE COMPOUNDS, PROCESS FOR SYNTHESIS AND USE THEREOF

(71) Applicant: AHAMMUNE BIOSCIENCES PRIVATE LIMITED, Pune (IN)

(72) Inventors: Kashinath Komirishetty, Pune (IN); Mahesh Kumar Verma, Pune (IN); Parul Ganju, Pune (IN); Sudhanand Prasad, Pune (IN)

(73) Assignee: Ahammune Biosciences Private Limited, Pune (IN)

( * ) Notice: Subject to any disclaimer, the term of this patent is extended or adjusted under 35 U.S.C. 154(b) by 0 days.

(21) Appl. No.: 16/643,409

(22) PCT Filed: Aug. 31, 2018

(86) PCT No.: PCT/IB2018/056677
§ 371 (c)(1),
(2) Date: Feb. 28, 2020

(87) PCT Pub. No.: WO2019/043642
PCT Pub. Date: Mar. 7, 2019

(65) Prior Publication Data
US 2020/0255417 A1    Aug. 13, 2020

(30) Foreign Application Priority Data
Aug. 31, 2017  (IN) .............................. 201721030816

(51) Int. Cl.
| | |
|---|---|
| C07D 413/14 | (2006.01) |
| C07D 413/06 | (2006.01) |
| C07D 413/12 | (2006.01) |
| C07D 417/12 | (2006.01) |
| C07D 409/12 | (2006.01) |
| C07D 409/06 | (2006.01) |
| C07D 333/24 | (2006.01) |
| A61P 17/00 | (2006.01) |

(52) U.S. Cl.
CPC ........... *C07D 413/14* (2013.01); *A61P 17/00* (2018.01); *C07D 333/24* (2013.01); *C07D 409/06* (2013.01); *C07D 409/12* (2013.01); *C07D 413/06* (2013.01); *C07D 413/12* (2013.01); *C07D 417/12* (2013.01)

(58) Field of Classification Search
CPC .. C07D 413/14; C07D 413/06; C07D 413/12; C07D 333/24; C07D 409/06; C07D 409/12; C07D 417/12
See application file for complete search history.

(56) References Cited

U.S. PATENT DOCUMENTS

| | | | |
|---|---|---|---|
| 3,691,202 A | 9/1972 | O'Mant | |
| 4,432,992 A * | 2/1984 | Cragoe, Jr. .......... | C07D 333/22 514/422 |
| 8,461,207 B2 | 6/2013 | Aydt et al. | |
| 2004/0192943 A1 | 9/2004 | Wan et al. | |
| 2005/0101641 A1* | 5/2005 | Freskos .................. | A61P 29/00 514/355 |
| 2005/0119332 A1 | 6/2005 | Jeppesen et al. | |
| 2006/0199845 A1 | 9/2006 | Sun et al. | |
| 2007/0167499 A1 | 7/2007 | Stunkel et al. | |
| 2008/0027048 A1 | 1/2008 | Miyata et al. | |
| 2009/0030015 A1 | 1/2009 | Kranich et al. | |
| 2015/0197530 A1 | 7/2015 | Lepifre et al. | |

FOREIGN PATENT DOCUMENTS

| | | | |
|---|---|---|---|
| DE | 19 19 381 A1 | 4/1969 | |
| GB | 1226981 | * | 3/1971 |
| WO | WO-94/136665 A1 | 6/1994 | |
| WO | WO 2003/101978 A1 | 12/2003 | |
| WO | WO-2006/081389 A1 | 8/2006 | |

OTHER PUBLICATIONS

International Search Report and Written Opinion issued in PCT Application No. PCT/182018/056677, dated Dec. 27, 2018, 11 pages.

* cited by examiner

*Primary Examiner* — Rebecca L Anderson
(74) *Attorney, Agent, or Firm* — Foley & Lardner LLP

(57) ABSTRACT

The present invention relates to novel thiophene compounds of general Formula I, and their stereoisomers (diastereoisomers, enantiomers), pure or mixed, racemic mixtures, geometrical isomers, tautomers, pharmaceutically acceptable salts, hydrates, solvates, solid forms and mixtures thereof along with process for their preparation. The present invention discloses compounds that are useful in the treatment and prevention of autoimmune diseases.

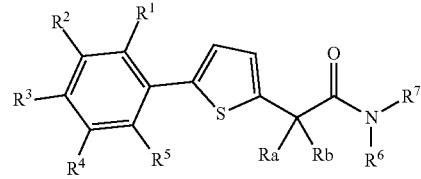

Formula I

13 Claims, No Drawings

THIOPHENE COMPOUNDS, PROCESS FOR SYNTHESIS AND USE THEREOF

CROSS-REFERENCE TO RELATED APPLICATIONS

This application is the U.S. national stage entry application of International Patent Application No. PCT/IB2018/056677, filed Aug. 31, 2018, which claims priority to and the benefit of Indian Patent Application No. 201721030816, filed Aug. 31, 2017.

FIELD OF THE INVENTION

The present invention relates to novel thiophene compounds of general Formula 1 and the process for the preparation thereof. The present invention discloses compounds that are useful in the treatment and prevention of cellular stress-mediated diseases involving systemic and/or organ-specific immunity.

BACKGROUND OF THE INVENTION

The immune system is a collection of special cells and chemicals that fight infection-causing agents such as bacteria and viruses. An autoimmune disorder occurs when a person's immune system mistakenly attacks their own body cells and tissues. Autoimmune disorders are broadly grouped into two categories—'organ-specific' meaning only one organ is affected, while in 'systemic' disorders, multiple organs or body systems may be affected.

There are a large number of autoimmune disorders ranging in severity from mild to disabling, depending on which system of the body is under attack and to what degree. It has also been observed that, women are more susceptible than men, particularly during their childbearing years. It is thought that sex hormones may be at least partly responsible.

Autoimmune diseases are characterized by an abnormal immune response involving either cells or antibodies, that are in either case directed against normal autologous tissues. Both adaptive immune response, comprising T-cell mediated immunity and humoral immune response, involving antibody-mediated immunity is involved in the trigger and spread of autoimmune diseases.

The triggers of autoimmunity are not well understood. Till recent years, studies on etiopathogenesis of autoimmune diseases have focused on the role of immune components. However, several studies have now highlighted the synergistic role of target tissues in spread of autoimmunity. A common pathway that has emerged in these studies is endoplasmic reticulum stress (ER stress). ER is a major cellular organelle that is associated with critical functions involving cellular homeostasis including protein synthesis, folding and quality control, antigen processing and presentation, calcium control and redox balance. The physiological activity of the ER is tightly controlled by cell intrinsic as well as extrinsic processes. Disturbance in the functioning of ER triggers a stress response called ER stress that activates intracellular signaling pathways, constituting the unfolded protein response (UPR) targeted to manage stress conditions. However, inability to manage ER stress is implicated in a number of pathological conditions including cancers, metabolic, dermatological, cardiovascular and neurodegenerative diseases. In addition, aberrant regulation of ER stress is associated with early autoimmune events. For instance, misfolding of proteins and alteration in antigen processing can lead to immunogenic neoantigen formation. Further, stressed cells could be inadequate to support tolerance mechanisms in autoreactive cells, which are less susceptible to programmed cell death, perpetuating autoimmunity in diseases including type I diabetes, rheumatoid arthritis, psoriatic arthritis, multiple sclerosis, lupus, celiac disease, pernicious anaemia. ER stress mechanisms attain special interest in the physiology of skin, an organ that is constantly exposed to the external environment. In fact, deregulation of ER stress mechanisms are associated with several skin autoimmune diseases, including Vitiligo, psoriasis, SLE, pemphigus, scleroderma. Targeting ER stress mechanisms thus represents a potential therapeutic approach for autoimmune diseases.

It has been observed that most of the existing therapies for autoimmune disorders aim to provide only symptomatic benefit to patients as there is little by way of targeted and effective therapy. Administration of steroids is one of the most common approach for treatment. However, the non-specific nature and side-effects associated with long-term steroid usage limits their usefulness. As an example, Vitiligo is an autoimmune disease where dysregulation of immune functions takes place with increased levels of inflammatory cytokines in the lesion. Hence, topical corticosteroids become the most common first line therapy. Patients are also advised to expose themselves to sunlight in order to increase the melanin synthesis. Phototherapy (narrowband UVB or 311 nm laser) is generally included with topical steroids to achieve better results. However, a number of patients don't achieve the desired level of pigmentation which adds to their psychological burden. At times, dermatologists are unable to tell the possible success of the therapy being administered, hence patients remain uncertain about the duration and outcome of treatment. Clearly, new therapies targeting relevant pathways involved in triggering autoimmune responses are need of the hour.

The embodiments of the present invention provide for chemical entities that modulate cellular stress. More specifically, the chemical entities rescue cells from stress mediated death and thus impede cascade of events leading to aberrant regulation of immunity. These chemical entities thus offer potential for prevention and treatment of immune-related disorders and diseases.

SUMMARY OF THE INVENTION

The compounds of the present invention have the general Formula I:

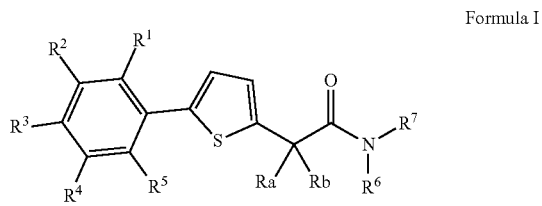

Formula I wherein
$R^1$, $R^2$, $R^3$, $R^4$, $R^5$ are each independently selected from hydrogen, halogen and, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, $C_3$-$C_7$ aromatic or aliphatic heterocycle comprising at least one hetero atom selected from a group of O, N and S;

any of two adjacent R groups form a 5-6 membered aromatic or aliphatic ring comprising at least one hetero atom selected from a group of O, N and S;

Ra and Rb are each independently selected from hydrogen, alkyl, aralkyl, alkenyl, alkynyl, or both Ra, Rb together form a 3-7 membered ring comprising at least one hetero atom selected from a group of O, N and S;

$R^6$ and $R^7$ are each independently selected from hydrogen, straight chain or branched C1-C5 alkyl, straight chain or branched C1-C5 aralkyl, straight chain or branched C2-C5 alkenyl, straight chain or branched C2-C5 alkynyl, together form a 3-7 membered aromatic or aliphatic heterocycle comprising at least one hetero atom selected from O, N, and S, —CH$_2$(CH$_2$)$_n$NR$_c$R$_d$ wherein n is 0-3, and R$_c$, and R$_d$ are both independently selected from C1-C5 alkyl or together form a 3-7 membered aromatic or aliphatic heterocycle comprising at least one hetero atom selected from a group of O, N and S; and their stereoisomers (diastereoisomers, enantiomers), pure or mixed, racemic mixtures, geometrical isomers, tautomers, pharmaceutically acceptable salts, hydrates, solvates, solid forms and mixtures thereof.

The pharmaceutically acceptable salts of the compounds of present invention is selected from a group consisting of hydrochloric acid, hydrobromic acid, nitric acid, sulfuric acid, phosphoric acid, benzenesulfonic acid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid succinic acid, or salts of sodium, potassium, calcium, magnesium and ammonium as an active ingredient, with one or more pharmaceutically acceptable carriers, diluents or excipients.

The present invention also relates to the process of preparation of the compounds having general Formula I:

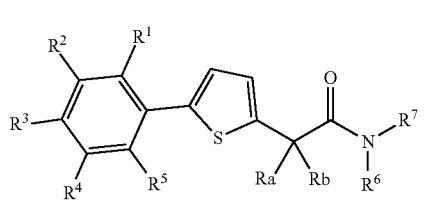

Formula I wherein
$R^1$, $R^2$, $R^3$, $R^4$, $R^5$ are each independently selected from hydrogen, halogen and, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, $C_3$-$C_7$ aromatic or aliphatic heterocycle comprising at least one hetero atom selected from a group of O, N and S;

any of two adjacent R groups form a 5-6 membered aromatic or aliphatic ring comprising at least one hetero atom selected from a group of O, N and S;

Ra and Rb are each independently selected from hydrogen, alkyl, aralkyl, alkenyl, alkynyl, or both Ra, Rb together form a 3-7 membered ring comprising at least one hetero atom selected from a group of O, N and S;

$R^6$ and $R^7$ are each independently selected from Hydrogen, straight chain or branched C1-C5 alkyl, straight chain or branched C1-C5 aralkyl, straight chain or branched C2-C5 alkenyl, straight chain or branched C2-C5 alkynyl, $R^6$ and $R^7$ together form a 3-7 membered aromatic or aliphatic heterocycle comprising at least one hetero atom selected from O, N, S, —CH$_2$(CH$_2$)$_n$NR$_c$R$_d$ wherein n is 0-3, and R$_c$, and R$_d$ are both independently selected from C1-C5 alkyl or together form a 3-7 membered aromatic or aliphatic heterocycle comprising at least one hetero atom selected from a group of O, N and S;

and their stereoisomers (diastereoisomers, enantiomers), pure or mixed, racemic mixtures, geometrical isomers, tautomers, pharmaceutically acceptable salts, hydrates, solvates, solid forms and mixtures thereof.

The process for preparation of the compounds of Formula I comprise the following steps:

a) Stirring thiophene acetonitrile in the presence of catalyst N-bromosuccinamide (NBS) in dimethylformamide (DMF) or solvents selected from dimethylsulfoxide (DMSO) Tetrahydrofuran (THF);

b) Reacting the resultant bromo thiophene acetonitrile obtained from Step a, with substituted phenylboronic acid in the presence of a solvent selected from a group comprising toluene, benzene, dimethyl formamide, dioxane, tertiary butanol, potassium carbonate and triphenylphosphine palladium(0) or any Palladium (0) catalyst at a temperature of about 80° C.-100° C. for about 6-24 hours to obtain compound of Formula II:

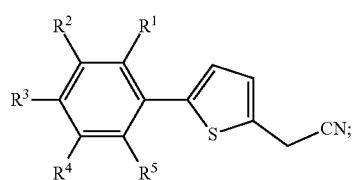

II c) Refluxing the compound of Formula II after stirring it in ethanol and aqueous sodium hydroxide to obtain the compound of Formula III:

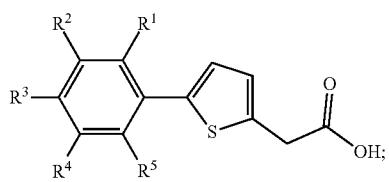

III d) Coupling of compound of Formula III with amines, in the presence of a base selected from Hunigs base (N,N, Diisopropylethylamine), triethylamine, pyrrolidine, piperidine and amide coupling reagent selected from HATU, HBTU, EDC, EDC-HOBt, EDC-DMAP, DCC, DCC-DMAP, DCC-HOBt, DIC, TBTU, T3P added at 0° C. to obtain Formula I:

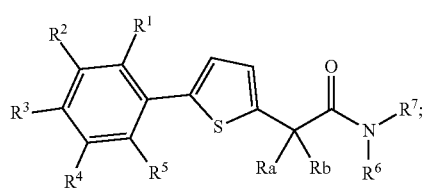

Formula I and
e) Optionally purifying the compound by column chromatography.

DETAILED DESCRIPTION

The compounds of the present invention have the general Formula I:

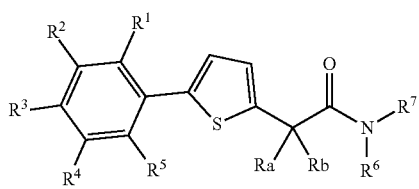

Formula I wherein
R1, R2, R3, R4, R5 are each independently selected from hydrogen, halogen, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, C3-C7 aromatic or aliphatic heterocycle comprising at least one hetero atom selected from a group of O, N and S;
any of two adjacent R groups form a 5-6 membered aromatic or aliphatic ring comprising at least one hetero atom selected from a group of O, N and S;
Ra and Rb are each independently selected from hydrogen, straight chain or branched C1-C5 alkyl, straight chain or branched C1-C5 aralkyl, straight chain or branched C2-C5 alkenyl, straight chain or branched C2-C5 alkynyl, or both Ra, and Rb together form a 3-7 membered ring comprising at least one hetero atom selected from a group of O, N and S;
R6 and R7 are each independently selected from hydrogen, straight chain or branched C1-C5 alkyl, straight chain or branched C1-C5 aralkyl, straight chain or branched C2-C5 alkenyl, straight chain or branched C2-C5 alkynyl;
—CH2(CH2)nNRcRd wherein n is 0-3, and Rc, Rd are both independently selected from straight chain or branched C1-C5 alkyl or together form a 3-7 membered aromatic or aliphatic heterocycle comprising at least one hetero atom selected from a group of O, N and S; or
both R6 and R7 may together form a 3-7 membered aromatic or aliphatic heterocycle comprising at least one hetero atom selected from O, N and S;
and their stereoisomers (diastereoisomers, enantiomers), pure or mixed, racemic mixtures, geometrical isomers, tautomers, pharmaceutically acceptable salts, hydrates, solvates, solid forms and mixtures thereof.

The pharmaceutically acceptable salts of the compounds of the present invention is selected from a group consisting of hydrochloric acid, hydrobromic acid, nitric acid, sulfuric acid, phosphoric acid, benzenesulfonic acid, methanesulfonic acid, ethanesulfonic acid, toluenesulfonic acid, formamidinesulfonic acid, naphthalenedisulfonic acid, formic acid, fumaric acid, acetic acid, propionic acid, lactic acid, malic acid, citric acid, maleic acid, benzoic acid, malonic acid, tartaric acid, oxalic acid succinic acid, or salts of sodium, potassium, calcium, magnesium and ammonium as an active ingredient, with one or more pharmaceutically acceptable carriers, diluents or excipients.

In the context of this invention, the term "alkyl" designates a hydrocarbon radical that is saturated, linear, branched, or cyclic, halogenated or not, having particularly from 1 to 5 carbon atoms. Such as methyl, trifluoromethyl, ethyl, n-propyl, isopropyl, n-butyl, isobutyl, tertbutyl, sec-butyl, pentyl.

The term "alkenyl" refers to a hydrocarbon radical that is unsaturated having one or more carbon-carbon double bond, linear, branched, halogenated, or cyclic having particularly from 2 to 5 carbon atoms.

The term "alkynyl" refers to a hydrocarbon radical that is unsaturated having one or more carbon-carbon triple bond, linear, branched, halogenated, or cyclic having particularly from 2 to 5 carbon atoms.

The term "alkoxyalkyl" refers to an alkyl chain linked to an oxygen atom forming an ether bond. The alkyl chain corresponds to the previously expressed definition and includes alkyl groups such as methoxy, trifluoromethoxy, ethoxy, n-propyloxy, isopropyloxy, n-butoxy, iso-butoxy, tertio-butoxy, sec-butoxy.

The term "aralkyl" refers to aryl-substituted alkyl hydrocarbon radical where the hydrocarbon radical comprises about 1-5 carbon atoms.

The term "cycloalkyl" designates an alkyl group as defined above and forms at least one cycle (e.g. cycloalkyl groups having 3 to 8 carbon atoms: cyclopropyl, cyclobutyl, cyclopentyl, cyclohexyl, cycloheptyl, and cyclooctyl).

The term "aryl" refers to aromatic groups comprising preferably from 6-10 carbon atoms, possibly interrupted by one or several heteroatoms selected among N, O, or S (more specifically call "heteroaryl"). They are generally mono- or bi-cyclical and comprise preferably from 6 to 14 carbon atoms, such as phenyl, α-naphtyl, β-naphtyl.

The term "alkoxyaryl" refers to an alkyl group having bonded to an oxygen atom to form an ether bond attached to an aryl group.

The term "heterocycle" refers to any a cycloalkyl group as defined above interrupted by one or more heteroatoms chosen among O, N and S being aliphatic or aromatic rings being preferably 3-7 membered rings.

The term "halogen" refers to an atom of fluorine, chlorine, bromine or iodine.

The term "effective amount", "pharmaceutically effective amount" or "therapeutically effective amount" refers to any amount which will cause an improvement or change in the condition for which it is applied. The amount is sufficient to prevent or treat a disorder, disease or condition or one or more of its symptoms and/or to prevent the occurrence of the disease or disorder and can be determined by standard clinical techniques. The amount may vary with the condition being treated, the stage of advancement of the condition, the body surface area affected with the clinical condition, and the type and concentration of formulation administered.

The acronym "HATU" refers to 1-[Bis(dimethylamino)methylene]-1H-1,2,3-triazolo[4,5-b]pyridinium 3-oxid hexafluorophosphate, Hexafluorophosphate Azabenzotriazole Tetramethyl Uronium; the acronym "HBTU" refers to 2-(1H-benzotriazol-1-yl)-1,1,3,3-tetramethyluronium hexafluorophosphate, Hexafluorophosphate Benzotriazole Tetramethyl Uronium; the acronym "EDC" refers to 1-Ethyl-3-(3-dimethylaminopropyl)carbodiimide; the acronym "EDC-HOBt" refers to 1-Ethyl-3-(3-dimethylaminopropyl)carbodiimide-Hydroxybenzotriazole; the acronym "EDC-DMAP" refers to 1-Ethyl-3-(3-dimethylaminopropyl)carbodiimide-Dimethylaminopyridine; the acronym "DCC" refers to N,N'-Dicyclohexylcarbodiimide; the acronym "DCC-DMAP" refers to N,N'-Dicyclohexylcarbodiimide-4-Dimethylaminopyridine; the acronym "DCC-HOBt" refers to N,N'-Dicyclohexylcarbodiimide-Hydroxybenzotriazole; the acronym "DIC" refers to N,N'-Diisopropylcarbodiimide; the acronym "TBTU" refers to 2-(1H-Benzotriazole-1-yl)-1,1,3,3-tetramethylaminium tetrafluoroborate; the acronym "T3P" refers to Propylphosphonic Anhydride; the acronym "NBS" refers to N-bromosuccinamide; the acronym "DMF" refers to dimethylformamide; the acronym "DMSO" refers to dimethyl sulfoxide; the acronym "THF" refers to Tetrahyydrofuran; the acronym "DIPEA" refers to N,N-Diisopropylethylamine also known as Hunig's base.

The present invention further discloses process the preparation of the compounds of general Formula I:

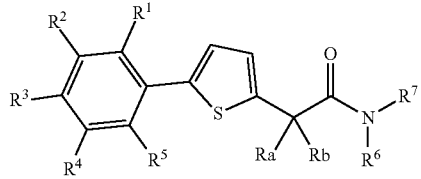

Formula I wherein $R^1$, $R^2$, $R^3$, $R^4$, $R^5$ are each independently selected from hydrogen, halogen and, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, $C_3$-$C_7$ aromatic or aliphatic heterocycle comprising at least one hetero atom selected from a group of O, N and S;

any of two adjacent R groups can form a 5-6 membered aromatic or aliphatic ring comprising at least one hetero atom selected from a group of O, N and S;

Ra and Rb are each independently selected from hydrogen, alkyl, aralkyl, alkenyl, alkynyl, or both Ra, Rb together form a 3-7 membered ring comprising at least one hetero atom selected from a group of O, N and S;

$R^6$ and $R^7$ are each independently selected from Hydrogen, straight chain or branched C1-C5 alkyl, straight chain or branched C1-C5 aralkyl, straight chain or branched C2-C5 alkenyl, straight chain or branched C2-C5 alkynyl, $R^6$ and $R^7$ together form a 3-7 membered aromatic or aliphatic heterocycle comprising at least one hetero atom selected from O, N, S, —$CH_2(CH_2)_nNR_cR_d$ wherein n is 0-3, and $R_c$, and $R_d$ are both independently selected from C1-C5 alkyl or together form a 3-7 membered aromatic or aliphatic heterocycle comprising at least one hetero atom selected from a group of O, N and S;

And their stereoisomers (diastereoisomers, enantiomers), pure or mixed, racemic mixtures, geometrical isomers, tautomers, pharmaceutically acceptable salts, hydrates, solvates, solid forms and mixtures thereof.

A process for preparation of the compounds of Formula I, comprising the steps of a) Stirring thiophene acetonitrile in the presence of catalyst N-bromosuccinamide (NBS) in dimethylformamide (DMF) or solvents selected from dimethylsulfoide (DMSO) Tetrrahydrofuran (THF);

b) Reacting the resultant bromo thiophene acetonitrile obtained from Step a, with substituted phenylboronic acid in the presence of solvent selected from a group comprising toluene, benzene, dimethyl formamide, dioxane, tertiary butanol, potassium carbonate and triphenylphosphine palladium(0) or any Palladium (0) catalyst at a temperature of about 80° C.-100° C. for about 6-24 hours to obtain compound of Formula II:

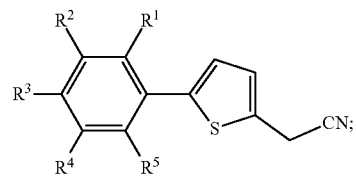

II c) Refluxing the compound of Formula II after stirring it in ethanol and aqueous sodium hydroxide to obtain the compound of Formula III:

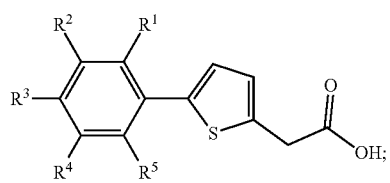

III d) Coupling of compound of Formula III with amines, in the presence of a base selected from Hunigs base (N,N, Diisopropylethylamine), triethylamine, pyrrolidine, piperidine and amide coupling reagent selected from HATU, HBTU, EDC, EDC-HOBt, EDC-DMAP, DCC, DCC-DMAP, DCC-HOBt, DIC, TBTU, T3P added at 0° C. to obtain Formula I:

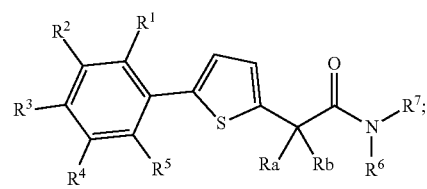

Formula I and e) Optionally purifying the compound by column chromatography.

Further, the present invention discloses the compounds of Formula I and their stereoisomers including diastereoisomers and enantiomers, pure or mixed racemic mixture, geometrical isomers, tautomers, salts, hydrates, solvates, solid forms, deuterated or any other isotopic forms and mixtures thereof.

The present invention discloses compounds of general Formula I, wherein R', $R^2$, $R^3$, $R^4$ and $R^5$ are independently selected from hydrogen, halogen and, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, a C3-C7 aromatic or aliphatic heterocycle comprising at least one hetero atom selected from a group of O, N and S; any of two adjacent R groups can forming a 5-6 membered aromatic or aliphatic ring comprising at least one hetero atom selected from a group of O, N and S.

The present invention discloses compounds of general Formula I, wherein a 5 or 6 membered cyclic ring having one or two hetero atoms from among O, N, and S is formed by any 2 adjacent groups selected from $R^1$, $R^2$, $R^3$, $R^4$ and $R^5$.

The compounds of Formula I wherein R6 and R7, together form a 3-7 membered aromatic or aliphatic heterocycle comprising at least one hetero atom selected from O, N, S further wherein the heterocycle is optionally substituted with any substituent selected from the group comprising halogen, CF3, straight chain or branched C1-C5 alkyl, straight chain or branched C2-C5 alkenyl or straight chain or branched C1-C5 alkoxy. Further, wherein the heterocycle is monosubstituted, disubstituted or trisubstituted.

Compounds of Formula I wherein any two adjacent substituents selected from R1, R2, R3, R4 and R5, combine to form naphthalene.

Without being bound by theory the inventors of the present invention have contemplated novel and inventive methods for modulating ER stress pathways in cells and/or in vivo.

Accordingly, the present invention discloses compounds of general Formula I that have been unexpectedly found to be successful in influencing the ER stress pathways in cells. Going further, the inventors envisage that the compounds of general Formula I to be useful in the treatment and prevention of diseases associated with deregulation of cellular stress pathways, more specifically ER stress. The diseases include but are not limited to cancers, tumors, metabolic disorders, neurodegeneration, cardiovascular, pulmonary, ophthalmic and dermatological disorders.

In addition, embodiments of the present invention relate to treatment and prevention of diseases/disorders involving the deregulation of immune system, including, but not limited to, Atopic Dermatitis, Urticaria, Rosacea, Actinic Keratosis and Alopecia In another embodiment, the present invention relates to the treatment and prevention of autoimmune diseases including, but not limited to, Type I Diabetes, Rheumatoid Arthritis, Lupus, Celiac Disease, Psoriatic Arthritis, Multiple Sclerosis, Pernicious Anemia, Sjogren's syndrome, Grave's Disease, Inflammatory bowel disease.

In another embodiment, the present invention relates to the treatment and prevention of autoimmune diseases related to skin including, but not limited to, Vitiligo, Psoriasis, lichen-planus, Scleroderma, Pemphigus, Bullous, Epidermolysis bullosa, Systemic lupus erythematosus, dermatomiositis, Alopecia areata.

The present invention discloses compounds of Formula I, that are useful for treatment and prevention of ER stress related diseases. The compounds of the present invention can be used by way of a formulation or a composition for therapeutics as well as prophylactic applications for the treatment of ER stress related diseases via all modes of administration.

For example, it is suitable for oral, parenteral, topical, transdermal, intravenous, rectal, sublingual and nasal administration. It is further envisaged that in the treatment of ER stress related diseases, the disclosed compounds of Formula I, may also be administered via intramuscular, subcutaneous, intravenous and peridural administration.

The compositions comprising the compounds of Formula I as active ingredients, are intended to be administered by any suitable route, including orally, parenterally, rectally, topically, intranasal, transdermal, sublingual, ocular and local administration. They may also be typically formulated and administered in unit-dosage forms such as tablets, capsules, pills, powders, granules, sterile parenteral solutions or suspensions, and oral solutions or suspensions, and oil-water emulsions containing suitable quantities of the active ingredient or multiple-dosage forms.

Suitable pharmaceutical preparations may also be prepared such as solutions, suspensions, tablets, dispersible tablets, pills, capsules, powders, sustained release formulations or elixirs, for oral administration or in sterile solutions or suspensions for any suitable mode of administration, as well as transdermal patch preparation and dry powder inhalers.

The present invention further envisages pharmaceutical composition, wherein the composition is in the form of a formulation that is administered in unit-dosage forms such as tablets, capsules, pills, powders, granules, sterile parenteral solutions or suspensions, and oral solutions or suspensions, injections, syrup, liquid, microemulsion, topical creams, ointments, suppositories, sachets, troches and lozenges and oil-water emulsions containing suitable quantities of the compound of Formula I or multiple-dosage forms.

An embodiment of the present invention is directed towards treatment of the subject displaying symptoms of ER stress related diseases, comprising steps of administering a therapeutically effective amount of one or more of the compounds of general Formula I, their stereoisomers (diastereoisomers, enantiomers), pure or mixed, racemic mixtures, geometrical isomers, tautomers, pharmaceutically acceptable salts, hydrates, solvates, solid forms and mixtures thereof.

Yet another embodiment of the present invention is directed towards treatment of autoimmune diseases of skin, by reducing the immune mediated cell death, comprising the steps of administering a therapeutically effective amount of one or more of the compounds of general Formula I or their physiologically acceptable salts, and still further, their stereoisomers (diastereoisomers, enantiomers), pure or mixed, racemic mixtures, geometrical isomers, tautomers, hydrates, solvates, solid forms and mixtures thereof.

Another embodiment of the present invention is directed towards the treatment of skin autoimmune diseases particularly, by reducing the autoimmune mediated cell death of melanocytes, comprising administering a therapeutically effective amount of a pharmaceutical composition or formulation comprising essentially of one or more compounds of Formula I. Another embodiment of the invention is directed to a method of treating a subject who has developed vitiligo, with a pharmaceutically effective amount the one or more compound of Formula I or, their stereoisomers (diastereoisomers, enantiomers), pure or mixed, racemic mixtures, geometrical isomers, tautomers, pharmaceutically acceptable salts, hydrates, solvates, solid forms and mixtures thereof.

The present invention envisages treatment of autoimmune diseases by administering one or more the compounds of general Formula I by way of a pharmaceutical composition comprising an effective amount of tone or more of the said compounds and a pharmaceutically acceptable carrier.

The present invention further envisages the process of preparing a pharmaceutical composition by mixing an effective amount of the one or more of the said compounds and a pharmaceutically acceptable carrier.

Particularly, a further embodiment of the present invention is directed towards the preparation of a pharmaceutical composition comprising an effective amount of one or more of the said compounds and a pharmaceutically acceptable carrier further adapted to be administered by any suitable mode of administration including oral, parenteral, rectal, topical, intranasal, transdermal, sublingual, ocular and any other local mode of administration.

The present invention envisages application of the compounds of general Formula I, their stereoisomers (diastereoisomers, enantiomers), pure or mixed, racemic mixtures, geometrical isomers, tautomers, pharmaceutically acceptable salts, hydrates, solvates, solid forms and mixtures thereof in any process including medicinal, prophylactic, curative, diagnostic, therapeutic or surgical in order to prevent or treat ER stress related diseases.

The present invention also envisages the application of the compounds of general Formula I or their physiologically acceptable salts, and still further, their stereoisomers (diastereoisomers, enantiomers), pure or mixed, racemic mixtures, geometrical isomers, tautomers, hydrates, solvates, solid forms and mixtures thereof, to effect prophylactic or maintenance therapy in a subject that may have a genetic propensity towards ER stress related diseases and such subjects who have been treated for such disease and undergone disease regression.

A preferred embodiment of the present invention is directed towards compounds of the general Formula I as provided below:

N-butyl-2-(5-(4-chlorophenyl)thiophen-2-yl)acetamide
2-(5-(4-chlorophenyl)thiophen-2-yl)-N-(3-isopropoxypropyl)acetamide
2-(5-(4-chlorophenyl)thiophen-2-yl)-1-(pyrrolidin-1-yl)ethan-1-one
2-(5-(4-chlorophenyl)thiophen-2-yl)-1-(4-methylpiperazin-1-yl)ethan-1-one
2-(5-(4-chlorophenyl)thiophen-2-yl)-N-(4-fluorophenethyl)acetamide
2-(5-(4-chlorophenyl)thiophen-2-yl)-N-(2-(pyrrolidin-1-yl)ethyl)acetamide
2-(5-(4-chlorophenyl)thiophen-2-yl)-1-(3,5-dimethylmorpholino)ethan-1-one
2-(5-(4-chlorophenyl)thiophen-2-yl)-N-cyclopentylacetamide
2-(5-(4-chlorophenyl)thiophen-2-yl)-N-(4-fluorophenyl)acetamide
2-(5-(4-chlorophenyl)thiophen-2-yl)-N-(3-(trifluoromethyl)phenyl)acetamide
2-(5-(4-chlorophenyl)thiophen-2-yl)-N-(3,5-difluorobenzyl)acetamide
N-(3-(1H-imidazol-1-yl)propyl)-2-(5-(4-chlorophenyl)thiophen-2-yl)acetamide
2-(5-(4-Chlorophenyl)thiophen-2-yl)-N-(2-(piperidin-1-yl)ethyl)acetamide
2-(5-(4-Chlorophenyl)thiophen-2-yl)-N-(2-(dimethylamino)ethyl)acetamide
2-(5-(4-chlorophenyl)thiophen-2-yl)-N-(2-morpholinoethyl)acetamide hydrochloride
2-(5-(4-chlorophenyl)thiophen-2-yl)-2-methyl-1-(4-methylpiperazin-1-yl)propan-1-one
2-(5-(4-chlorophenyl)thiophen-2-yl)-2-methyl-N-(2-(piperidin-1-yl)ethyl)propanamide
N-(3-(1H-imidazol-1-yl)propyl)-2-(5-(4-chlorophenyl)thiophen-2-yl)-2-methylpropanamide
2-(5-(4-chlorophenyl)thiophen-2-yl)-1-(4,4-difluoropiperidin-1-yl)ethan-1-one
2-(5-(4-fluorophenyl)thiophen-2-yl)-1-(4-methylpiperazin-1-yl)ethan-1-one
N-(4-fluorophenethyl)-2-(5-(4-fluorophenyl)thiophen-2-yl)acetamide
2-(5-(4-fluorophenyl)thiophen-2-yl)-N-(2-morpholinoethyl)acetamide
2-(5-(4-fluorophenyl)thiophen-2-yl)-N-(2-(piperidin-1-yl)ethyl)acetamide
N-(3-(1H-imidazol-1-yl)propyl)-2-(5-(4-fluorophenyl)thiophen-2-yl)acetamide
2-(5-(2,4-dichlorophenyl)thiophen-2-yl)-1-(4-methylpiperazin-1-yl)ethan-1-one
2-(5-(2,4-dichlorophenyl)thiophen-2-yl)-N-(4-fluorophenethyl)acetamide
2-(5-(2,4-dichlorophenyl)thiophen-2-yl)-N-(2-morpholinoethyl)acetamide
1-(4-methylpiperazin-1-yl)-2-(5-phenylthiophen-2-yl)ethan-1-one
N-(4-fluorophenethyl)-2-(5-phenylthiophen-2-yl)acetamide
N-(2-morpholinoethyl)-2-(5-phenylthiophen-2-yl)acetamide
2-(5-(2,4-dichlorophenyl)thiophen-2-yl)-N-(2-(piperidin-1-yl)ethyl)acetamide
2-(5-phenylthiophen-2-yl)-N-(2-(piperidin-1-yl)ethyl)acetamide
N-(3-(1H-imidazol-1-yl)propyl)-2-(5-phenylthiophen-2-yl)acetamide
N-(3-(1H-imidazol-1-yl)propyl)-2-(5-(2,4-dichlorophenyl)thiophen-2-yl)acetamide
2-(5-(3-fluorophenyl)thiophen-2-yl)-1-(4-methylpiperazin-1-yl)ethan-1-one
2-(5-(3-fluorophenyl)thiophen-2-yl)-N-(2-morpholinoethyl)acetamide
2-(5-(2,4-dichlorophenyl)thiophen-2-yl)-N-(2-(1,1-dioxidothiomorpholino)ethyl)acetamide
2-(5-(2,4-dichlorophenyl)thiophen-2-yl)-N-(2-(4-methylpiperazin-1-yl)ethyl)acetamide
2-(5-(3-chlorophenyl)thiophen-2-yl)-1-(4-methylpiperazin-1-yl)ethan-1-one
2-(5-(3-chlorophenyl)thiophen-2-yl)-N-(2-morpholinoethyl)acetamide
2-(5-(3,5-dichlorophenyl)thiophen-2-yl)-N-(2-morpholinoethyl)acetamide
2-(5-(4-methoxyphenyl)thiophen-2-yl)-N-(2-morpholinoethyl)acetamide
N-(2-morpholinoethyl)-2-(5-(4-(trifluoromethyl)phenyl)thiophen-2-yl)acetamide
2-(5-(3-(3,5-dimethyl-1H-pyrazol-1-yl)phenyl)thiophen-2-yl)-N-(2-morpholinoethyl)acetamide
2-(5-(4-chlorophenyl)thiophen-2-yl)-N-(3-morpholinopropyl)acetamide
2-(5-(2,4-dichlorophenyl)thiophen-2-yl)-N-(3-(1,1-dioxidothiomorpholino)propyl)acetamide
2-(5-(3-bromophenyl)thiophen-2-yl)-N-(2-morpholinoethyl)acetamide
N-(2-morpholinoethyl)-2-(5-(3-morpholinophenyl)thiophen-2-yl)acetamide
2-(5-(3-(1-methyl-1H-pyrazol-4-yl)phenyl)thiophen-2-yl)-N-(2-morpholinoethyl)acetamide
2-(5-(3-(1-methyl-1H-pyrrol-2-yl)phenyl)thiophen-2-yl)-N-(2-morpholinoethyl)acetamide
N-(2-morpholinoethyl)-2-(5-(3-(pyrazin-2-yl)phenyl)thiophen-2-yl)acetamide
2-(5-(4-chlorophenyl)thiophen-2-yl)-1-morpholinoethan-1-one
2-(5-(4-chlorophenyl)thiophen-2-yl)-1-thiomorpholinoethan-1-one
2-(5-(3-(1-methyl-1H-imidazol-4-yl)phenyl)thiophen-2-yl)-N-(2-morpholinoethyl)acetamide
2-(5-(3,5-dichlorophenyl)thiophen-2-yl)-N-(3-morpholinopropypacetamide
2-(5-(3,5-dichlorophenyl)thiophen-2-yl)-N-(2-(1,1-dioxidothiomorpholino)ethyl)acetamide
2-(5-(3,5-dichlorophenyl)thiophen-2-yl)-N-(3-(1,1-dioxidothiomorpholino)propyl)acetamide
2-(5-(3,5-dichlorophenyl)thiophen-2-yl)-1-morpholinoethan-1-one 2-(5-(3,5-dichlorophenyl)thiophen-2-yl)-1-thiomorpholino-ethan-1-one
2-(5-(3,5-dichlorophenyl)thiophen-2-yl)-1-(4-(4-fluorophenyl)piperidin-1-yl)ethan-1-one
2-(5-(2,4-dichlorophenyl)thiophen-2-yl)-N-morpholinoacetamide
2-(5-(2,6-dichlorophenyl)thiophen-2-yl)-N-(3-(1,1-dioxidothiomorpholino)propyl) acetamide
2-(5-(2,6-dichlorophenyl)thiophen-2-yl)-N-(2-morpholinoethyl)acetamide
2-(5-(2,4-dichlorophenyl)thiophen-2-yl)-N-(piperidin-1-yl)acetamide
(1-(5-(4-chlorophenyl)thiophen-2-yl)cyclopropyl)(4-methylpiperazin-1-yl)methanone
(1-(5-(4-chlorophenyl)thiophen-2-yl)cyclobutyl)(4-methylpiperazin-1-yl)methanone
(3-(5-(4-chlorophenyl)thiophen-2-yl)oxetan-3-yl)(4-methylpiperazin-1-yl)methanone
(1-(5-(4-fluorophenyl)thiophen-2-yl)cyclopropyl)(4-methylpiperazin-1-yl)methanone
(1-(5-(4-fluorophenyl)thiophen-2-yl)cyclobutyl)(4-methylpiperazin-1-yl)methanone
(3-(5-(4-fluorophenyl)thiophen-2-yl)oxetan-3-yl)(4-methylpiperazin-1-yl)methanone
N-butyl-2-(5-(naphthalen-1-yl)thiophen-2-yl)acetamide
2-(5-(3,5-dichlorophenyl)thiophen-2-yl)-N-morpholinoacetamide Without limiting the scope of the invention, an another advantageous embodiment of the present invention is directed towards preferred compounds chosen from among the following:

| Compound No | | Structure | IUPAC name |
|---|---|---|---|
| 1. | AB1010 | 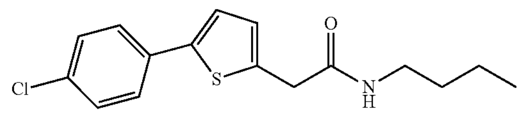 [SMILES: CCCCNC(=O)Cc1ccc(-c2ccc(Cl)cc2)s1] | N-butyl-2-(5-(4-chlorophenyl)thiophen-2-yl)acetamide |
| 2. | AB1012 | 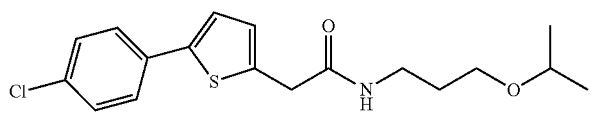 [SMILES: CC(C)OCCCNC(=O)Cc1ccc(-c2ccc(Cl)cc2)s1] | 2-(5-(4-chlorophenyl)thiophen-2-yl)-N-(3-isopropoxypropyl)acetamide |
| 3. | AB1013 | 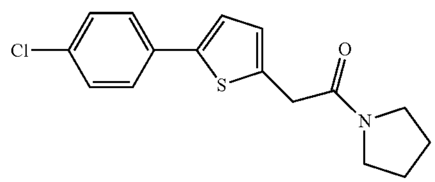 [SMILES: O=C(Cc1ccc(-c2ccc(Cl)cc2)s1)N1CCCC1] | 2-(5-(4-chlorophenyl)thiophen-2-yl)-1-(pyrrolidin-1-yl)ethan-1-one |
| 4. | AB1014 | 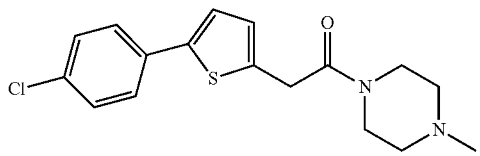 [SMILES: CN1CCN(C(=O)Cc2ccc(-c3ccc(Cl)cc3)s2)CC1] | 2-(5-(4-chlorophenyl)thiophen-2-yl)-1-(4-methylpiperazin-1-yl)ethan-1-one |
| 5. | AB1015 | 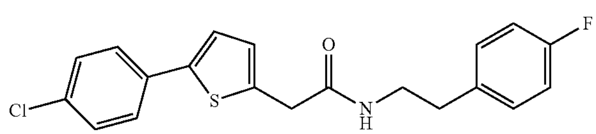 [SMILES: O=C(Cc1ccc(-c2ccc(Cl)cc2)s1)NCCc1ccc(F)cc1] | 2-(5-(4-chlorophenyl)thiophen-2-yl)-N-(4-fluorophenethyl)acetamide |
| 6. | AB1016 | 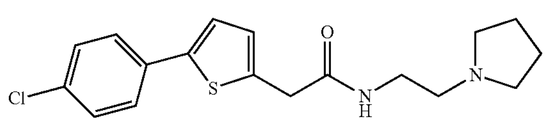 [SMILES: O=C(Cc1ccc(-c2ccc(Cl)cc2)s1)NCCN1CCCC1] | 2-(5-(4-chlorophenyl)thiophen-2-yl)-N-(2-(pyrrolidin-1-yl)ethyl)acetamide |
| 7. | AB1018 | 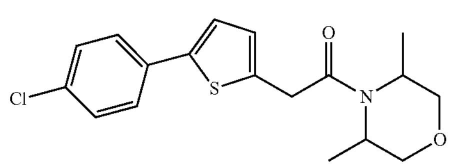 [SMILES: CC1COCC(C)N1C(=O)Cc1ccc(-c2ccc(Cl)cc2)s1] | 2-(5-(4-chlorophenyl)thiophen-2-yl)-1-(3,5-dimethylmorpholino)ethan-1-one |
| 8. | AB1019 | 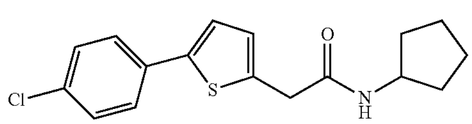 [SMILES: O=C(Cc1ccc(-c2ccc(Cl)cc2)s1)NC1CCCC1] | 2-(5-(4-chlorophenyl)thiophen-2-yl)-N-cyclopentylacetamide |

-continued

| Compound No | | Structure | IUPAC name |
|---|---|---|---|
| 9. | AB1020 | 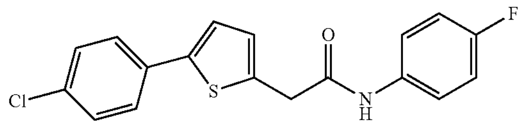 [SMILES: O=C(Cc1ccc(-c2ccc(Cl)cc2)s1)Nc1ccc(F)cc1] | 2-(5-(4-chlorophenyl)thiophen-2-yl)-N-(4-fluorophenyl)acetamide |
| 10 | AB1021 | 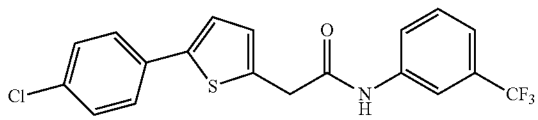 [SMILES: O=C(Cc1ccc(-c2ccc(Cl)cc2)s1)Nc1cccc(C(F)(F)F)c1] | 2-(5-(4-chlorophenyl)thiophen-2-yl)-N-(3-(trifluoromethyl)phenyl)acetamide |
| 11 | AB1022 | 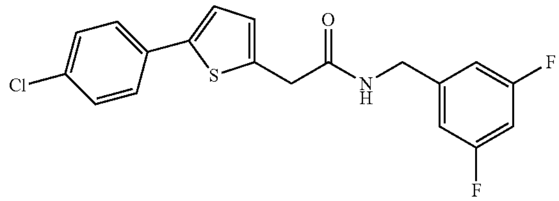 [SMILES: O=C(Cc1ccc(-c2ccc(Cl)cc2)s1)NCc1cc(F)cc(F)c1] | 2-(5-(4-chlorophenyl)thiophen-2-yl)-N-(3,5-difluorobenzyl)acetamide |
| 12 | AB1045 | 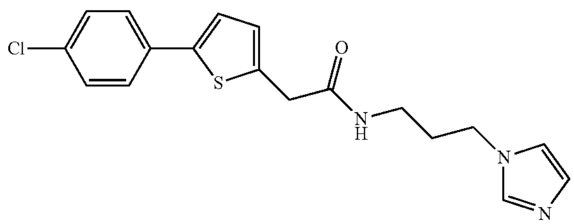 [SMILES: O=C(Cc1ccc(-c2ccc(Cl)cc2)s1)NCCCn1ccnc1] | N-(3-(1H-imidazol-1-yl)propyl)-2-(5-(4-chlorophenyl)thiophen-2-yl)acetamide |
| 13 | AB1047 | 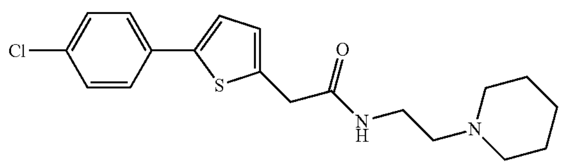 [SMILES: O=C(Cc1ccc(-c2ccc(Cl)cc2)s1)NCCN1CCCCC1] | 2-(5-(4-Chlorophenyl)thiophen-2-yl)-N-(2-(piperidin-1-yl)ethyl)acetamide |
| 14 | AB1051 | 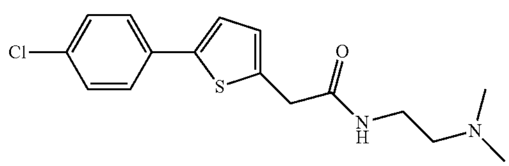 [SMILES: CN(C)CCNC(=O)Cc1ccc(-c2ccc(Cl)cc2)s1] | 2-(5-(4-Chlorophenyl)thiophen-2-yl)-N-(2-(dimethylamino)ethyl)acetamide |
| 15 | AB1062 | 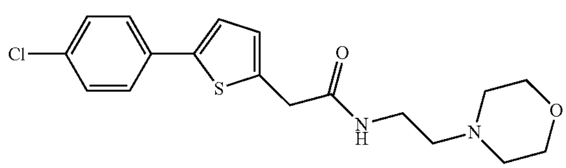 | 2-(5-(4-chlorophenyl)thiophen-2-yl)-N-(2-morpholinoethyl)acetamide hydrochloride |
| 16 | AB1078 | 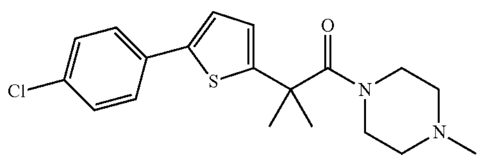 [SMILES: CN1CCN(C(=O)C(C)(C)c2ccc(-c3ccc(Cl)cc3)s2)CC1] | 2-(5-(4-chlorophenyl)thiophen-2-yl)-2-methyl-1-(4-methylpiperazin-1-yl)propan-1-one |
| 17 | AB1079 | 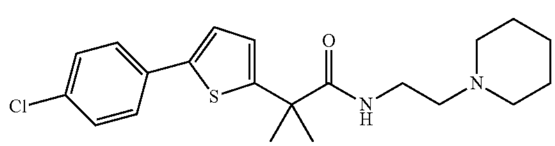 [SMILES: CC(C)(C(=O)NCCN1CCCCC1)c1ccc(-c2ccc(Cl)cc2)s1] | 2-(5-(4-chlorophenyl)thiophen-2-yl)-2-methyl-N-(2-(piperidin-1-yl)ethyl)propanamide |

-continued

| Compound No | | Structure | IUPAC name |
|---|---|---|---|
| 18 | AB1080 | 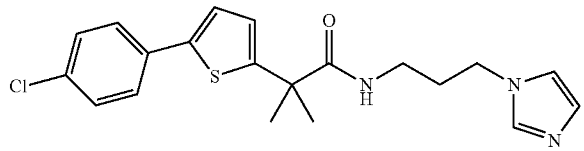 [SMILES: CC(C)(C(=O)NCCCn1ccnc1)c1ccc(-c2ccc(Cl)cc2)s1] | N-(3-(1H-imidazol-1-yl)propyl)-2-(5-(4-chlorophenyl)thiophen-2-yl)-2-methylpropanamide |
| 19 | AB1090 | 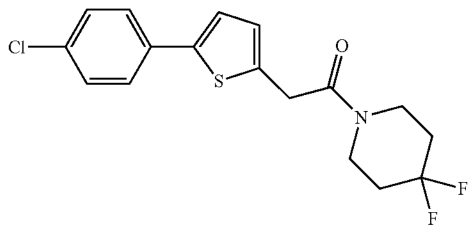 [SMILES: O=C(Cc1ccc(-c2ccc(Cl)cc2)s1)N1CCC(F)(F)CC1] | 2-(5-(4-chlorophenyl)thiophen-2-yl)-1-(4,4-difluoropiperidin-1-yl)ethan-1-one |
| 20 | AB1091 | 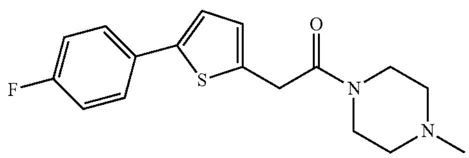 [SMILES: CN1CCN(C(=O)Cc2ccc(-c3ccc(F)cc3)s2)CC1] | 2-(5-(4-fluorophenyl)thiophen-2-yl)-1-(4-methylpiperazin-1-yl)ethan-1-one |
| 21 | AB1092 | 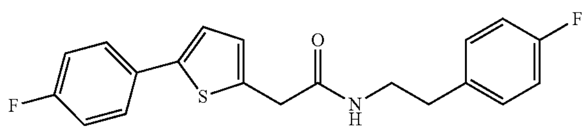 [SMILES: O=C(Cc1ccc(-c2ccc(F)cc2)s1)NCCc1ccc(F)cc1] | N-(4-fluorophenethyl)-2-(5-(4-fluorophenyl)thiophen-2-yl)acetamide |
| 22 | AB1093 | 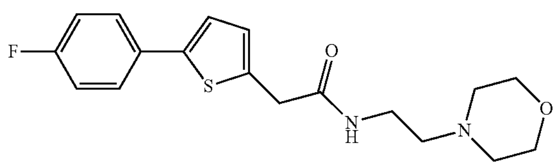 [SMILES: O=C(Cc1ccc(-c2ccc(F)cc2)s1)NCCN1CCOCC1] | 2-(5-(4-fluorophenyl)thiophen-2-yl)-N-(2-morpholinoethyl)acetamide |
| 23 | AB1094 | 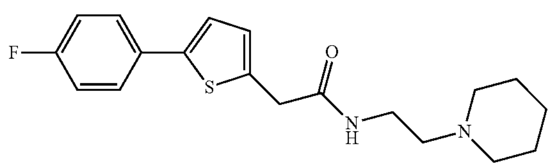 [SMILES: O=C(Cc1ccc(-c2ccc(F)cc2)s1)NCCN1CCCCC1] | 2-(5-(4-fluorophenyl)thiophen-2-yl)-N-(2-(piperidin-1-yl)ethyl)acetamide |
| 24 | AB1095 | 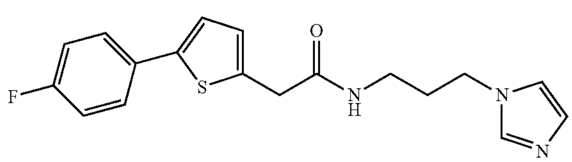 [SMILES: O=C(Cc1ccc(-c2ccc(F)cc2)s1)NCCCn1ccnc1] | N-(3-(1H-imidazol-1-yl)propyl)-2-(5-(4-fluorophenyl)thiophen-2-yl)acetamide |
| 25 | AB1097 | 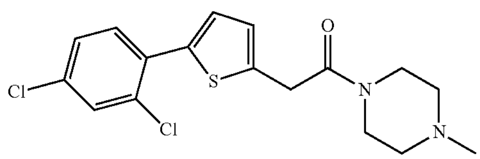 [SMILES: CN1CCN(C(=O)Cc2ccc(-c3ccc(Cl)cc3Cl)s2)CC1] | 2-(5-(2,4-dichlorophenyl)thiophen-2-yl)-1-(4-methylpiperazin-1-yl)ethan-1-one |
| 26 | AB1098 | 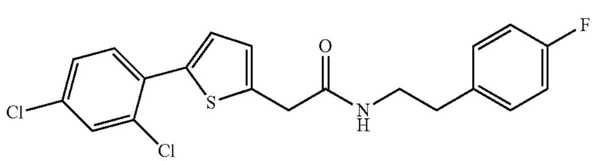 [SMILES: O=C(Cc1ccc(-c2ccc(Cl)cc2Cl)s1)NCCc1ccc(F)cc1] | 2-(5-(2,4-dichlorophenyl)thiophen-2-yl)-N-(4-fluorophenethyl)acetamide |

-continued

| Compound No | | Structure | IUPAC name |
|---|---|---|---|
| 27 | AB1099 | 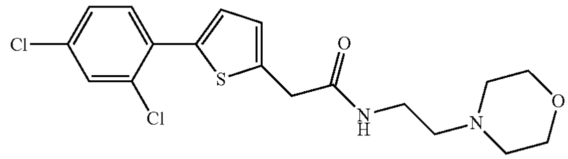 [SMILES: O=C(Cc1ccc(-c2ccc(Cl)cc2Cl)s1)NCCN1CCOCC1] | 2-(5-(2,4-dichlorophenyl)thiophen-2-yl)-N-(2-morpholinoethyl)acetamide |
| 28 | AB1100 | 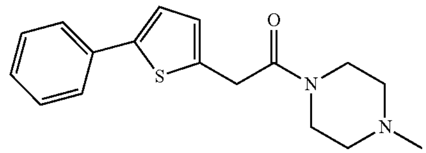 [SMILES: CN1CCN(C(=O)Cc2ccc(-c3ccccc3)s2)CC1] | 1-(4-methylpiperazin-1-yl)-2-(5-phenylthiophen-2-yl)ethan-1-one |
| 29 | AB1101 | 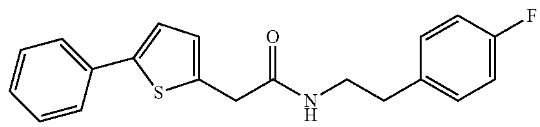 [SMILES: O=C(Cc1ccc(-c2ccccc2)s1)NCCc1ccc(F)cc1] | N-(4-fluorophenethyl)-2-(5-phenylthiophen-2-yl)acetamide |
| 30 | AB1102 | 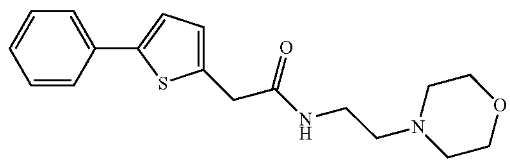 [SMILES: O=C(Cc1ccc(-c2ccccc2)s1)NCCN1CCOCC1] | N-(2-morpholinoethyl)-2-(5-phenylthiophen-2-yl)acetamide |
| 31 | AB1103 | 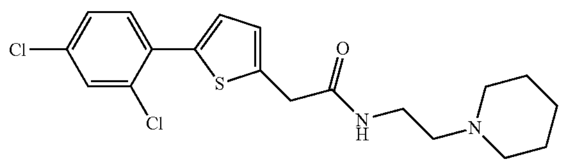 [SMILES: O=C(Cc1ccc(-c2ccc(Cl)cc2Cl)s1)NCCN1CCCCC1] | 2-(5-(2,4-dichlorophenyl)thiophen-2-yl)-N-(2-(piperidin-1-yl)ethyl)acetamide |
| 32 | AB1104 | 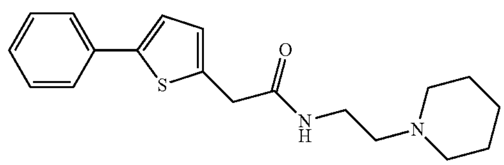 [SMILES: O=C(Cc1ccc(-c2ccccc2)s1)NCCN1CCCCC1] | 2-(5-phenylthiophen-2-yl)-N-(2-(piperidin-1-yl)ethyl)acetamide |
| 33 | AB1105 | 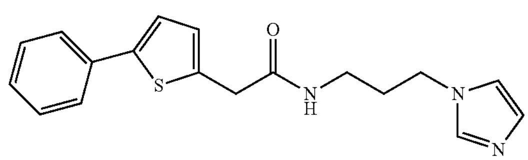 [SMILES: O=C(Cc1ccc(-c2ccccc2)s1)NCCCn1ccnc1] | N-(3-(1H-imidazol-1-yl)propyl)-2-(5-phenylthiophen-2-yl)acetamide |
| 34 | AB1106 | 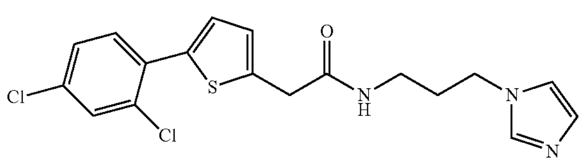 [SMILES: O=C(Cc1ccc(-c2ccc(Cl)cc2Cl)s1)NCCCn1ccnc1] | N-(3-(1H-imidazol-1-yl)propyl)-2-(5-(2,4-dichlorophenyl)thiophen-2-yl)acetamide |
| 35 | AB1107 | 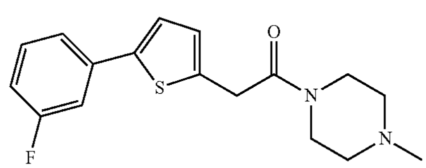 [SMILES: CN1CCN(C(=O)Cc2ccc(-c3cccc(F)c3)s2)CC1] | 2-(5-(3-fluorophenyl)thiophen-2-yl)-1-(4-methylpiperazin-1-yl)ethan-1-one |

-continued

| Compound No | | Structure | IUPAC name |
|---|---|---|---|
| 36 | AB1108 | 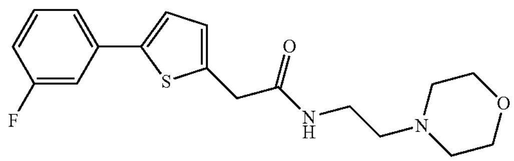 [SMILES: O=C(Cc1ccc(-c2cccc(F)c2)s1)NCCN1CCOCC1] | 2-(5-(3-fluorophenyl)thiophen-2-yl)-N-(2-morpholinoethyl)acetamide |
| 37 | AB1109 | 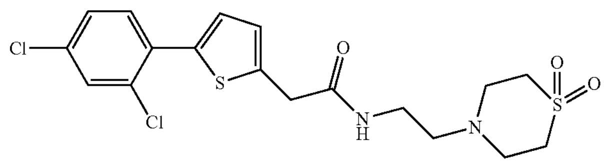 [SMILES: O=C(Cc1ccc(-c2ccc(Cl)cc2Cl)s1)NCCN1CCS(=O)(=O)CC1] | 2-(5-(2,4-dichlorophenyl)thiophen-2-yl)-N-(2-(1,1-dioxidothiomorpholino)ethyl)acetamide |
| 38 | AB1110 | 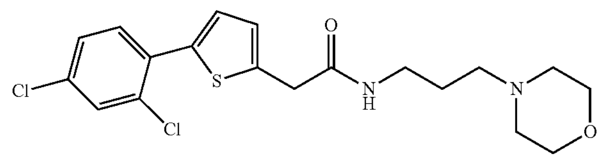 [SMILES: O=C(Cc1ccc(-c2ccc(Cl)cc2Cl)s1)NCCCN1CCOCC1] | 2-(5-(2,4-dichlorophenyl)thiophen-2-yl)-N-(3-morpholinopropyl)acetamide |
| 39 | AB1111 | 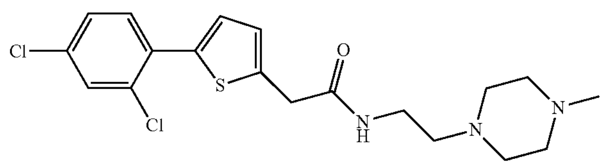 | 2-(5-(2,4-dichlorophenyl)thiophen-2-yl)-N-(2-(4-methylpiperazin-1-yl)ethyl)acetamide hydrochloride |
| 40 | AB1112 | 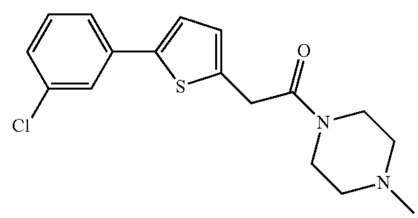 [SMILES: CN1CCN(C(=O)Cc2ccc(-c3cccc(Cl)c3)s2)CC1] | 2-(5-(3-chlorophenyl)thiophen-2-yl)-1-(4-methylpiperazin-1-yl)ethan-1-one |
| 41 | AB1113 | 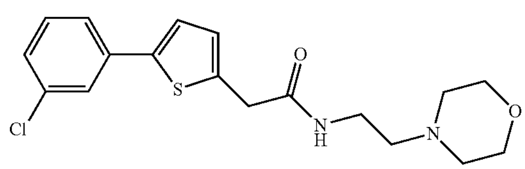 [SMILES: O=C(Cc1ccc(-c2cccc(Cl)c2)s1)NCCN1CCOCC1] | 2-(5-(3-chlorophenyl)thiophen-2-yl)-N-(2-morpholinoethyl)acetamide |
| 42 | AB1114 | 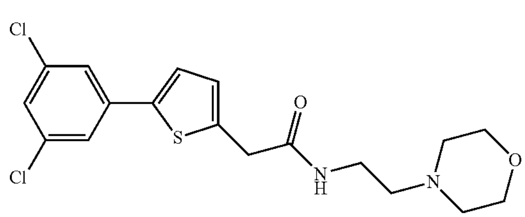 [SMILES: O=C(Cc1ccc(-c2cc(Cl)cc(Cl)c2)s1)NCCN1CCOCC1] | 2-(5-(3,5-dichlorophenyl)thiophen-2-yl)-N-(2-morpholinoethyl)acetamide |
| 43 | AB1115 | 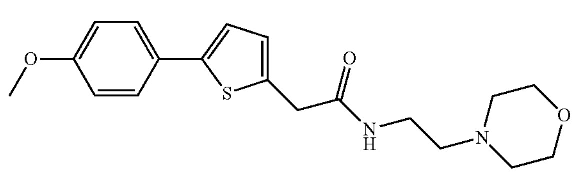 [SMILES: COc1ccc(-c2ccc(CC(=O)NCCN3CCOCC3)s2)cc1] | 2-(5-(4-methoxyphenyl)thiophen-2-yl)-N-(2-morpholinoethyl)acetamide |

-continued

| Compound No | | Structure | IUPAC name |
|---|---|---|---|
| 44 | AB1116 | 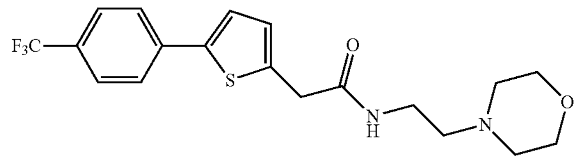 [SMILES: O=C(Cc1ccc(-c2ccc(C(F)(F)F)cc2)s1)NCCN1CCOCC1] | N-(2-morpholinoethyl)-2-(5-(4-(trifluoromethyl)phenyl)thiophen-2-yl)acetamide |
| 45 | AB1117 | 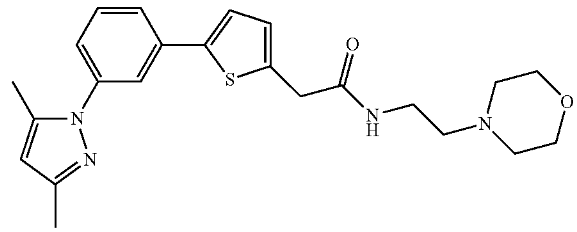 [SMILES: Cc1cc(C)n(-c2cccc(-c3ccc(CC(=O)NCCN4CCOCC4)s3)c2)n1] | 2-(5-(3-(3,5-dimethyl-1H-pyrazol-1-yl)phenyl)thiophen-2-yl)-N-(2-morpholinoethyl)acetamide |
| 46 | AB1118 | 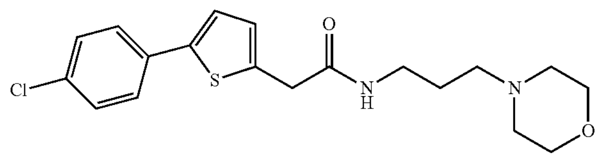 [SMILES: O=C(Cc1ccc(-c2ccc(Cl)cc2)s1)NCCCN1CCOCC1] | 2-(5-(4-chlorophenyl)thiophen-2-yl)-N-(3-morpholinopropyl)acetamide |
| 47 | AB1119 | 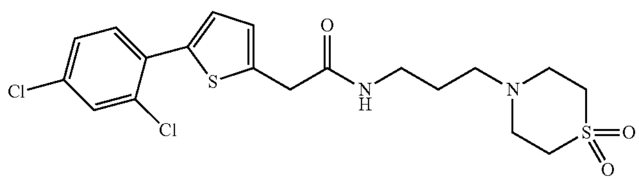 [SMILES: O=C(Cc1ccc(-c2ccc(Cl)cc2Cl)s1)NCCCN1CCS(=O)(=O)CC1] | 2-(5-(2,4-dichlorophenyl)thiophen-2-yl)-N-(3-(1,1-dioxidothiomorpholino)propyl)acetamide |
| 48 | AB1120 | 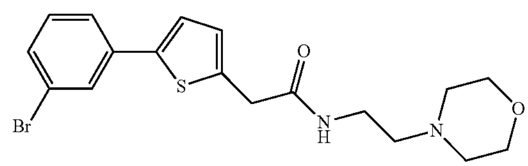 [SMILES: O=C(Cc1ccc(-c2cccc(Br)c2)s1)NCCN1CCOCC1] | 2-(5-(3-bromophenyl)thiophen-2-yl)-N-(2-morpholinoethyl)acetamide |
| 49 | AB1122 | 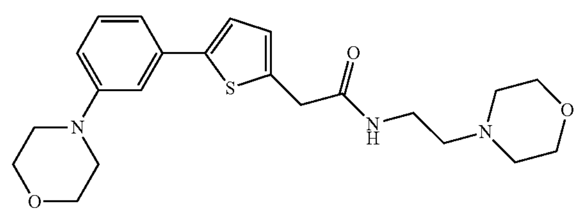 [SMILES: O=C(Cc1ccc(-c2cccc(N3CCOCC3)c2)s1)NCCN1CCOCC1] | N-(2-morpholinoethyl)-2-(5-(3-morpholinophenyl)thiophen-2-yl)acetamide |
| 50 | AB1123 | 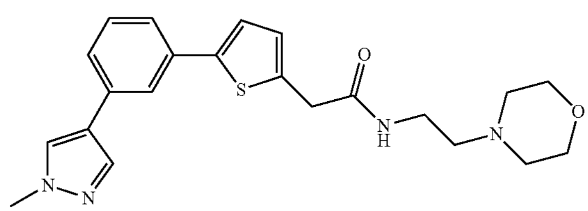 [SMILES: Cn1cc(-c2cccc(-c3ccc(CC(=O)NCCN4CCOCC4)s3)c2)cn1] | 2-(5-(3-(1-methyl-1H-pyrazol-4-yl)phenyl)thiophen-2-yl)-N-(2-morpholinoethyl)acetamide |
| 51 | AB1146 | 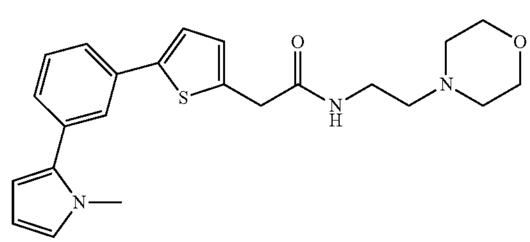 [SMILES: Cn1cccc1-c1cccc(-c2ccc(CC(=O)NCCN3CCOCC3)s2)c1] | 2-(5-(3-(1-methyl-1H-pyrrol-2-yl)phenyl)thiophen-2-yl)-N-(2-morpholinoethyl)acetamide |

-continued

| Compound No | Structure | IUPAC name |
|---|---|---|
| 52 AB1147 | | N-(2-morpholinoethyl)-2-(5-(3-(pyrazin-2-yl)phenyl)thiophen-2-yl)acetamide |
| 53 AB1151 | | 2-(5-(4-chlorophenyl)thiophen-2-yl)-1-morpholinoethan-1-one |
| 54 AB1152 | | 2-(5-(4-chlorophenyl)thiophen-2-yl)-1-thiomorpholinoethan-1-one |
| 55 AB1153 | | 2-(5-(3-(1-methyl-1H-imidazol-4-yl)phenyl)thiophen-2-yl)-N-(2-morpholinoethyl)acetamide |
| 56 AB1162 | | 2-(5-(3,5-dichlorophenyl)thiophen-2-yl)-N-(3-morpholinopropyl)acetamide |
| 57 AB1163 | | 2-(5-(3,5-dichlorophenyl)thiophen-2-yl)-N-(2-(1,1-dioxidothiomorpholino)ethyl)acetamide |
| 58 AB1164 | | 2-(5-(3,5-dichlorophenyl)thiophen-2-yl)-N-(3-(1,1-dioxidothiomorpholino)propyl)acetamide |
| 59 AB1176 | | 2-(5-(3,5-dichlorophenyl)thiophen-2-yl)-1-morpholinoethan-1-one |

-continued

| Compound No | | Structure | IUPAC name |
|---|---|---|---|
| 60 | AB1177 | 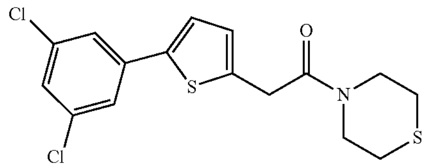 [SMILES: O=C(Cc1ccc(-c2cc(Cl)cc(Cl)c2)s1)N1CCOCC1] | 2-(5-(3,5-dichlorophenyl)thiophen-2-yl)-1-thiomorpholinoethan-1-one |
| 61 | AB1178 | 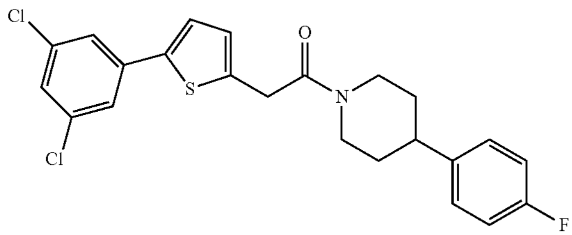 [SMILES: O=C(Cc1ccc(-c2cc(Cl)cc(Cl)c2)s1)N1CCC(c2ccc(F)cc2)CC1] | 2-(5-(3,5-dichlorophenyl)thiophen-2-yl)-1-(4-(4-fluorophenyl)piperidin-1-yl)ethan-1-one |
| 62 | AB1179 | 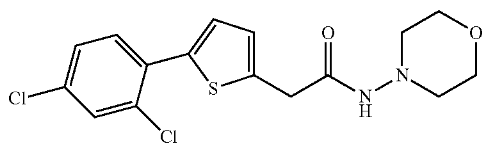 [SMILES: O=C(Cc1ccc(-c2ccc(Cl)cc2Cl)s1)NN1CCOCC1] | 2-(5-(2,4-dichlorophenyl)thiophen-2-yl)-N-morpholinoacetamide |
| 63 | AB1180 | 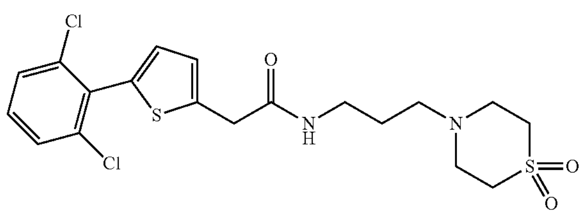 [SMILES: O=C(Cc1ccc(-c2c(Cl)cccc2Cl)s1)NCCCN1CCS(=O)(=O)CC1] | 2-(5-(2,6-dichlorophenyl)thiophen-2-yl)-N-(3-(1,1-dioxidothiomorpholino)propyl) |
| 64 | AB1181 | 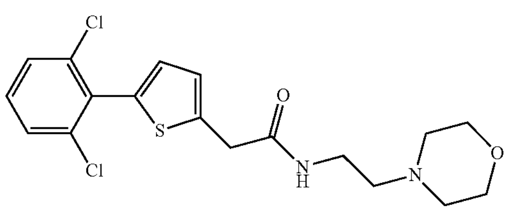 [SMILES: O=C(Cc1ccc(-c2c(Cl)cccc2Cl)s1)NCCN1CCOCC1] | 2-(5-(2,6-dichlorophenyl)thiophen-2-yl)-N-(2-morpholinoethyl)acetamide |
| 65 | | 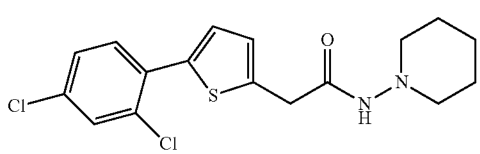 [SMILES: O=C(Cc1ccc(-c2ccc(Cl)cc2Cl)s1)NN1CCCCC1] | 2-(5-(2,4-dichlorophenyl)thiophen-2-yl)-N-(piperidin-1-yl)acetamide |
| 66 | | 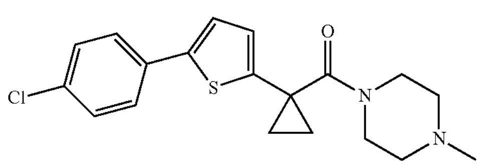 [SMILES: CN1CCN(C(=O)C2(c3ccc(-c4ccc(Cl)cc4)s3)CC2)CC1] | (1-(5-(4-chlorophenyl)thiophen-2-yl)cyclopropyl)(4-methylpiperazin-1-yl)methanone |
| 67 | | 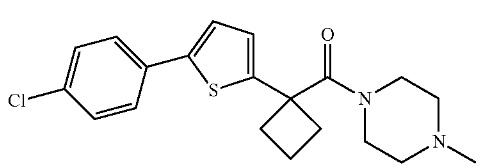 [SMILES: CN1CCN(C(=O)C2(c3ccc(-c4ccc(Cl)cc4)s3)CCC2)CC1] | (1-(5-(4-chlorophenyl)thiophen-2-yl)cyclobutyl)(4-methylpiperazin-1-yl)methanone |

-continued

| Compound No | Structure | IUPAC name |
|---|---|---|
| 68 | 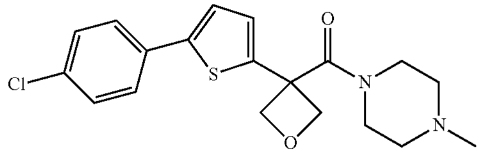 [SMILES: CN1CCN(C(=O)C2(c3ccc(-c4ccc(Cl)cc4)s3)COC2)CC1] | (3-(5-(4-chlorophenyl)thiophen-2-yl)oxetan-3-yl)(4-methylpiperazin-1-yl)methanone |
| 69 | 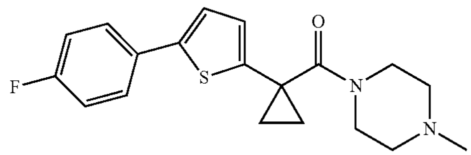 [SMILES: CN1CCN(C(=O)C2(c3ccc(-c4ccc(F)cc4)s3)CC2)CC1] | (1-(5-(4-fluorophenyl)thiophen-2-yl)cyclopropyl)(4-methylpiperazin-1-yl)methanone |
| 70 | 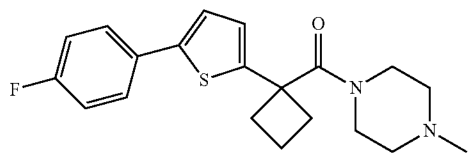 [SMILES: CN1CCN(C(=O)C2(c3ccc(-c4ccc(F)cc4)s3)CCC2)CC1] | (1-(5-(4-fluorophenyl)thiophen-2-yl)cyclobutyl)(4-methylpiperazin-1-yl)methanone |
| 71 | 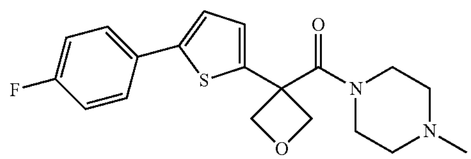 [SMILES: CN1CCN(C(=O)C2(c3ccc(-c4ccc(F)cc4)s3)COC2)CC1] | (3-(5-(4-fluorophenyl)thiophen-2-yl)oxetan-3-yl)(4-methylpiperazin-1-yl)methanone |
| 72 | 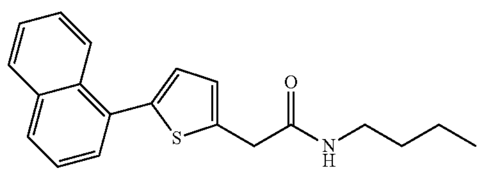 [SMILES: CCCCNC(=O)Cc1ccc(-c2cccc3ccccc23)s1] | N-butyl-2-(5-(naphthalen-1-yl)thiophen-2-yl)acetamide |
| 73 | 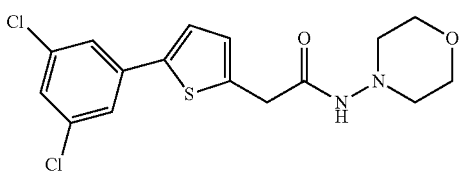 [SMILES: O=C(Cc1ccc(-c2cc(Cl)cc(Cl)c2)s1)NN1CCOCC1] | 2-(5-(3,5-dichlorophenyl)thiophen-2-yl)-N-morpholinoacetamide |

The present invention further describes novel and inventive process for the preparation of the compounds of the present invention. The compounds of general Formula I have been synthesized by a novel process having the general scheme as given below:

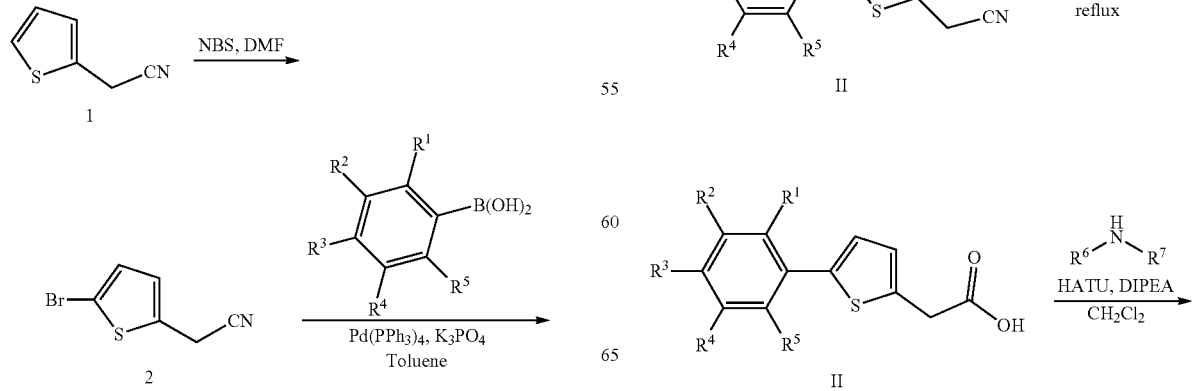

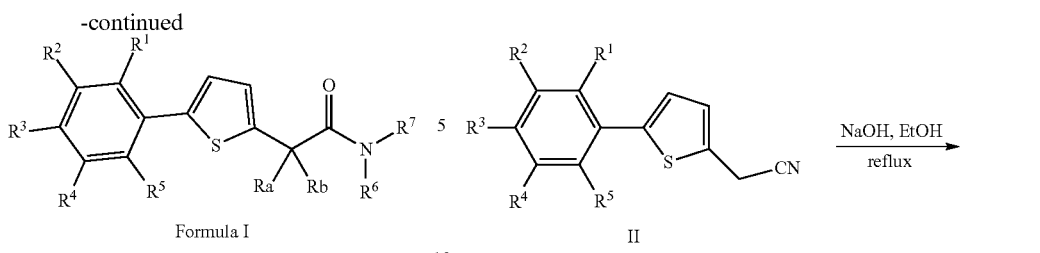

Formula I

Further to the general scheme of preparation, the present invention incorporates all such conventional reaction mechanisms and parameters that would result in the preparation of the disclosed compounds as known through prior art.

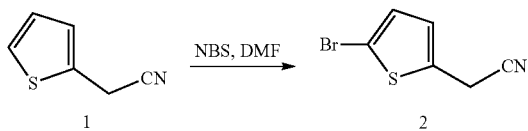

2-(5-Bromothiophen-2-yl)acetonitrile (2): To a stirred solution of 2-(thiophen-2-yl)acetonitrile 1 (15 g, 121.7 mmol) in DMF (110 mL), NBS (22.7 g, 127.8 mmol) was added portion wise for 2 h. The reaction mixture was stirred in the dark under nitrogen for 24 h. Diethyl ether (100 mL) was added to the reaction mixture and washed with water (50 mL) and brine (30 mL). Organic layer was concentrated and purified by column chromatography (silica gel 100-200 mesh, 5% ethyl acetate in pet ether) to afford compound 2 (15 g, 86%) as a pale yellow solid. $^1$H NMR (400 MHz, CDCl$_3$): 6.95; (d, J=4.1, 1H), 6.84; (m, 1H), 3.84; (s, 2H).

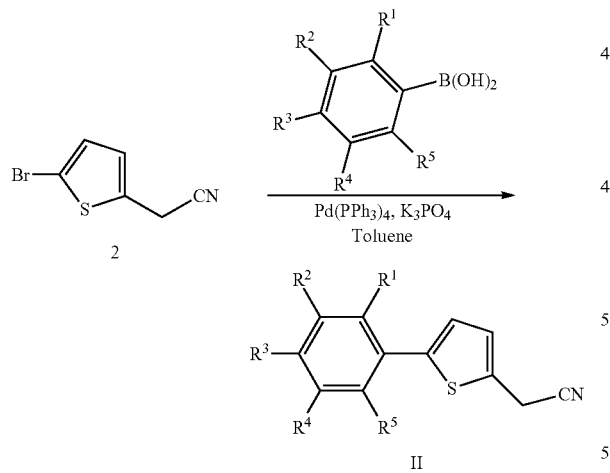

General Procedure A: Synthesis of Compound II: To a stirred solution of compound 2 (2 mmol) in toluene (10 mL), K$_2$CO$_3$ (5 mmol) and boronic acid (4 mmol) were added and purged with argon for 20 min. Pd(PPh$_3$)$_4$ (0.1 mmol) was added and heated at 100° C. for 18 h. Cooled the reaction mixture to room temperature, concentrated and diluted with ethyl acetate (30 mL) washed with water (10 mL) and brine (10 mL). Organic layer was dried over Na$_2$SO$_4$ concentrated and purified by column chromatography to afford compound II.

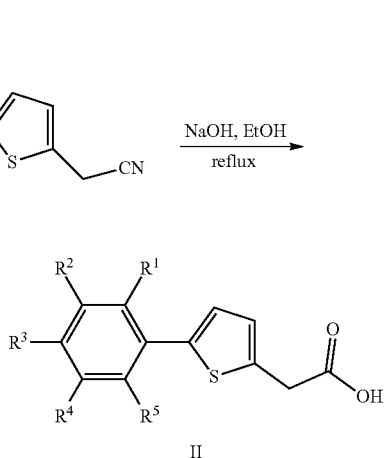

General Procedure B: Synthesis of Compound III: To a stirred solution of compound II (1 mmol) in ethanol (10 mL). NaOH (4 mmol, dissolved in 3 ml of water) was added and refluxed for 4 h. concentrated the reaction mixture acidified to P$^H$~3 with conc. HCl and extracted with ethyl acetate (20 mL×3). Combined the organic fractions dried over Na$_2$SO$_4$ concentrated to give compound III

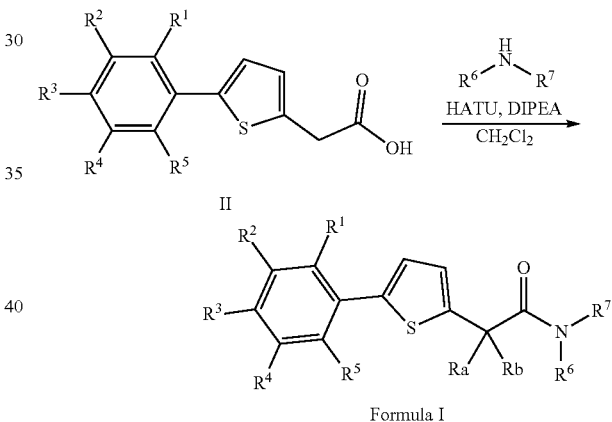

Formula I

General Procedure C: Synthesis of Formula I

To a stirred solution of compound III (1 mmol) in CH$_2$Cl$_2$ (10 mL), HATU (1.1 mmol) and DIPEA (2 mmol) were added at 0° C. followed by Amine (1 mmol) was added and stirred for 20 h at room temperature. Concentrated the reaction mixture diluted with ethyl acetate (20 mL) organic fraction was washed with saturated NaHCO$_3$ (5 mL) followed by brine (10 mL). Organic fraction was dried over Na$_2$SO$_4$ concentrated and purified by column chromatography.

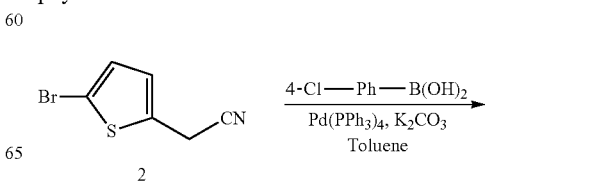

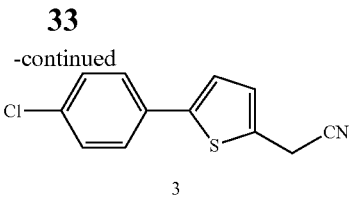

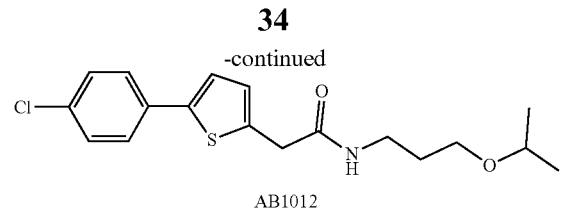

Examples of Compounds and their Preparation 2-(5-(4-Chlorophenyl)thiophen-2-yl)acetonitrile (3): compound 3 (2.3 gm, 50%) synthesized from compound 2 by following general procedure A. $^1$H NMR (400 MHz, DMSO-$d_6$) δ 7.61-7.69; (m, 2H), 7.39-7.51; (m, 3H), 7.09; (d, J=3.42 Hz, 1H), 4.32; (s, 2H).

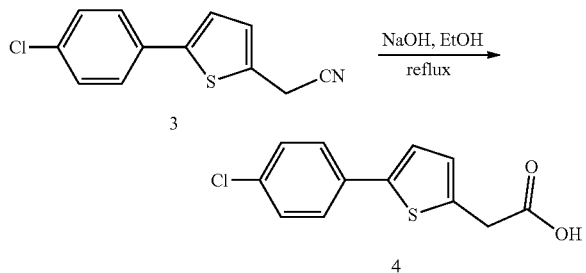

2-(5-(4-chlorophenyl)thiophen-2-yl)acetic acid (4): Compound 4 (1.8 g, 92%) Synthesized from compound 3 by following General procedure B. $^1$H NMR (400 MHz, DMSO-$d_6$) δ 12.64; (brs., 1H), 7.58-7.70; (m, 2H), 7.42-7.49; (m, 2H), 7.34-7.40; (m, 1H), 6.96; (d, J=3.91 Hz, 1H), 3.84; (s, 2H).

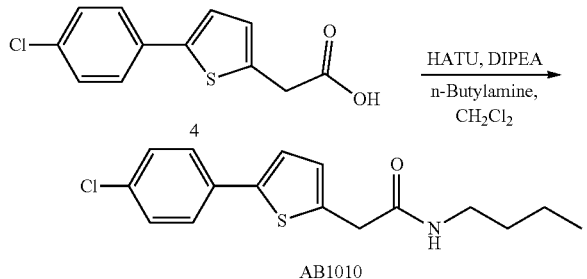

N-butyl-2-(5-(4-chlorophenyl)thiophen-2-yl)acetamide (AB1010): Compound AB1010 (25 mg, 14%) was synthesized from compound 4 by following general procedure C. $^1$H NMR (400 MHz, CDCl$_3$) δ 7.45-7.52; (m, 2H), 7.32-7.40; (m, 2H), 7.06-7.21; (m, 1H), 6.90; (d, J=3.42 Hz, 1H), 5.63; (s, 1H), 3.75; (s, 2H), 3.20-3.31; (m, 2H), 1.38-1.50; (m, 2H), 1.20-1.35; (m, 2H), 0.85-0.96; (m, 3H). MS: 308 (M+H)$^+$.

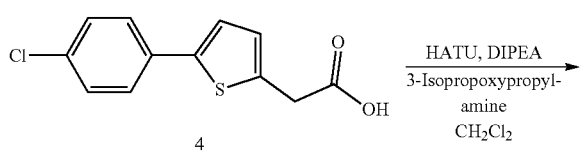

2-(5-(4-Chlorophenyl)thiophen-2-yl)-N-(3-isopropoxypropyl)acetamide (AB1012): Compound AB1012 (103 mg, 50%) was synthesized from compound 4 by following general procedure C. $^1$H NMR (400 MHz, CDCl$_3$) δ 7.44-7.51; (m, J=8.80 Hz, 2H), 7.30-7.35; (m, J=8.31 Hz, 2H), 7.14; (d, J=3.42 Hz, 1H), 6.89; (d, J=3.91 Hz, 1H), 6.33; (brs., 1H), 3.73; (s, 2H), 3.43-3.50; (m, 3H), 3.38; (q, J=5.87 Hz, 2H), 1.68-1.77; (m, 2H), 1.05; (d, J=5.87 Hz, 6H). MS: 352 (M+H)$^+$.

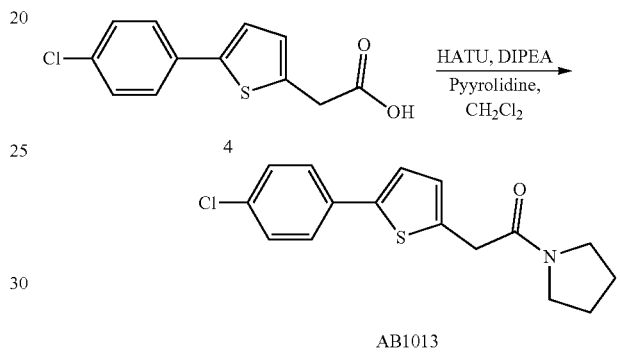

2-(5-(4-Chlorophenyl)thiophen-2-yl)-1-(pyrrolidin-1-yl)ethan-1-one (AB1013): Compound AB1013 (105 mg, 58%) was synthesized from compound 4 by following general procedure C. $^1$H NMR (400 MHz, CDCl$_3$) δ 7.45-7.52; (m, J=8.31 Hz, 2H), 7.28-7.34; (m, J=8.31 Hz, 2H), 7.12; (d, J=3.42 Hz, 1H), 6.88; (d, J=3.42 Hz, 1H), 3.83; (s, 2H), 3.52; (t, J=6.85 Hz, 4H), 1.97; (quin, J=6.85 Hz, 2H), 1.87; (quin, J=6.73 Hz, 2H). MS: 306 (M+H)$^+$.

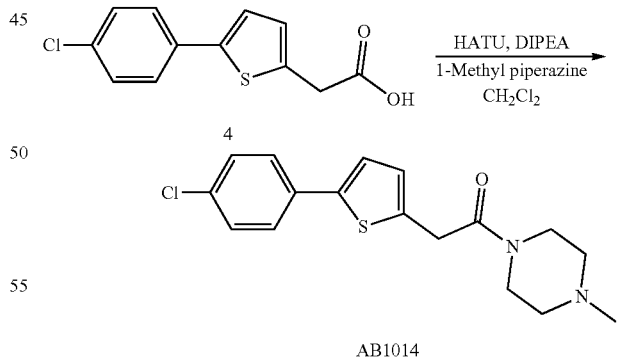

2-(5-(4-Chlorophenyl)thiophen-2-yl)-1-(4-methylpiperazin-1-yl)ethan-1-one (AB1014): Compound AB1014 (93 mg, 47%) was synthesized from compound 4 by following general procedure C. $^1$H NMR (400 MHz, CDCl$_3$) δ 7.45-7.54; (m, 2H), 7.30-7.37; (m, 2H), 7.12; (d, J=3.91 Hz, 1H), 6.85; (d, J=3.42 Hz, 1H), 3.90; (s, 2H), 3.64-3.72; (m, 2H), 3.51-3.62; (m, 2H), 2.38; (td, J=5.07, 15.28 Hz, 4H), 2.29; (s, 3H). MS; 335 (M+H)$^+$. MS: 335 (M+H)$^+$. HPLC: 98.9%

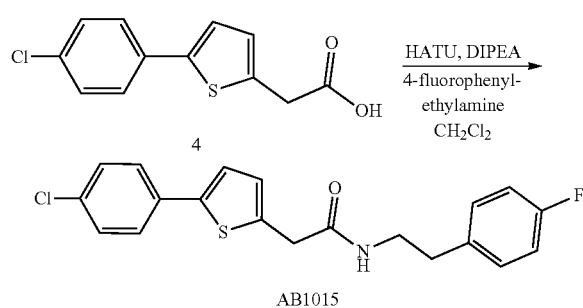

2-(5-(4-chlorophenyl)thiophen-2-yl)-N-(4-fluorophenethyl)acetamide (AB1015): Compound AB1015 (80 mg, 33%) was synthesized from compound 4 by following general procedure C. $^1$H NMR (400 MHz, CDCl$_3$) δ 7.45-7.50; (m, 2H), 7.33-7.38; (m, 2H), 7.12; (d, J=3.91 Hz, 1H), 7.04; (dd, J=5.38, 8.31 Hz, 2H), 6.90; (t, J=8.56 Hz, 2H), 6.81; (d, J=3.42 Hz, 1H), 5.62; (br. s., 1H), 3.72; (s, 2H), 3.48; (q, J=6.52 Hz, 2H), 2.75; (t, J=6.85 Hz, 2H). MS: 374 (M+H)$^+$.

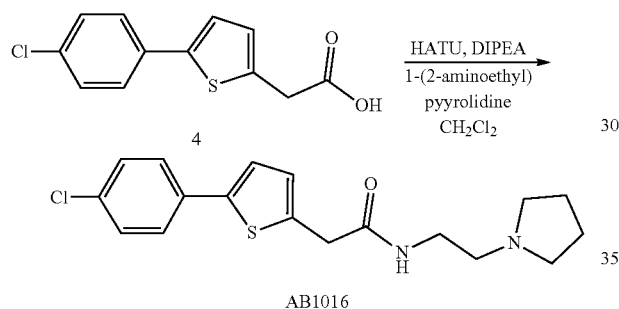

2-(5-(4-Chlorophenyl)thiophen-2-yl)-N-(2-(pyrrolidin-1-yl)ethyl)acetamide (AB1016): Compound AB1016 (80 mg, 38%) was synthesized from compound 4 by following general procedure C. $^1$H NMR (400 MHz, CDCl$_3$) δ 7.45-7.51; (m, 2H), 7.31-7.37; (m, 2H), 7.17; (d, J=3.42 Hz, 1H), 6.91; (d, J=3.91 Hz, 1H), 6.42; (brs., 1H), 3.77; (s, 2H), 3.52-3.61; (m, 4H), 3.34; (q, J=5.87 Hz, 2H), 2.48; (t, J=6.11 Hz, 2H), 2.36-2.43; (m, 4H). MS: 349 (M+H)$^+$.

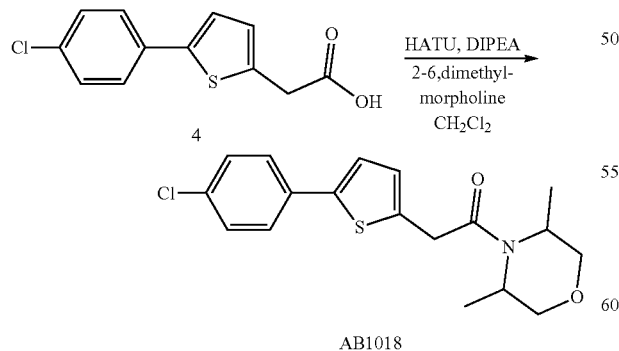

2-(5-(4-chlorophenyl)thiophen-2-yl)-1-(3,5-dimethylmorpholino)ethan-1-one (AB1018): Compound AB1018 (75 mg, 36%) was synthesized from compound 4 by following general procedure C. $^1$H NMR (400 MHz, CDCl$_3$) δ 7.45-7.51; (m, 2H), 7.30-7.35; (m, 2H), 7.13; (d, J=3.91 Hz, 1H), 6.85; (d, J=3.91 Hz, 1H), 4.48; (d, J=13.21 Hz, 1H), 3.90; (d, J=3.91 Hz, 2H), 3.70; (d, J=13.21 Hz, 1H), 3.35-3.60; (m, 2H), 2.84; (dd, J=10.76, 13.21 Hz, 1H), 2.36; (dd, J=10.76, 13.21 Hz, 1H), 1.18; (t, J=7.09 Hz, 6H). MS: 350 (M+H)$^+$.

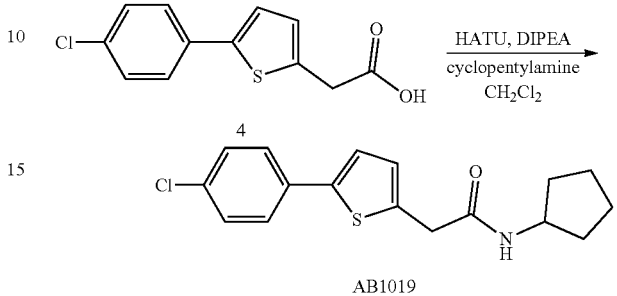

2-(5-(4-Chlorophenyl)thiophen-2-yl)-N-cyclopentylacetamide (AB1019): Compound AB1019 (79 mg, 42%) was synthesized from compound 4 by following general procedure C. $^1$H NMR (400 MHz, CDCl$_3$) δ 7.46-7.52; (m, 2H), 7.30-7.37; (m, 2H), 7.16; (d, J=3.58 Hz, 1H), 6.88; (d, J=3.58 Hz, 1H), 5.58; (brs., 1H), 4.08-4.33; (m, 1H), 3.73; (s, 2H), 1.87-2.09; (m, 2H), 1.46-1.75; (m, 4H), 1.11-1.41; (m, 2H). MS: 320 (M+H)$^+$.

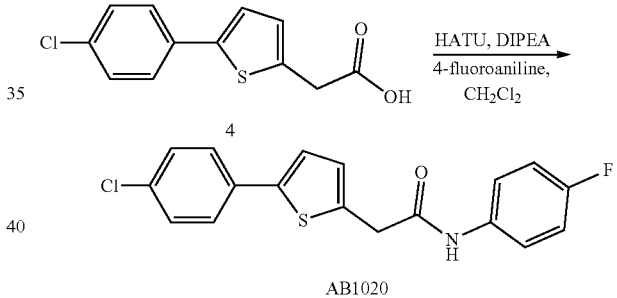

2-(5-(4-Chlorophenyl)thiophen-2-yl)-N-(4-fluorophenyl)acetamide (AB1020): Compound AB1020 (104 mg, 51%) was synthesized from compound 4 by following general procedure C. $^1$H NMR (400 MHz, CDCl$_3$) δ 7.47-7.54; (m, 2H), 7.39-7.45; (m, 2H), 7.32-7.38; (m, 2H), 7.21; (d, J=3.58 Hz, 1H), 6.92-7.05; (m, 3H), 3.93; (s, 2H). MS: 344; (M−H).

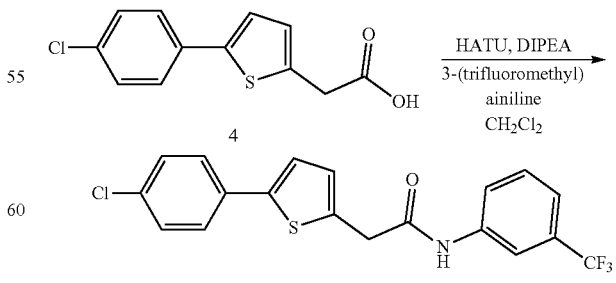

2-(5-(4-Chlorophenyl)thiophen-2-yl)-N-(3-(trifluoromethyl)phenyl)acetamide (AB1021): Compound AB1021

(120 mg, 51%) was synthesized from compound 4 by following general procedure C. $^1$H NMR (400 MHz, CDCl$_3$) δ 7.75; (s, 1H), 7.69; (d, J=8.19 Hz, 1H), 7.47-7.55; (m, 3H), 7.40-7.47; (m, 1H), 7.31-7.40; (m, 3H), 7.22; (d, J=3.58 Hz, 1H), 7.01; (d, J=3.58 Hz, 1H), 3.96; (s, 2H). MS: 394; (M−H).

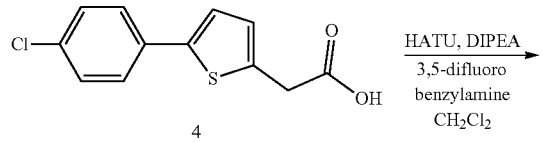

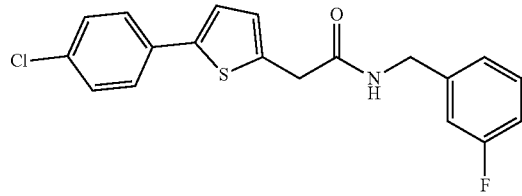

AB1022

2-(5-(4-Chlorophenyl)thiophen-2-yl)-N-(3,5-difluorobenzyl)acetamide (AB1022): Compound AB1022 (103 mg, 46%) was synthesized from compound 4 by following general procedure C. $^1$H NMR (400 MHz, CDCl$_3$) δ 7.45-7.53; (m, 2H), 7.32-7.41; (m, 2H), 7.17; (d, J=3.58 Hz, 1H), 6.93; (d, J=3.58 Hz, 1H), 6.62-6.81; (m, 3H), 4.43; (d, J=6.14 Hz, 2H), 3.79-3.91; (m, 2H). MS: 376; (M−H).

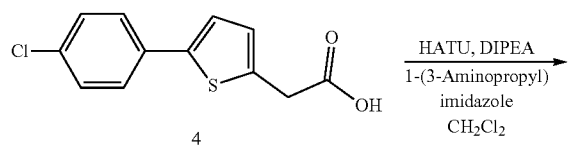

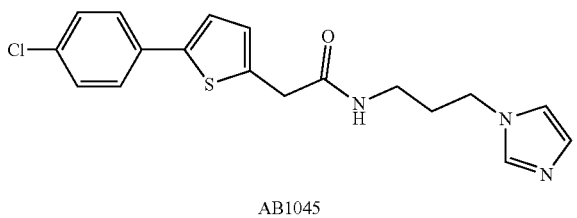

AB1045

N-(3-(1H-Imidazol-1-yl)propyl)-2-(5-(4-chlorophenyl)thiophen-2-yl)acetamide (AB1045): Compound AB1045 (140 mg, 66%) was synthesized from compound 4 by following general procedure C. $^1$H NMR (400 MHz, CDCl$_3$) δ 7.49-7.47; (m, 3H), 7.34; (d, J=8.4 Hz, 2H), 7.16; (d, J=3.3 Hz, 1H), 7.05; (s, 1H), 6.91; (d, J=7.4 Hz, 2H), 5.90; (s, 1H), 3.97; (t, J=6.9 Hz, 2H), 3.75; (s, 2H), 3.27; (q, J=6.5 Hz, 2H), 2.02-1.85; (m, 2H); MS; 360 (M+H)$^+$. HPLC: 98.3%

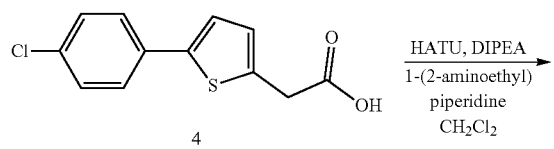

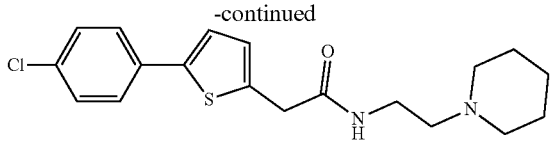

AB1047

2-(5-(4-Chlorophenyl)thiophen-2-yl)-N-(2-(piperidin-1-yl)ethyl)acetamide (AB1047): Compound AB1047 (76 mg, 36%) was synthesized from compound 4 by following general procedure C. $^1$H NMR (400 MHz, CDCl$_3$) δ 7.48; (d, J=8.6 Hz, 2H), 7.33; (d, J=8.4 Hz, 2H), 7.15; (d, J=3.6 Hz, 1H), 6.93; (d, J=3.4 Hz, 2H), 3.77; (s, 2H), 3.39; (q, J=5.2 Hz, 2H), 2.56; (s, 2H), 2.48; (brs, 4H), 1.55; (s, 4H), 1.41; (d, J=5.7 Hz, 2H). MS: 363 (M+H)$^+$.

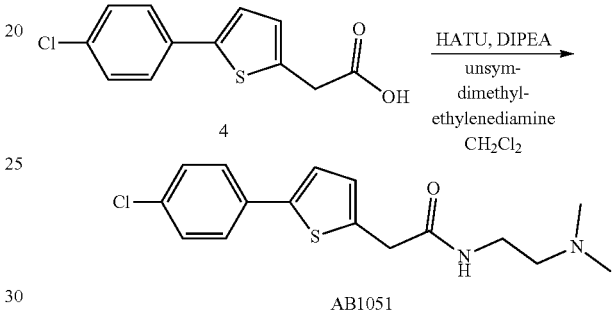

AB1051

2-(5-(4-Chlorophenyl)thiophen-2-yl)-N-(2-(dimethylamino)ethyl)acetamide (AB1051): Compound AB1051 (40 mg, 21%) was synthesized from compound 4 by following general procedure C. $^1$H NMR (400 MHz, CDCl$_3$) δ 7.49-7.46; (m, 2H), 7.33-7.31; (m, 2H), 7.14; (d, J=3.4 Hz, 1H), 6.90; (d, J=3.6 Hz, 1H), 6.50; (brs., 1H), 3.75; (s, 2H), 3.39; (q, J=5.7 Hz, 2H), 2.53; (t, J=5.9 Hz, 2H), 2.30; (s, 6H). MS: 323 (M+H)$^+$.

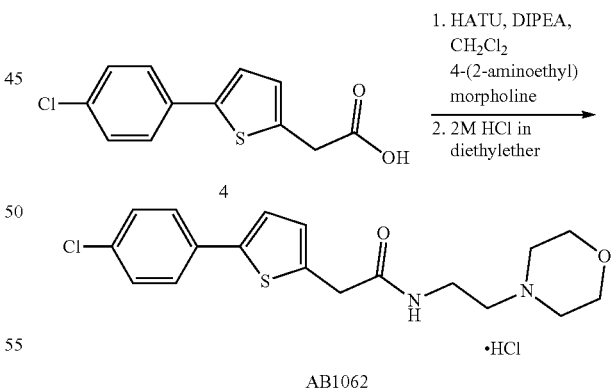

AB1062

2-(5-(4-chlorophenyl)thiophen-2-yl)-N-(2-morpholinoethyl)acetamide hydrochloride (AB1062): To a stirred solution of compound 4 (150 mg, 0.59 mmol) in CH$_2$Cl$_2$ (5 mL), HATU (270 mg, 0.71 mmol) and DIPEA (0.2 mL) were added at 0° C. followed by 4-(2-aminoethyl)morpholine (94 μL, 0.71 mmol) added and stirred for 20 h at room temperature. Concentrated the reaction mixture diluted with ethyl acetate (20 mL) organic fraction was washed with saturated NaHCO$_3$ (5 mL) followed by brine (10 mL).

Organic fraction was dried over Na₂SO₄ concentrated and purified by column chromatography (silica gel 100-200 mesh, 5% MeOH in CH₂Cl₂) to afford compound 2-(5-(4-chlorophenyl)thiophen-2-yl)-N-(2-morpholinoethyl)acetamide (122 mg, 56%) as off white color solid. ¹H NMR (500 MHz, CDCl₃) δ 7.43-7.55; (m, 2H), 7.29-7.40; (m, 2H), 7.14; (d, J=3.91 Hz, 1H), 6.89; (d, J=3.42 Hz, 1H), 3.75; (s, 2H), 3.36; (q, J=5.87 Hz, 2H), 2.59; (t, J=6.11 Hz, 2H), 2.48; (brs., 4H), 1.71; (td, J=3.24, 6.73 Hz, 4H). 55 mg of this compound was treated with 2M HCl in diethyl ether (3 mL) for 3 h. Concentrated the reaction mixture to give AB1062 in quantitative yield. ¹NMR (400 MHz, DMSO-d₆) δ 11.02; (s, 1H), 8.59; (t, J=5.5 Hz, 1H), 7.62; (d, J=8.6 Hz, 2H), 7.45; (d, J=8.6 Hz, 2H), 7.37; (d, J=3.6 Hz, 1H), 6.95; (d, J=3.6 Hz, 1H), 3.94; (m, 2H), 3.82; (t, J=11.7 Hz, 2H), 3.69; (s, 2H), 3.50; (q, J=6.1 Hz, 2H), 3.45; (d, J=12.1 Hz, 2H), 3.18; (dd, J=11.3 Hz, 5.9 Hz, 2H), 3.11-3.04; (m, 2H); MS: 365 (M+H)⁺. HPLC: 97.7%

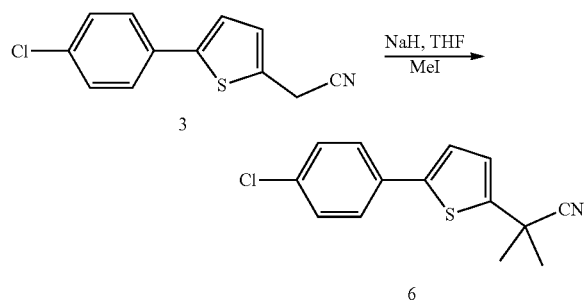

2-(5-(4-chlorophenyl)thiophen-2-yl)-2-methylpropanenitrile (6): To a stirred solution of compound 4 (1.8 gm, 7.7 mmol) in THF (30 mL), NaH (302 mg, 16.9 mmol, 60% in mineral oil) was added portion wise at 0° C. followed by MeI (1.93 mL, 30.8 mmol) was added and stirred for 3 h. Reaction was quenched with ice cold water (15 mL) and extracted with ethyl acetate (50 mL×3). Organic layer was dried over Na₂SO₄ concentrated and purified by column chromatography (silica gel 100-200 mesh, 6-8% ethyl acetate in pet ether) to afford compound 6 (1.7 gm, 84%) as yellow color solid. ¹H NMR (500 MHz, CDCl₃) δ 7.48; (d, J=8.6 Hz, 2H), 7.35; (d, J=8.6 Hz, 1H), 7.13; (d, J=3.6 Hz, 1H), 7.07; (d, J=3.6 Hz, 1H), 1.82; (s, 6H).

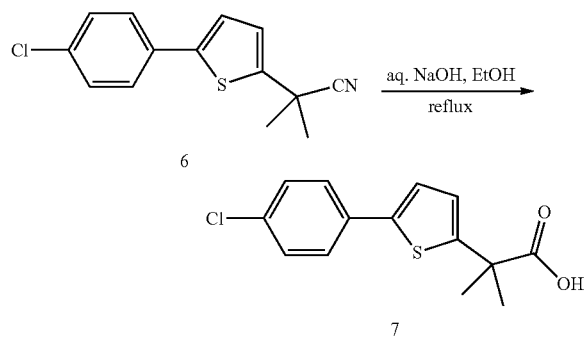

2-(5-(4-Chlorophenyl)thiophen-2-yl)-2-methylpropanoic acid (7): Compound 7 (700 mg, 38%) was synthesized from compound 6 by following general procedure B. ¹H NMR (DMSO-d₆, 500 MHz): δ 12.66; (s, 1H), 7.64; (d, J=8.3 Hz, 2H), 7.45; (d, J=9.0, 2H), 7.38; (d, J=4.1 Hz, 1H), 7.00; (d, J=3.4 Hz, 1H), 1.57; (s, 6H).

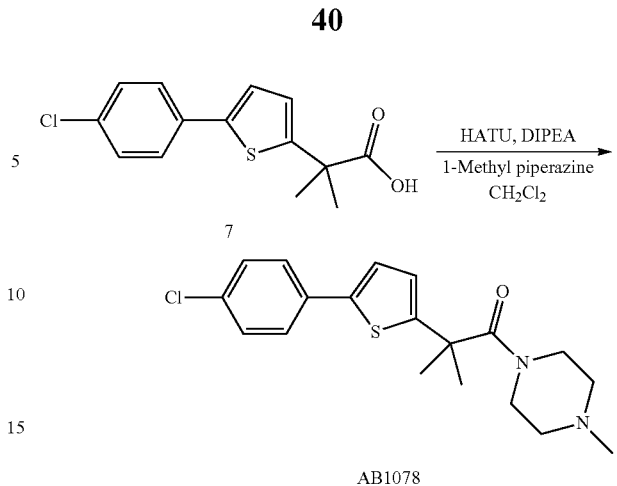

2-(5-(4-Chlorophenyl)thiophen-2-yl)-2-methyl-1-(4-methylpiperazin-1-yl)propan-1-one (AB1078): Compound AB1078 (100 mg, 52%) was synthesized from compound 4 by following general procedure C. ¹H NMR (500 MHz, CDCl₃) δ 7.49; (d, J=8.4 Hz, 2H), 7.33; (d, J=8.4 Hz, 1H), 7.13; (d, J=3.6 Hz, 1H), 6.77; (d, J=3.6 Hz, 1H), 3.49; (brs., 4H), 2.26; (brs., 4H), 1.63; (s, 6H). MS: 363 (M+H)⁺.

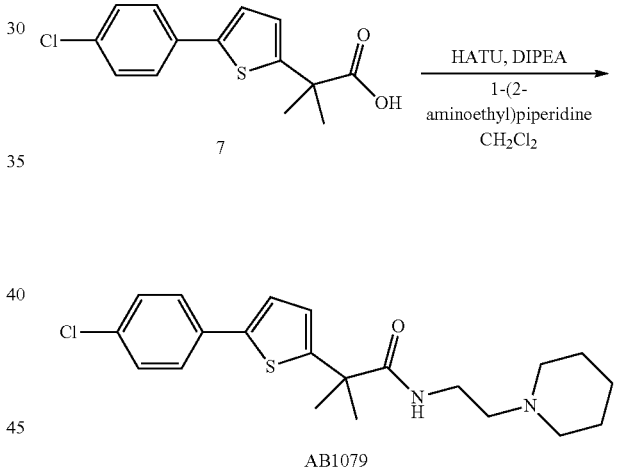

2-(5-(4-Chlorophenyl)thiophen-2-yl)-2-methyl-N-(2-(piperidin-1-yl)ethyl)propanamide (AB1079): Compound AB1079 (85 mg, 41%) was synthesized from compound 4 by following general procedure C. ¹H NMR (500 MHz, CDCl₃) δ 7.47 (d, J=8.1 Hz, 2H), 7.32; (d, J=8.3 Hz, 2H), 7.15; (d, J=3.4 Hz, 1H), 7.09; (s, 1H), 7.03; (d, J=3.4 Hz, 1H), 3.55; (d, J=3.4 Hz, 2H), 3.18; (brs., 4H), 3.0; (brs., 2H), 1.82; (6H), 1.69; (s, 6H); MS; 391 (M+H)⁺. MS: 391 (M+H)⁺. 98.9%

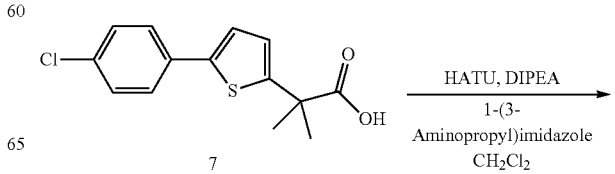

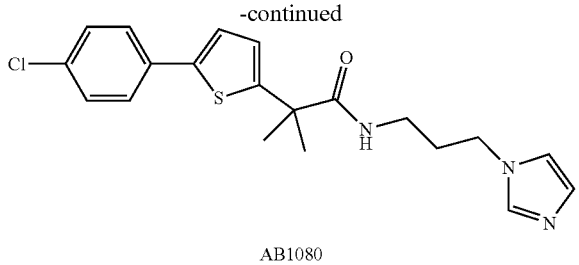

AB1080

N-(3-(1H-Imidazol-1-yl)propyl)-2-(5-(4-chlorophenyl)thiophen-2-yl)-2-methylpropanamide (AB1080): Compound AB1080 (83 mg, 40%) was synthesized from compound 7 by following general procedure C. $^1$H NMR (500 MHz, CDCl$_3$) δ 7.53; (s, 1H), 7.49; (d, J=8.4 Hz, 2H), 7.34; (d, J=8.4 Hz, 2H), 7.18; (d, J=3.6 Hz, 1H), 7.04; (s, 1H), 6.96; (d, J=3.4 Hz, 1H), 6.90; (s, 1H), 5.71; (brs., 1H), 3.92; (t, J=6.9 Hz, 2H), 3.19; (q, J=6.5 Hz, 2H), 1.97-1.93; (m, 2H), 1.66; (s, 6H). MS: 388 (M+H)$^+$.

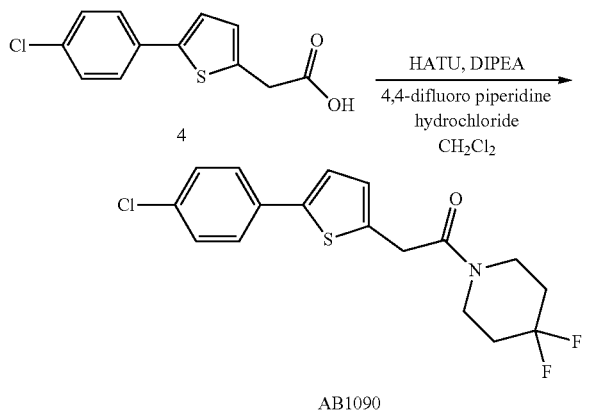

AB1090

2-(5-(4-chlorophenyl)thiophen-2-yl)-1-(4,4-difluoropiperidin-1-yl)ethan-1-one (AB1090): Compound AB1090 (118 mg, 60%) was synthesized from compound 4 by following general procedure C. $^1$H NMR (500 MHz, CDCl$_3$) δ 7.48; (d, J=8.6 Hz, 2H), 7.33; (d, J=8.6 Hz, 2H), 7.13; (d, J=3.6 Hz, 1H), 6.86; (d, J=3.6 Hz, 1H), 3.93; (s, 2H), 3.77; (t, J=6.9 Hz, 2H), 3.64; (t, J=6.9 Hz, 2H), 1.99-1.86; (m, 4H). MS: 356 (M+H)$^+$.

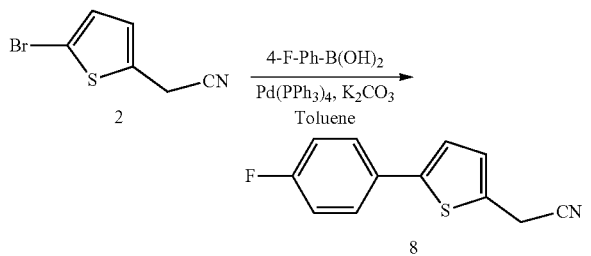

2-(5-(4-fluorophenyl)thiophen-2-yl)acetonitrile) (8): Compound 8 (1.5 gm, 71%) was synthesized from compound 2 by following general procedure A. $^1$H NMR (400 MHz, DMSO-d$_6$) δ 7.52-7.49; (m, 2H), 7.09-7.05; (m, 4H), 3.91; (s, 2H).

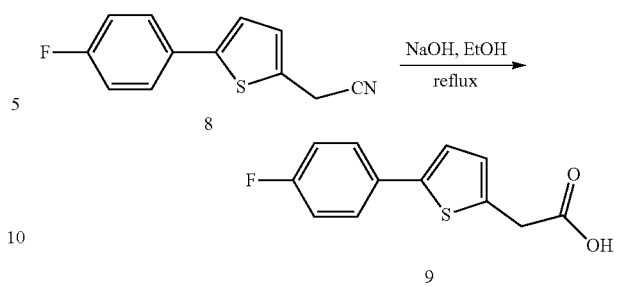

2-(5-(4-fluorophenyl)thiophen-2-yl)acetic acid (9): Compound 9 (1.45 g) was synthesized from compound 8 by following general procedure B. $^1$H NMR (500 MHz, CDCl$_3$) δ 7.53-7.49; (m, 2H), 7.09-7.03; (m, 3H), 6.92; (d, J=3.6 Hz, 1H), 3.88; (s, 2H).

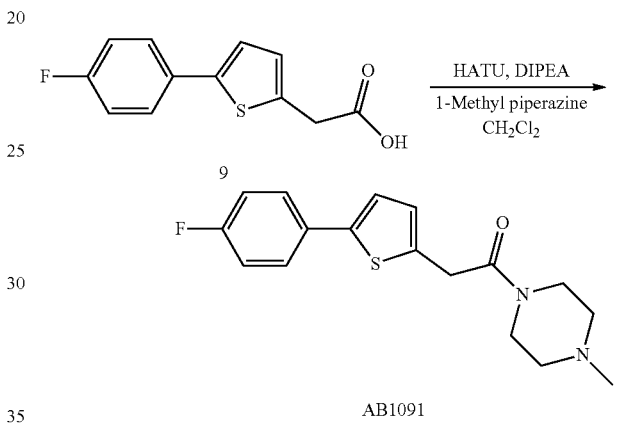

AB1091

2-(5-(4-fluorophenyl)thiophen-2-yl)-1-(4-methylpiperazin-1-yl)ethan-1-one (AB1091): Compound AB1091 (78 mg, 48%) was synthesized from compound 9 by following general procedure C. $^1$H NMR (500 MHz, CDCl$_3$) δ 7.53-5.30; (m, 2H), 7.07-7.03; (m, 3H), 6.84; (d, J=3.6 Hz, 1H), 3.90; (s, 2H), 3.68; (t, J=4.9 Hz, 2H), 3.56; (t, J=5.1 Hz, 2H), 2.40; (t, J=5.2 Hz, 2H), 2.36; (t, J=5.0 Hz, 2H), 2.29; (s, 3H). MS: 319 (M+H)$^+$.

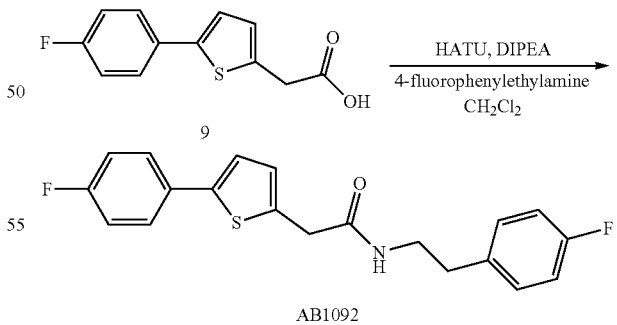

AB1092

N-(4-fluorophenethyl)-2-(5-(4-fluorophenyl)thiophen-2-yl)acetamideAB (1092): Compound AB1092 (110 mg, 60%) was synthesized from compound 9 by following general procedure C. $^1$H NMR (CDCl$_3$, 500 MHz) δ 7.52-7.49; (m, 2H), 7.49-7.04; (m, 5H), 6.92-6.88; (2H, m), 6.80; (d, J=3.6 Hz, 1H), 5.62; (s, 1H), 3.72; (s, 2H), 3.48; (q, J=6.5 Hz, 2H), 2.75; (t, J=6.9 Hz, 2H). MS: 358 (M+H)$^+$.

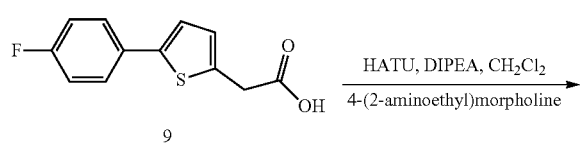

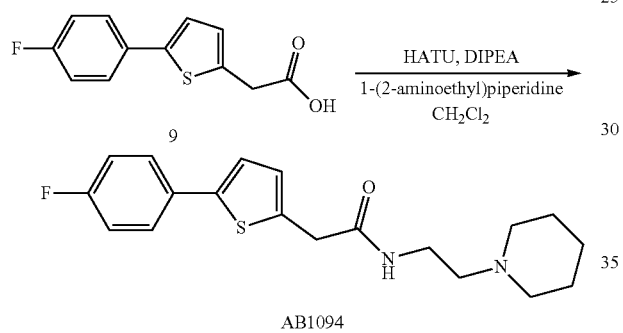

2-(5-(4-fluorophenyl)thiophen-2-yl)-N-(2-morpholino-ethyl)acetamide AB (1093): Compound AB1093 (140 mg, 79%) was synthesized from compound 9 by following general procedure C. $^1$H NMR (CDCl$_3$, 500 MHz): δ 7.53-7.50; (m, 2H), 7.13; (d, J=3.6 Hz, 1H), 7.08-7.05; (m, 2H), 6.91; (d, J=3.6 Hz, 1H), 6.37; (s, 1H), 3.77; (s, 2H), 3.55; (t, J=4.4 Hz, 4H), 3.33; (q, J=5.6 Hz, 2H), 2.45; (t, J=6.0 Hz, 2H), 2.37; (t, J=4.0 Hz, 4H). MS: 349 (M+H)$^+$.

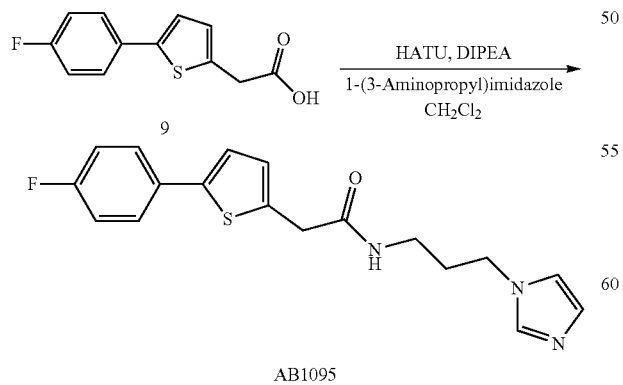

2-(5-(4-fluorophenyl)thiophen-2-yl)-N-(2-(piperidin-1-yl)ethyl)acetamide (AB1094): Compound AB1094 (31 mg, 10%) was synthesized from compound 9 by following general procedure C. $^1$H NMR (CDCl$_3$, 500 MHz): δ 7.53-7.50; (m, 2H), 7.11; (d, J=3.4 Hz, 1H), 7.11-7.04; (m, 2H), 6.90; (d, J=3.6 Hz, 1H), 6.64; (s, 1H), 3.76; (s, 2H), 3.32; (q, J=5.6 Hz, 2H), 2.44; (t, J=6.0 Hz, 2H), 2.34; (s, 4H), 1.46-1.42; (m, 4H), 1.35; (d, J 5.3, 2H). MS: 347 (M+H)$^+$.

N-(3-(1H-imidazol-1-yl)propyl)-2-(5-(4-fluorophenyl)thiophen-2-yl)acetamide AB(1095): Compound AB1095 (35 mg, 12%) was synthesized from compound 9 by following general procedure C. $^1$H NMR (CDCl$_3$, 500 MHz): δ 7.52; (dd, J 8.6 Hz, 2H), 7.45; (s, 1H), 7.11-7.04; (m, 4H), 6.90-6.88; (m, 2H), 5.94; (s. 1H), 3.96; (t, J=6.9 Hz, 2H), 3.75; (s, 2H), 3.26; (q, J=6.4 Hz, 2H), 2.01-1.96; (m, 2H). MS: 344 (M+H)$^+$.

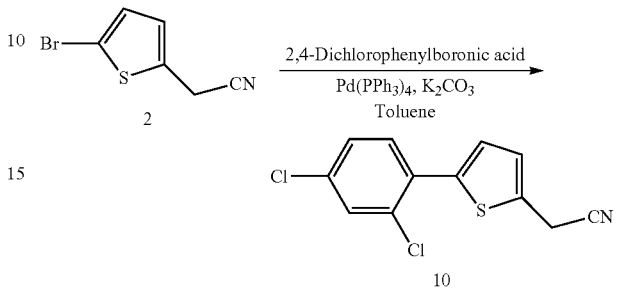

2-(5-(2,4-dichlorophenyl)thiophen-2-yl)acetonitrile (10): compound 10 (2.4 gm, 70%) synthesized from compound 2 by following general procedure A. $^1$H NMR (DMSO-d$_6$, 500 MHz): δ 7.76; (dd, J=12.1 Hz, 10.0 Hz, 1H), 7.67; (t, J=7.2 Hz, 1H), 7.51-7.48; (m, 1H), 7.37; (q, J=3.4 Hz, 1H), 7.14; (d, J=3.4 Hz, 1H), 4.36; (s, 2H).

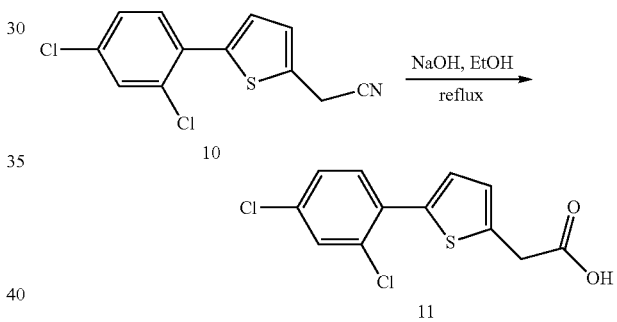

2-(5-(2,4-dichlorophenyl)thiophen-2-yl)acetic acid (11): Compound 11 (2 g, 81%) Synthesized from compound 10 by following General procedure B. $^1$H NMR (DMSO-d$_6$, 500 MHz): δ 12.65; (bs, 1H), 7.74; (s, 1H), 7.64; (d, J=8.3 Hz, 1H), 7.49; (dd, J=9.0 Hz, 2.1 Hz, 1H), 7.32; (d, J=3.4 Hz, 1H), 7.01; (d, J=3.4 Hz, 1H), 3.88; (s, 2H).

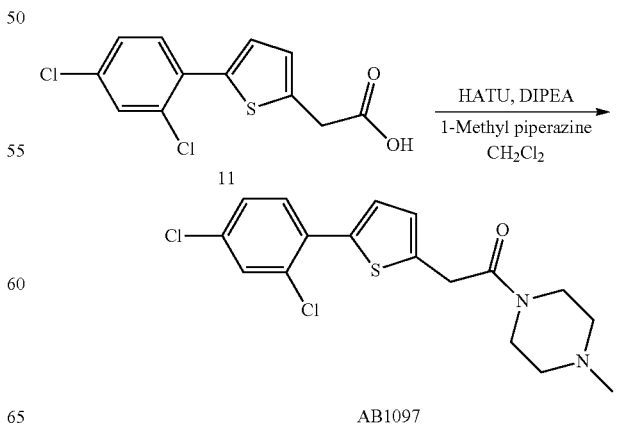

2-(5-(2,4-dichlorophenyl)thiophen-2-yl)-1-(4-methylpiperazin-1-yl)ethan-1-one (AB1097): Compound AB1097 (62 mg, 24%) was synthesized from compound 11 by following general procedure C. δ $^1$H NMR (DMSO-d$_6$, 500 MHz): δ 7.73; (d, J=2.8 Hz, 1H), 7.63; (d, J=8.3 Hz, 1H), 7.48; (dd, J=8.3 Hz, 2.1 Hz, 1H), 7.31; (d, J=3.4 Hz, 1H), 6.97; (d, J=3.4 Hz, 1H), 4.00; (s, 2H), 3.53; (t, J=4.8 Hz, 2H), 3.47; (s, 2H), 2.27; (t, J=5.9 Hz, 4H), 2.17; (s, 3H). MS: 369 (M+H)$^+$.

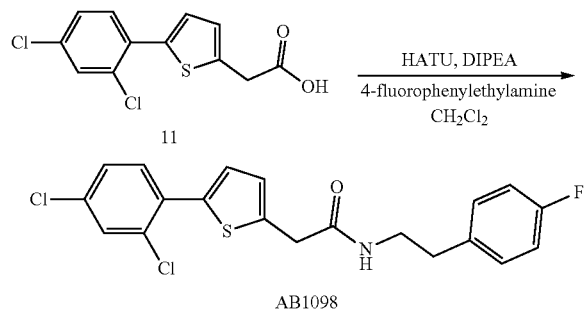

2-(5-(2,4-dichlorophenyl)thiophen-2-yl)-N-(4-fluorophenethyl)acetamide (AB1098): Compound AB1098 (61 mg, 21%) was synthesized from compound 11 by following general procedure C. $^1$H NMR (CDCl$_3$, 500 MHz): δ 7.55-7.52; (1H, m), 7.41; (d, J=8.3, 1H), 7.30-7.27; (1H, m), 7.24-7.20; (1H, m), 7.07-7.00; (2H, m), 6.94; (q, J=8.6 Hz, 2H), 6.86; (dd, J=13.8 Hz, 3.4 Hz, 1H), 5.64; (1H, s), 3.75; (d, J=12.1 Hz, 2H), 3.51-3.43; (2H, m), 2.77-2.71; (2H, m). MS: 408 (M+H)$^+$.

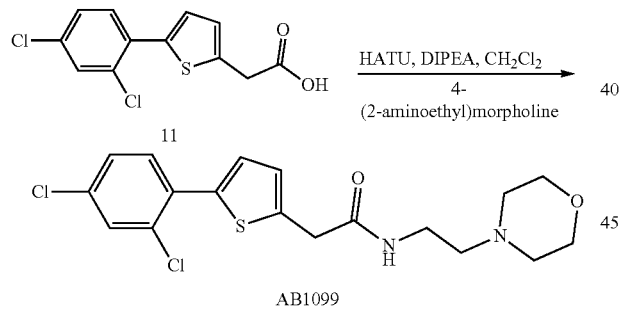

2-(5-(2,4-dichlorophenyl)thiophen-2-yl)-N-(2-morpholinoethyl)acetamideAB (1099): Compound AB1099 (4.5 g, 82%) was synthesized from compound 11 by following general procedure C. $^1$H NMR (CDCl$_3$, 500 MHz); δ 7.49 (d, J=2.1 Hz, 1H), 7.43; (d, J=9.0, 1H), 7.28; (d, J=2.1 Hz, 1H), 7.25; (1H, s), 6.96; (d, J=3.4 Hz, 1H), 6.39; (1H, s), 3.80; (2H, s), 3.60; (t, J=4.5 Hz, 4H), 3.36; (q, J=5.5 Hz, 2H), 2.50; (t, J=5.9 Hz, 2H), 2.43; (4H, s). MS: 399 (M+H)$^+$. HPLC: 99.2%.

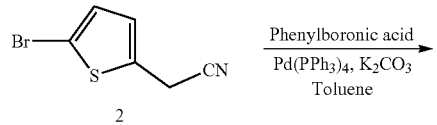

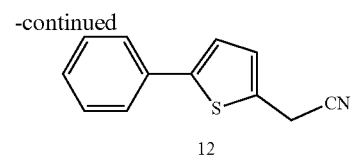

2-(5-phenylthiophen-2-yl)acetonitrile (12): compound 12 (1.6 gm) synthesized from compound 2 by following general procedure A. $^1$H NMR (DMSO-d$_6$, 500 MHz): δ 7.56-7.54; (m, 2H), 7.40-7.32; (m, 2H), 7.31-7.28; (m, 1H), 7.17-7.16; (m, 1H), 7.03-7.02; (m, 1H), 3.92; (s, 2H).

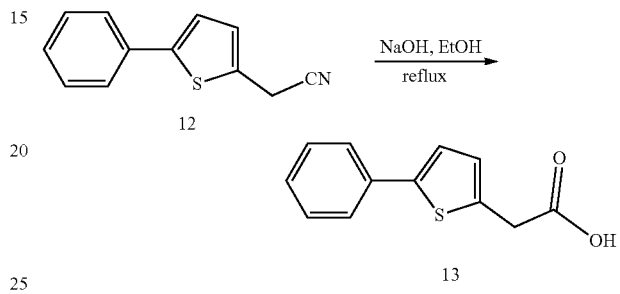

2-(5-phenylthiophen-2-yl)acetic acid (13): Compound 13 (1.3 g) Synthesized from compound 13 by following General procedure B. $^1$H NMR (DMSO-d$_6$, 500 MHz): δ 12.61; (bs, 1H), 7.61-7.59; (m, 2H), 7.41-7.38; (m, 2H), 7.34; (d, J=3.4 Hz, 1H), 7.30-7.27; (m, 1H), 6.95; (d, J=3.4 Hz, 1H), 3.83; (s, 2H).

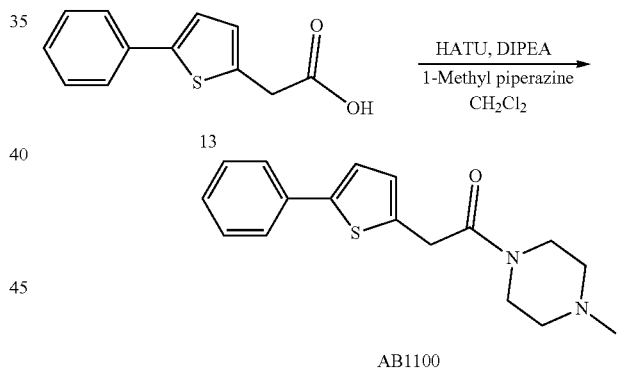

1-(4-methylpiperazin-1-yl)-2-(5-phenylthiophen-2-yl)ethan-1-one (AB1100): Compound AB1100 (65 mg, 23%) was synthesized from compound 13 by following general procedure C. $^1$H NMR (CDCl$_3$, 500 MHz): δ 7.57-7.55; (m, 2H), 7.37-7.34; (m, 2H), 7.27; (t, J=1.1 Hz, 1H), 7.15; (d, J=3.6 Hz, 1H), 6.86; (dd, J=3.6 Hz, 0.9 Hz, 1H), 3.90; (d, J=0.7 Hz, 2H), 3.68; (t, J=4.9 Hz, 2H), 3.55; (t, J=5.1 Hz, 2H), 2.39; (t, J=5.2 Hz, 2H), 2.34; (t, J=5.1 Hz, 2H), 2.28; (s, 3H). MS: 301 (M+H)$^+$.

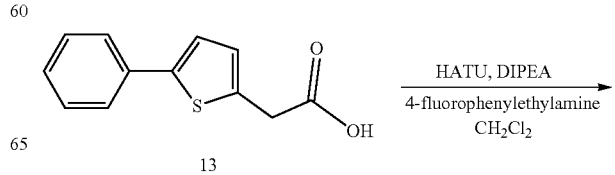

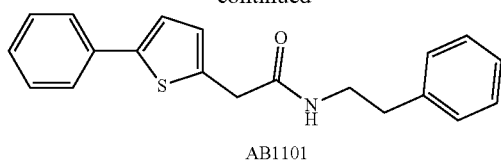

AB1101

N-(4-fluorophenethyl)-2-(5-phenylthiophen-2-yl)acetamide (AB1101): Compound AB1101 (125 mg, 40%) was synthesized from compound 13 by following general procedure C. $^1$H NMR (CDCl$_3$, 500 MHz): δ 7.55; (d, J=7.3 Hz, 2H), 7.39; (t, J=7.3 Hz, 2H), 7.30; (t, J=6.82 Hz, 1H), 7.15; (d, J=3.4 Hz, 1H), 7.04; (q, J=5.3 Hz, 2.9 Hz, 2H), 6.90; (t, J=8.78 Hz, 2H), 6.80; (d, J=3.7 Hz, 1H), 3.79; (s, 2H), 3.47; (q, J=6.3 Hz, 2H), 2.74; (t, J=6.82 Hz, 2H). MS: 340 (M+H)$^+$.

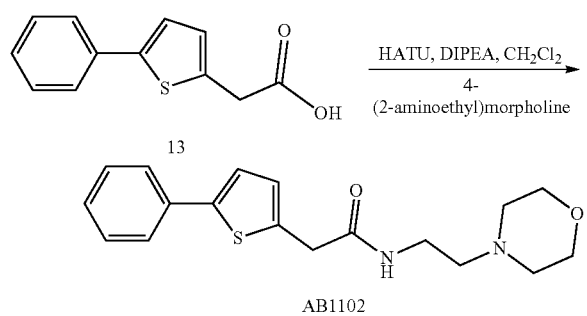

AB1102

N-(2-morpholinoethyl)-2-(5-phenylthiophen-2-yl)acetamide(AB1102): Compound AB1102 (102 mg, 34%) was synthesized from compound 13 by following general procedure C. $^1$H NMR (CDCl$_3$, 500 MHz): δ 7.56; (d, J=4.87 Hz, 2H), 7.37; (t, J=5.36 Hz, 2H), 7.30; (t, 1H), 7.20; (d, 1H), 6.41; (s, 1H), 3.78; (s, 2H), 3.55; (t, J=4.87 Hz, 4H), 3.34; (q, J=5.8, 2H), 2.45; (t, J=6.34 Hz, 2H), 2.38; (t, J=4.39 Hz, 4H). MS: 331 (M+H)$^+$.

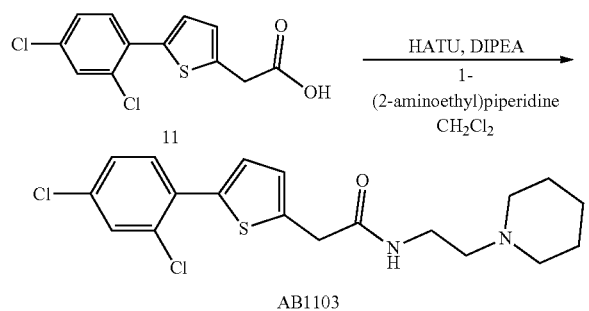

AB1103

2-(5-(2,4-dichlorophenyl)thiophen-2-yl)-N-(2-(piperidin-1-yl)ethyl)acetamide (AB1103): Compound AB110 (35 mg, 13%) was synthesized from compound 11 by following general procedure C. $^1$H NMR (DMSO-d$_6$, 500 MHz): δ 8.19; (s, 1H), 7.73; (d, J=2.1 Hz, 1H), 7.62; (d, J=8.3 Hz, 1H), 7.48; (dd, J=8.6 Hz, 2.4 Hz, 1H), 7.30; (d, J=3.4 Hz, 1H), 6.97; (d, J=4.2 Hz, 1H), 3.70; (s, 2H), 3.27; (s, 2H), 2.53; (s, 2H), 1.55; (s, 4H), 1.40; (s, 2H), 1.25-1.22; (m, 4H). MS: 397 (M+H)$^+$.

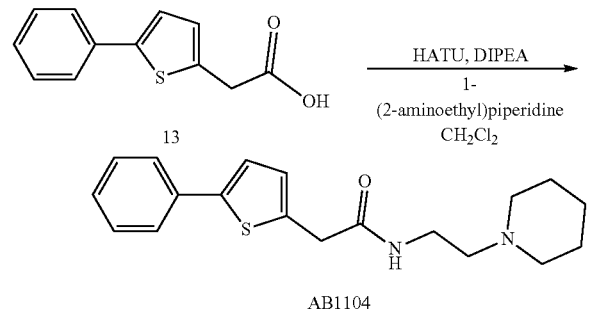

AB1104

2-(5-phenylthiophen-2-yl)-N-(2-(piperidin-1-yl)ethyl)acetamide (AB1104): Compound AB1104 (165 mg, 55%) was synthesized from compound 13 by following general procedure C. $^1$H NMR (DMSO-d$_6$, 500 MHz): δ 8.41; (s, 1H), 7.59; (d, J 7.6 Hz, 2H), 7.40; (t, J=7.9 Hz, 2H), 7.34; (d, J=3.4 Hz, 1H), 7.29; (t, J=7.2 Hz, 1H), 6.93; (d, J=4.1 Hz, 1H), 3.70; (s, 2H), 3.43; (s, 2H), 3.05; (s, 2H), 2.87; (s, 2H), 1.69; (s, 4H), 1.27-1.22; (m, 2H). MS: 329 (M+H)$^+$.

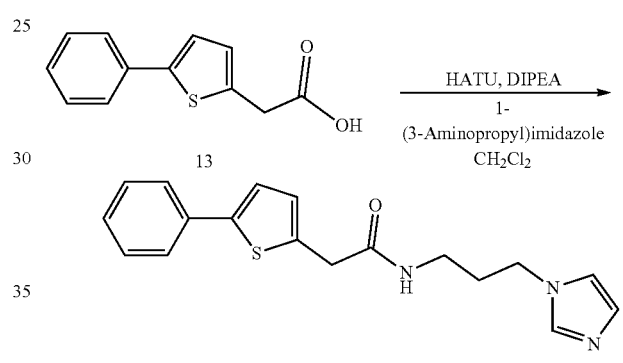

AB1105

N-(3-(1H-imidazol-1-yl)propyl)-2-(5-phenylthiophen-2-yl)acetamide (AB1105): Compound AB1105 (22 mg, 11%) was synthesized from compound 13 by following general procedure C. $^1$H NMR (CDCl$_3$, 500 MHz): δ 7.57-7.55; (m, 2H), 7.53; (s, 1H), 7.39-7.36; (m, 2H), 7.30-7.27; (m, 1H), 7.19; (d, J=3.6 Hz, 1H), 7.04; (s, 1H), 6.90; (dd, J=2.4 Hz, 0.9 Hz, 2H), 5.97; (s, 1H), 3.96; (t, 6.9 Hz, 2H), 3.77; (s, 2H), 3.26; (q, J=6.5 Hz, 2H), 2.00-1.96; (m, 2H). MS: 326 (M+H)$^+$.

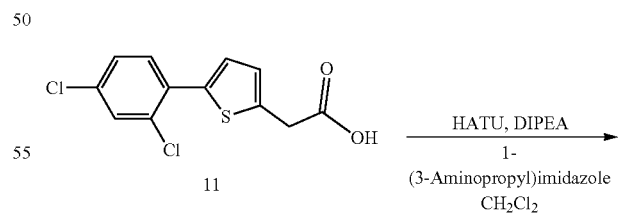

AB1106

N-(3-(1H-imidazol-1-yl)propyl)-2-(5-(2,4-dichlorophenyl)thiophen-2-yl)acetamide (AB1106): Compound AB1106 (105 mg, 38%) was synthesized from compound 11 by following general procedure C. $^1$H NMR (DMSO-d$_6$, 500 MHz): δ 1.84; (t, J=5.5 Hz, 1H), 7.73; (d, J=2.1 Hz, 1H), 7.66; (s, 1H), 7.62; (d, J=8.3 Hz, 1H), 7.48; (dd, J=8.3 Hz, 2.1 Hz, 1H), 7.31; (d, J=3.4 Hz, 1H), 7.18; (s, 1H), 6.97; (d, J=3.4 Hz, 1H), 6.92; (s, 1H), 3.97; (t, J=6.9 Hz, 2H), 3.70; (s, 2H), 3.04; (q, J=6.2 Hz, 2H), 1.88-1.82; (m, 2H). MS: 394 (M+H)$^+$.

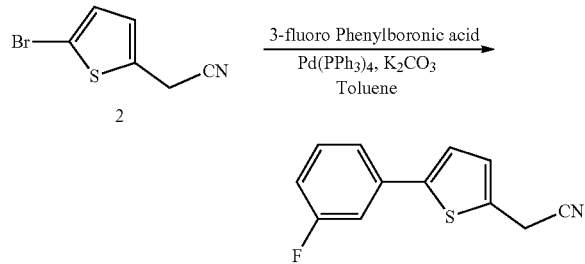

2-(5-(3-fluorophenyl)thiophen-2-yl)acetonitrile (14): compound 12 (3.1 gm) synthesized from compound 2 by following general procedure A. $^1$H NMR (DMSO-d$_6$, 500 MHz): δ 7.52-7.50; (m, 2H), 7.48-7.43; (m, 2H), 7.17-7.12; (m, 1H), 7.10; (d, J=3.4 Hz, 1H), 4.34; (s, 2H).

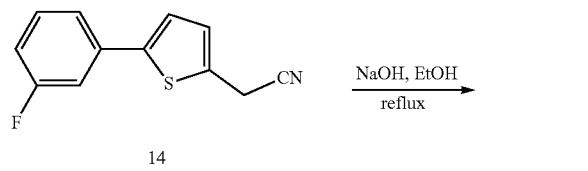

2-(5-(3-fluorophenyl)thiophen-2-yl)acetic acid (15): Compound 15 (1.7 g) Synthesized from compound 13 by following General procedure B. $^1$H NMR (DMSO-d$_6$, 500 MHz): δ 12.64; (bs, 1H), 7.48-7.42; (m, 4H), 7.13-7.10; (m, 1H), 6.97; (d, J=3.4 Hz, 1H), 3.85; (s, 2H).

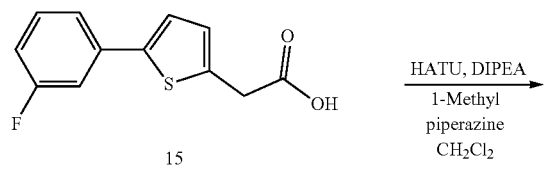

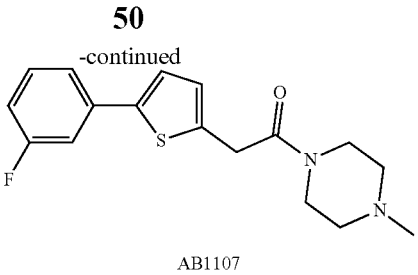

2-(5-(3-fluorophenyl)thiophen-2-yl)-1-(4-methylpiperazin-1-yl)ethan-1-one(AB1107): Compound AB1107 (115 mg, 71%) was synthesized from compound 15 by following general procedure C. $^1$H NMR (CDCl$_3$, 500 MHz): δ 7.34-7.31; (m, 2H), 7.24 (t, J=2.0 Hz, 1H), 7.16 (d, J=3.8 Hz, 1H), 6.95; (m, 1H), 6.97-6.94; (m, 1H), 6.87; (dt, J=3.6 Hz, 0.9 Hz, 1H), 3.90; (d, J=0.9 Hz, 2H), 3.69; (t, J=5.0 Hz, 2H), 3.56; (t, J=5.1 Hz, 2H), 2.38; (dt, J=20.3 Hz, 5.1 Hz, 4H), 2.29; (s, 3H). MS: 319 (M+H)$^+$.

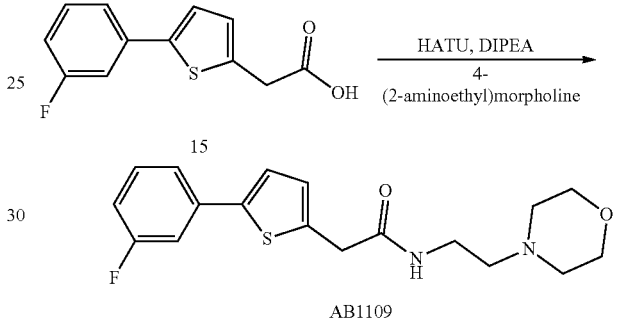

2-(5-(3-fluorophenyl)thiophen-2-yl)-N-(2-morpholinoethyl)acetamide(AB1108): Compound AB1108 (102 mg, 58%) was synthesized from compound 15 by following general procedure C. $^1$H NMR (CDCl$_3$, 500 MHz): δ 7.34-7.32; (m, 2H), 7.24; (m, 1H), 7.21; (d, J=3.6 Hz, 1H), 6.99-6.96; (m, 1H), 6.93; (d, J=3.6 Hz, 1H), 6.35; (s, 1H), 3.78; (s, 2H), 3.55; (t, J=4.5 Hz, 4H), 3.33; (q, J=5.7 Hz, 2H), 2.44; (t, J=6.0 Hz, 2H), 2.37; (t, J=4.4 Hz, 4H). MS: 349 (M+H)$^+$.

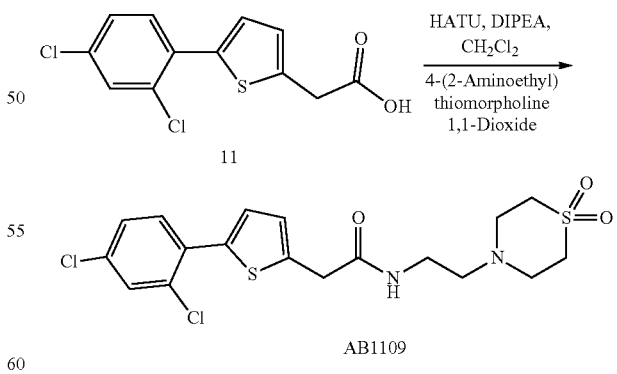

2-(5-(2,4-dichlorophenyl)thiophen-2-yl)-N-(2-(1,1-dioxidothiomorpholino)ethyl)acetamide (AB1109): Compound AB1109 (531 mg, 57%) was synthesized from compound 11 by following general procedure C. $^1$H NMR (DMSO-d$_6$, 500 MHz): δ 8.08; (t, J=5.5 Hz, 1H), 7.73; (d, J=2.1 Hz, 1H), 7.62; (d, J=8.3 Hz, 1H), 7.48; (dd, J=8.3 Hz, 2.1 Hz, 1H), 7.30; (d, J=4.1 Hz, 1H), 6.96; (d, 3.4 Hz, 1H), 3.69; (s, 2H), 3.19; (q, J=6.2 Hz, 2H), 3.04; (d, J=10.3 Hz, 4H), 2.91; (d, J=4.8 Hz, 4H), 2.55; (t, J=6.5 Hz, 2H). MS: 447 (M+H)⁺. HPLC: 98%

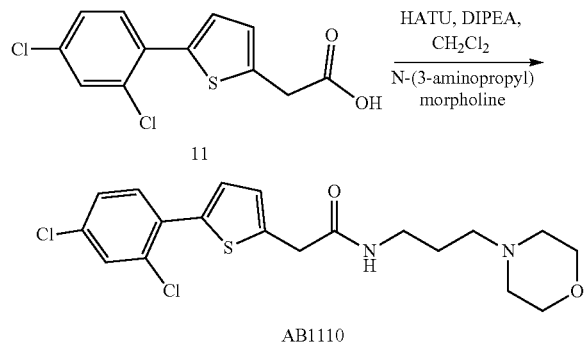

2-(5-(2,4-dichlorophenyl)thiophen-2-yl)-N-(3-morpholinopropyl)acetamide (AB1110): Compound AB1110 (470 mg, 33%) was synthesized from compound 11 by following general procedure C. $^1$H NMR (DMSO-d$_6$, 500 MHz): δ 8.15; (t, J=5.5 Hz, 1H), 7.73; (d, J=2.1 Hz, 1H), 7.62; (d, J=8.3 Hz, 1H), 7.48; (dd, J=8.3 Hz, 2.1 Hz, 1H), 7.30; (d, J=4.1 Hz, 1H), 6.95; (d, J=4.1 Hz, 1H), 3.67; (s, 2H), 3.10; (q, J=6.4 Hz, 2H), 2.31-2.25; (m, 6H), 1.59-153; (m, 2H). MS: 413 (M+H)⁺. HPLC: 99.5%

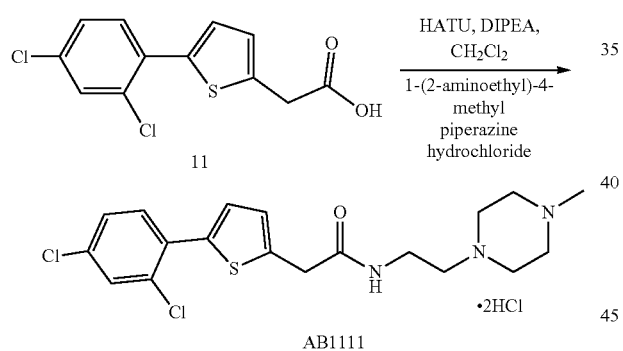

2-(5-(2,4-dichlorophenyl)thiophen-2-yl)-N-(2-(4-methylpiperazin-1-yl)ethyl)acetamide hydrochloride (AB1111): Compound AB1111 (37 mg) was synthesized from compound 11 by following general used for the synthesis of AB1062. $^1$H NMR(dmso-d$_6$, 500 MHz): δ 8.43; (s, 1H), 7.74; (d, J=2.21 Hz, 1H), 7.63; (d, J=8.3 Hz, 1H), 7.49; (dd, J=8.3 Hz, 2.1 Hz, 1H), 7.31; (d, J=4.1 Hz, 1H), 6.98; (d, J=3.4 Hz, 1H), 3.75; (s, 2H), 3.60-3.20; (m, 8H), 2.5; (s, 3H).

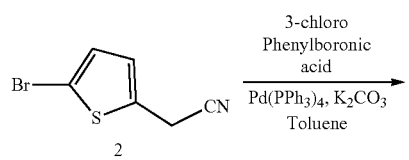

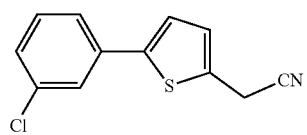

2-(5-(3-chlorophenyl)thiophen-2-yl)acetonitrile (16): compound 16 (5.6 gm) synthesized from compound 2 by following general procedure A. $^1$H NMR (DMSO-d$_6$, 500 MHz): δ 7.72; (t, J=2.1 Hz, 1H), 7.59-7.57; (m, 1H), 7.52; (d, J=4.1 Hz, 1H), δ 7.45; (t, J=7.9 Hz, 1H), 7.38; (dd, J=9.0 Hz, 2.1 Hz, 1H), 7.10; (d, J=3.4 Hz, 1H), 4.34; (s, 2H).

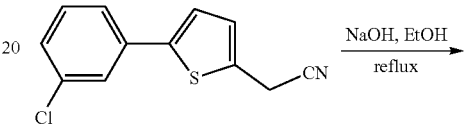

2-(5-(3-chlorophenyl)thiophen-2-yl)acetic acid (17): Compound 17 (1.7 g) Synthesized from compound 16 by following General procedure B. $^1$H NMR (DMSO-d$_6$, 500 MHz): δ 12.64; (bs, 1H), 7.68; (t, J=2.1 Hz, 1H), 7.57-7.55; (m, 1H), 7.46-7.40; (m, 2H), 7.34; (dd, J=9.0 Hz, 2.1 Hz, 1H), 6.97; (d, J=3.4 Hz, 1H), 3.86; (s, 2H).

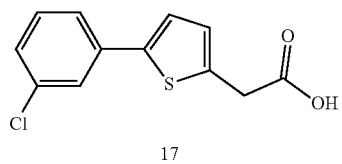

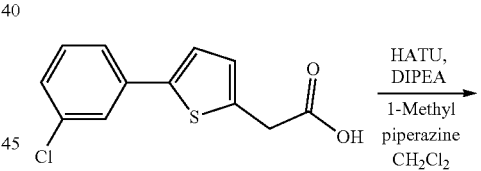

2-(5-(3-chlorophenyl)thiophen-2-yl)-1-(4-methylpiperazin-1-yl)ethan-1-one (AB1112): Compound AB1112 (155 mg, 78%) was synthesized from compound 17 by following general procedure C. $^1$H NMR (CDCl$_3$, 500 MHz): δ 7.55; (t, J=1.9 Hz, 1H), 7.43-7.42; (m, 1H), 7.28; (t, J=7.9 Hz, 1H), 7.22; (dq, J=8.0 Hz, 1.0 Hz, 1H), 7.16; (d, J=3.6 Hz, 1H), 6.87; (dt, J=3.6 Hz, 0.9 Hz, 1H), 3.90; (d, J=0.7 Hz, 2H), 3.68; (t, J=4.9 Hz, 2H), 3.55; (t, J=5.1 Hz, 2H), 2.38; (dt, J=20.4 Hz, 5.1 Hz, 4H), 2.29; (s, 3H). MS: 335 (M+H)⁺.

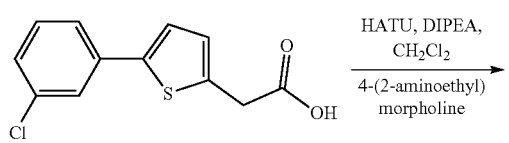

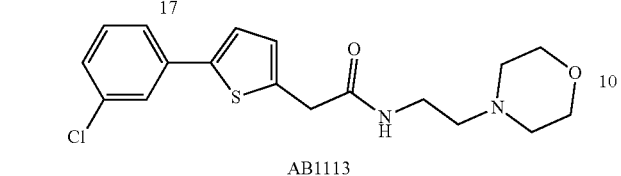

2-(5-(3-chlorophenyl)thiophen-2-yl)-N-(2-morpholinoethyl)acetamide (AB1113): Compound AB1113 (65 mg, 30%) was synthesized from compound 17 by following general procedure C. $^1$H NMR (CDCl$_3$, 500 MHz): δ 7.54; (t, J=1.8 Hz, 1H), 7.43; (dt, J=7.7 Hz, 1.4 Hz, 1H), 7.30 (t, J=7.8 Hz, 1H), 7.30-7.25; (m, 1H), 7.21, J=3.6 Hz, 1H), 6.92; (d, J=3.6 Hz, 1H), 6.35; (s, 1H), 3.77; (s, 2H), 3.56; (t, J=4.6 Hz, 4H), 3.34; (q, J=5.6 Hz, 2H), 2.45; (t, J=6.0 Hz, 2H), 2.38; (t, J=4.5 Hz, 4H). MS: 365 (M+H)$^+$.

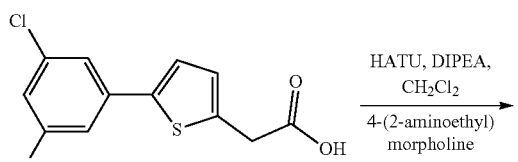

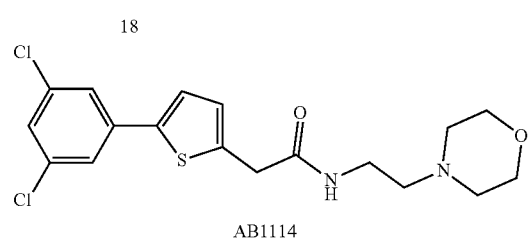

2-(5-(3,5-dichlorophenyl)thiophen-2-yl)-N-(2-morpholinoethyl)acetamide (AB1114): Compound AB1114 (42 mg, 30%) was synthesized from compound 18 by following general procedure C. $^1$H NMR (CDCl$_3$, 500 MHz): δ 7.42; (d, J=1.7 Hz, 2H), 7.26-7.25; (m, 1H), 7.22; (d, J=3.6 Hz, 1H), 6.93; (d, J=3.6 Hz, 1H), 6.30; (s, 1H), 3.78; (s, 2H), 3.58; (t, J=4.4 Hz, 4H), 3.35; (q, J=5.6 Hz, 2H), 2.46; (t, J=6.0 Hz, 2H), 2.39; (t, J=4.4 Hz, 4H). MS: 399 (M+H)$^+$.

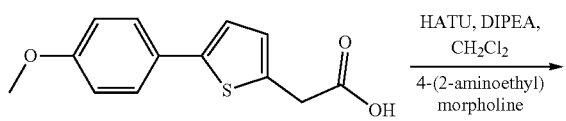

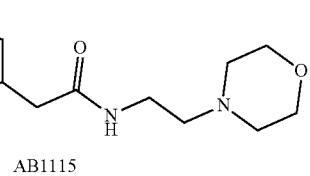

2-(5-(4-methoxyphenyl)thiophen-2-yl)-N-(2-morpholinoethyl)acetamide (AB1115): Compound AB1115 (35 mg, 75%) was synthesized from compound 19 by following general procedure C. $^1$H NMR (CDCl$_3$, 400 MHz): δ 7.48; (d, 2H), 7.07; (d, 1H), 6.91-6.88; (m, 3H), 3.38; (s, 3H), 3.76; (s, 2H), 3.57; (s, 3H), 3.34; (bd, 2H), 2.45; (bd, 6H). MS: 361 (M+H)$^+$.

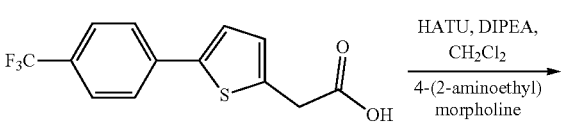

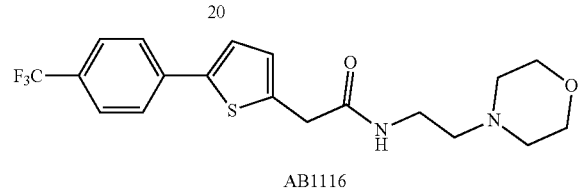

N-(2-morpholinoethyl)-2-(5-(4-(trifluoromethyl)phenyl)thiophen-2-yl)acetamide (AB1116): Compound AB1116 (33 mg, 69%) was synthesized from compound 20 by following general procedure C. $^1$H NMR (CDCl$_3$, 400 MHz): δ 7.63; (q, 4H), 7.27; (t, 1H), 6.95; (d, 1H), 6.45; (bs, 1H), 3.79; (s, 2H), 3.59; (s, 4H), 3.36; (q, 2H), 2.49; (t, 2H), 2.42; (bs, 4H). MS: 399 (M+H)$^+$.

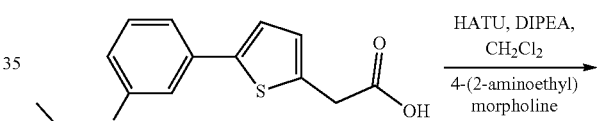

2-(5-(3-(3,5-dimethyl-1H-pyrazol-1-yl)phenyl)thiophen-2-yl)-N-(2-morpholinoethyl) acetamide (AB 1117): Compound AB1117 (28 mg, 45%) was synthesized from compound 21 by following general procedure C. $^1$H NMR (CDCl$_3$, 400 MHz): δ 7.63; (s, 1H), 7.52; (d, 1H), 7.44; (t, 1H), 7.32; (d, 1H), 7.26-7.24; (m, 1H), 6.92; (s, 1H), 6.45; (bs, 1H), 6.01; (s, 1H), 3.77; (s, 2H), 3.58; (bs, 4H), 3.35; (q, 2H), 2.48; (t, 2H), 2.41; (bs, 4H), 2.33; (s, 3H), 2.30; (s, 3H). MS: 425 (M+H)$^+$.

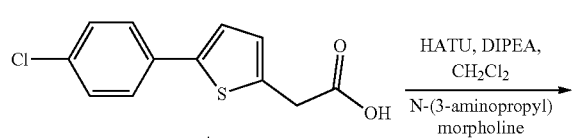

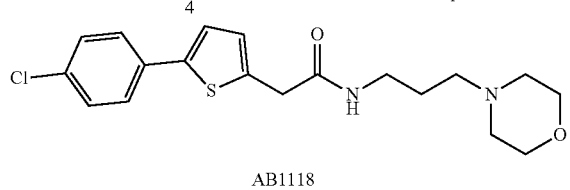

2-(5-(4-chlorophenyl)thiophen-2-yl)-N-(3-morpholinopropyl)acetamide (AB1118): Compound AB1118 (65 mg) was synthesized from compound 4 by following general procedure C. $^1$H NMR (CDCl$_3$, 500 MHz): δ 7.48; (dt, J=9.0 Hz, 2.3 Hz, 2H), 7.35-7.23; (m, 2H), 7.15; (d, J=3.6 Hz, 1H), 6.90; (d, J=3.4 Hz, 1H), 6.75; (s, 1H), 3.74 (s, 2H), 3.61; (t, J=4.6 Hz, 4H), 3.37; (q, J=6.0 Hz, 2H), 2.39; (t, J=6.4 Hz, 6H), 1.69-1.64; (m, 2H). MS: 379 (M+H)$^+$.

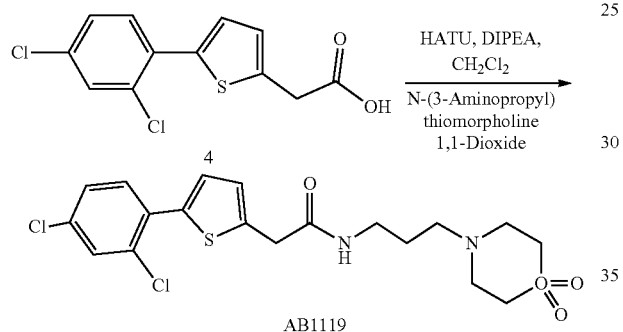

2-(5-(2,4-dichlorophenyl)thiophen-2-yl)-N-(3-(1,1-dioxidothiomorpholino)propyl)acetamide (AB1119): Compound AB1119 (1.86 g, 50%) was synthesized from compound 11 by following general procedure C. $^1$H NMR (DMSO-d$_6$, 500 MHz): δ 8.12; (t, J=5.5 Hz, 1H), 7.73; (d, J=2.1 Hz, 1H), 7.62; (d, J=8.3 Hz, 1H), 7.48; (dd, J=8.3 Hz, 2.1 Hz, 1H), 7.30; (d, J=3.4 Hz, 1H), 6.95; (d, J=3.4 Hz, 1H), 3.67; (s, 2H), 3.10; (q, J=6.4 Hz, 2H), 3.06; (t, J=6.4 Hz, 2H), 2.84; (dd, J=6.2 Hz, 4.1 Hz, 4H), 2.45; (t, J=6.9 Hz, 2H), 1.75; (q, J=6.9 Hz, 2H). MS: 461 (M+H)$^+$. HPLC: 99.45%.

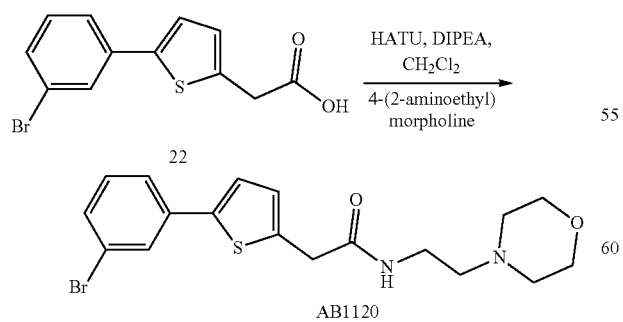

2-(5-(3-bromophenyl)thiophen-2-yl)-N-(2-morpholinoethyl)acetamide (AB1120): Compound AB1120 (1.2 g, 78%) was synthesized from compound 22 by following general procedure C. $^1$H NMR (CDCl$_3$, 400 MHz): δ 7.70; (s, 1H), 7.47; (d, 2H), 7.40; (d, 1H), 7.26-7.19; (m, 2H), 6.91; (d, 1H), 6.34; (s, 1H), 3.78; (s, 2H), 3.56; (t, 4H), 3.33; (q, 2H), 2.46-2.37; (m, 6H), 1.69; (s, 2H). MS: 409 (M+H)$^+$.

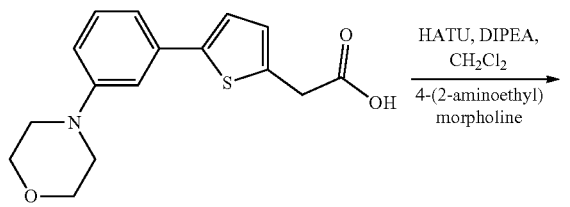

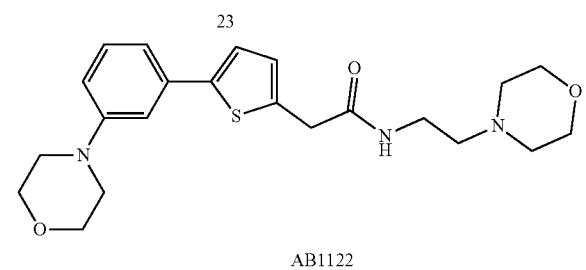

N-(2-morpholinoethyl)-2-(5-(3-morpholinophenyl)thiophen-2-yl)acetamide (AB1122): Compound AB1122 (46 mg, 70%) was synthesized from compound 23 by following general procedure C. $^1$H NMR (CDCl$_3$, 400 MHz): δ 7.29-7.26; (m, 1H), 7.18; (d, 1H), 7.09-7.07; (m, 2H), 6.90; (d, 1H), 6.86-6.84; (m, 1H), 6.37; (bs, 1H), 3.87; (t, 4H), 3.77; (s, 2H), 3.55; (t, 4H), 3.31; (q, 2H), 3.19; (t, 4H), 2.43; (t, 2H), 2.36; (t, 4H). MS: 416 (M+H)$^+$.

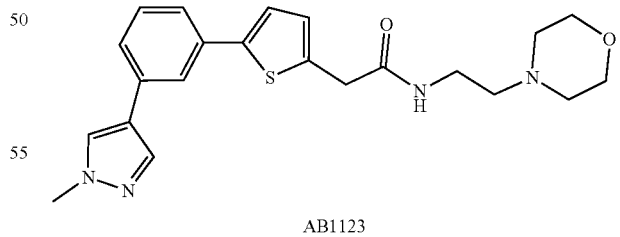

2-(5-(3-(1-methyl-1H-pyrazol-4-yl)phenyl)thiophen-2-yl)-N-(2-morpholinoethyl)acetamide (AB1123): Compound AB1123 (25 mg, 66%) was synthesized from compound 24 by following general procedure C. $^1$H NMR (CDCl$_3$, 400 MHz): δ 7.81-7.25; (m, 7H), 6.96; (s, 1H), 6.45; (s, 1H), 3.98; (bs, 2H), 3.81; (s, 2H), 3.60; (s, 3H), 3.37; (bs, 2H), 2.49-241; (m, 5H), 1.75-1.74; (m, 2H). MS: 411 (M+H)$^+$.

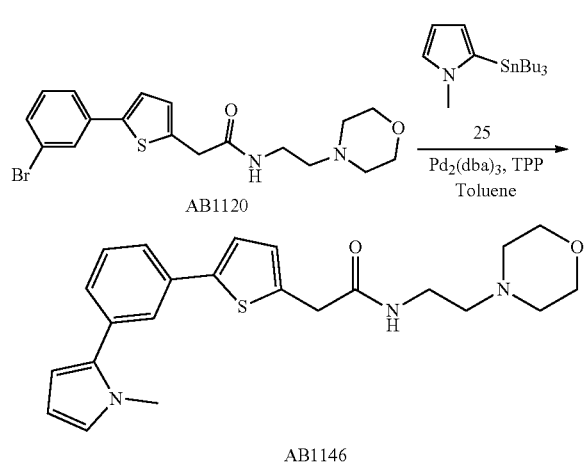

2-(5-(3-(1-methyl-1H-pyrrol-2-yl)phenyl)thiophen-2-yl)-N-(2-morpholinoethyl)acetamide (AB1146): To a stirred solution of Compound AB1120 (100 mg, 0.24 mmol) in 10 mL toluene. TPP (32 mg, 0.12) followed by 1-Methyl-2-(tributylstannyl)pyrrole (25) (99 mg, 0.26 mmol) and Pd$_2$(dba)$_3$ (11 mg, 0.012 mmol) were added and stirred at 80° C. for 8 hr. concentrated the reaction mixture purified by column chromatography to afford compound AB1146 (65 mg, 65%) as off white solid. $^1$H NMR (DMSO-d$_6$, 500 MHz): δ 8.05; (d, 5.5 Hz, 1H), 7.60 (s, 1H), 7.50; (d, J=7.6 Hz, 1H), 7.44-7.39; (m, 2H), 7.35; (d, J=7.6 Hz, 1H), 6.92; (d, J=3.4 Hz, 1H), 6.87; (t, J=2.4 Hz, 1H), 6.23; (q, J=1.8 Hz, 1H), 6.08; (t, J=3.1 Hz, 1H), 3.68; (t, J=14.1 Hz, 6H), 3.54; (q, J=4.8 Hz, 5H), 3.19; (q, J=6.2 Hz, 2H), 2.35; (t, J=6.5 Hz, 7H). MS: 410 (M+H)$^+$.

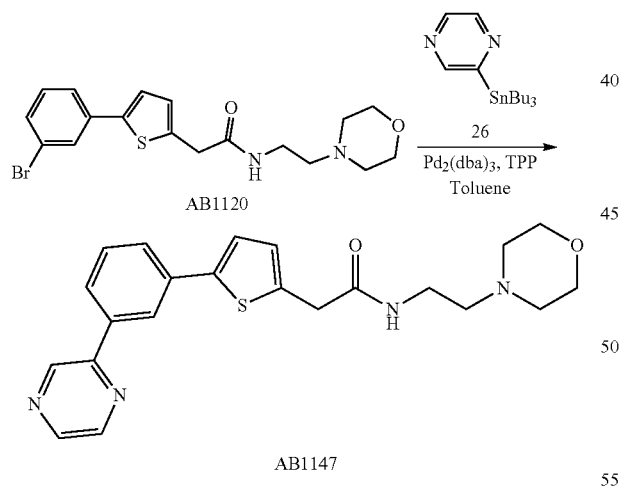

N-(2-morpholinoethyl)-2-(5-(3-(pyrazin-2-yl)phenyl)thiophen-2-yl)acetamide (AB1147): To a stirred solution of Compound AB1120 (100 mg, 0.24 mmol) in 10 mL toluene. TPP (32 mg, 0.12) followed by 2-(tributylstannyl)pyrazine 26 (84 μL, 0.26 mmol) and Pd$_2$(dba)$_3$ (11 mg, 0.012 mmol) were added and stirred at 80° C. for 8 hr. concentrated the reaction mixture purified by column chromatography to afford compound AB1147 (46 mg, 46%) as off white solid. $^1$H NMR (DMSO-d$_6$, 500 MHz): δ 9.35; (d, J=1.4 Hz, 1H), 8.76; (t, J=2.1 Hz, 1H), 8.66; (d, J=2.1 Hz, 1H), 8.35; (s, 1H), 8.05; (d, J=7.6 Hz, 2H), 7.73; (d, J=8.3 Hz, 1H), 7.57; (t, J=7.9 Hz, 1H), 7.49; (d, J=3.4 Hz, 1H), 6.96; (d, J=3.4 Hz, 1H), 3.68; (s, 2H), 3.55; (t, J=4.5 Hz, 4H), 3.20; (q, J=6.4 Hz, 2H), 2.36; (t, J=6.5 Hz, 6H). MS: 409 (M+H)$^+$.

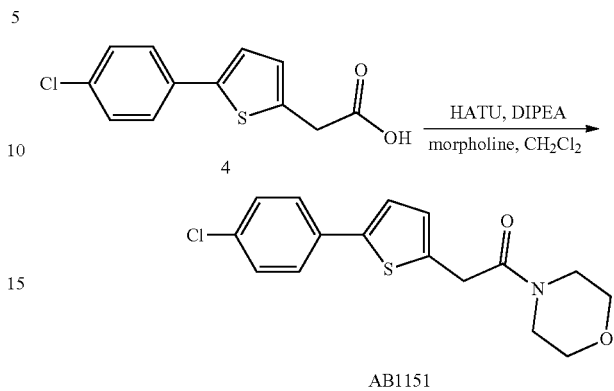

2-(5-(4-chlorophenyl)thiophen-2-yl)-1-morpholinoethan-1-one (AB1151): Compound AB1151 (128 mg, 50%) was synthesized from compound 4 by following general procedure C. $^1$H NMR (DMSO-d$_6$, 500 MHz): δ 7.63-7.61; (m, 2H), 7.45-7.44 (m, 2H), 7.37; (d, J=3.4 Hz, 1H), 6.93; (d, J=3.4 Hz, 1H), 3.98; (s, 2H), 3.56-3.54; (m, 6H), 3.47; (t, J=3.4 Hz, 1H). MS: 322 (M+H)$^+$.

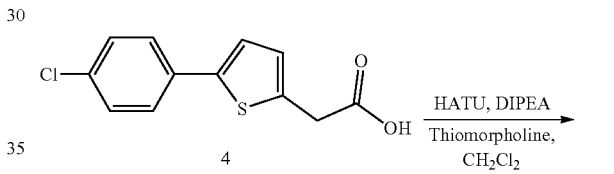

2-(5-(4-chlorophenyl)thiophen-2-yl)-1-thiomorpholino-ethan-1-one (AB1152): Compound AB1152 (140 mg, 58%) was synthesized from compound 4 by following general procedure C. $^1$H NMR (DMSO-d$_6$, 500 MHz): δ 7.63-7.61; (m, 2H), 7.45; (dd, J=8.6 Hz, 2.4 Hz), 7.38; (d, J=3.4 Hz, 1H), 6.94; (d, J=3.4 Hz, 1H), 3.99; (s, 2H), 3.76; (dt, J=23.9 Hz, 5.0 Hz, 4H), 2.55-2.54; (m, 4H). MS: 338 (M+H)$^+$.

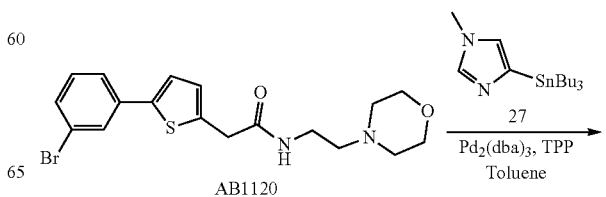

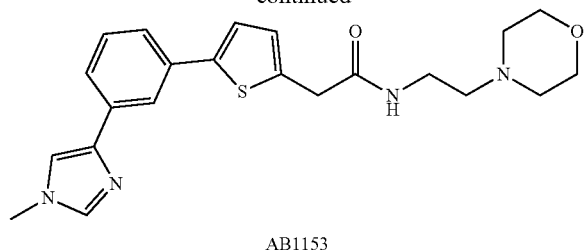

AB1153

2-(5-(3-(1-methyl-1H-imidazol-4-yl)phenyl)thiophen-2-yl)-N-(2-morpholinoethyl)acetamide (AB 1153): Compound AB1153 (10 mg, 6%) was synthesized from compound AB1120 by following general procedure for the synthesis of AB1146. $^1$H NMR (DMSO-$d_6$, 500 MHz): δ 8.04; (t, J=5.5 Hz, 1H), 7.96 (s, 1H), 7.67; (d, J=20.0 Hz, 2H), 7.63; (d, J=7.6 Hz, 1H), 7.42; (d, J=7.6 Hz, 1H), 7.37-7.34; (m, 2H), 6.93; (d, J=3.4 Hz, 1H), 3.66; (s, 2H), 3.55; (t, J=4.5 Hz, 4H), 3.20; (q, 6.2 Hz, 2H), 2.36; (t, J=4.1 Hz, 6H). MS: 411 (M+H)$^+$.

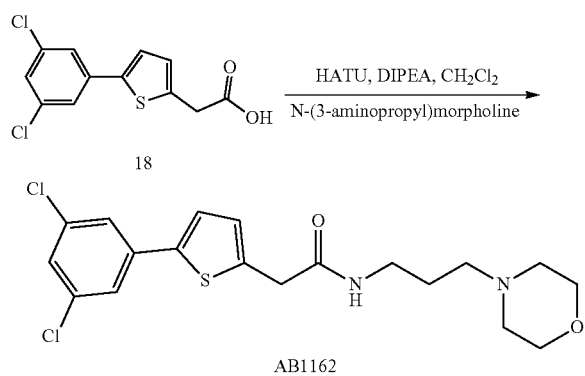

AB1162

2-(5-(3,5-dichlorophenyl)thiophen-2-yl)-N-(3-morpholinopropyl)acetamide (AB1162): Compound AB1162 (82 mg, 39%) was synthesized from compound 18 by following general procedure C. $^1$H NMR (DMSO-$d_6$, 500 MHz): δ 8.13; (t, J=5.2 Hz, 1H), 7.63; (d, J=1.4 Hz, 2H), 7.54; (d, J=3.4 Hz, 1H), 7.50; (t, J=1.7 Hz, 1H), 6.93; (d, J=3.4 Hz, 1H), 3.66; (s, 2H), 3.54; (t, J=4.8 Hz, 4H), 3.09; (q, J=6.7 Hz, 2H), 2.30; (s, 4H), 2.26; (t, J=7.2 Hz, 2H), 1.58-1.53; (m, 2H). MS: 413 (M+H)$^+$.

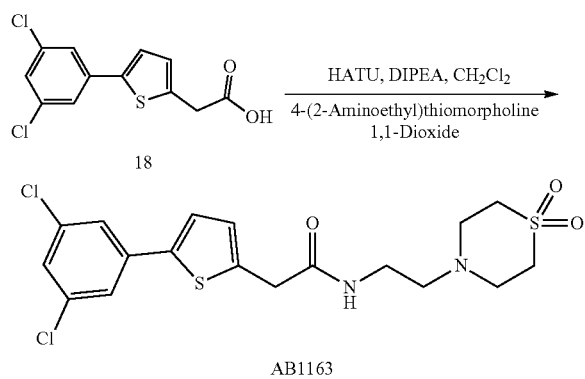

AB1163

2-(5-(3,5-dichlorophenyl)thiophen-2-yl)-N-(3-(1,1-dioxidothiomorpholino)propyl)acetamide (AB1163): Compound AB1163 (142 mg, 65%) was synthesized from compound 18 by following general procedure C. $^1$H NMR (DMSO-$d_6$, 500 MHz): δ 8.06; (t, J=5.5 Hz, 1H), 7.63; (d, J=2.1 Hz, 2H), 7.54; (d, J=4.1 Hz, 1H), 7.49; (t, J=1.7 Hz, 1H), 6.95; (1H, d), 3.58; (s, 2H), 3.20-3.16; (m, 2H), 3.04; (t, J=4.8 Hz, 4H), 2.90; (t, J=5.2 Hz, 4H), 2.54; (t, J=6.5 Hz, 2H). MS: 447 (M+H)$^+$.

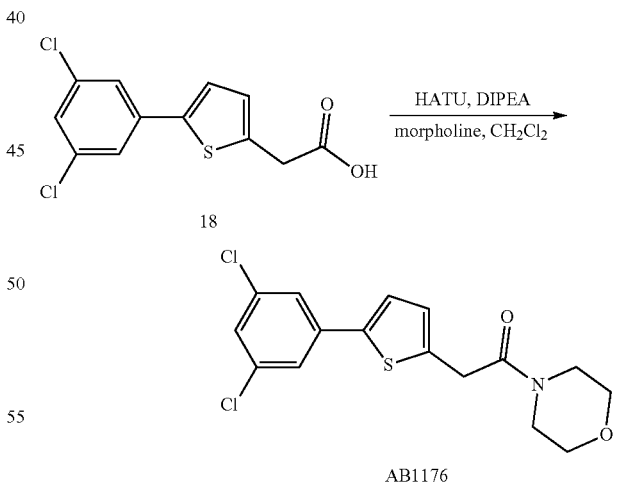

2-(5-(3,5-dichlorophenyl)thiophen-2-yl)-N-(3-(1,1-dioxidothiomorpholino)propyl)acetamide (AB1164): Compound AB1164 (149 g, 61%) was synthesized from compound 18 by following general procedure C. $^1$H NMR (DMSO-$d_6$, 500 MHz): δ 8.11; (t, J=5.5 Hz, 1H), 7.63; (d, J=2.1 Hz, 2H), 7.54; (d, J=3.4 Hz, 1H), 7.50; (t, J=1.7 Hz, 1H), 6.94; (d, J=3.4 Hz, 1H), 3.66; (s, 2H), 3.09; (q, J=6.4 Hz, 2H), 3.05; (t, J=4.8 Hz, 4H), 2.84; (t, J=4.8 Hz, 4H), 2.45; (t, J=7.2 Hz, 2H), 1.58-1.33; (m, 2H). MS: 461 (M+H)$^+$. HPLC: 99.2%.

2-(5-(3,5-dichlorophenyl)thiophen-2-yl)-1-morpholinoethanone (AB1176): Compound AB1176 (56 mg, 38%) was synthesized from compound 18 by following general procedure C. $^1$H NMR (400 MHz, DMSO-$d_6$): δ 7.65; (d, J=2.1 Hz, 2H), 7.55; (d, J=3.4 Hz, 1H), 7.50; (t, J=2.1 Hz, 1H), 6.96; (d, J=3.4 Hz, 1H), 4.01; (s, 2H), 3.55; (d, J=4.1 Hz, 6H), 3.47; (t, J=4.8 Hz, 2H). MS: 356 (M+H)$^+$.

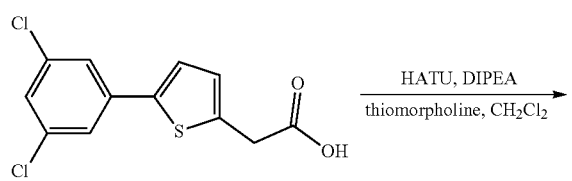

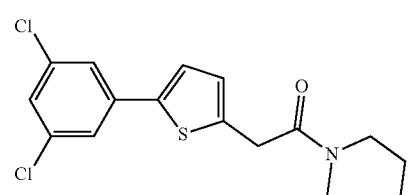

2-(5-(3,5-dichlorophenyl)thiophen-2-yl)-1-thiomorpholinoethanone (AB1177): Compound AB1177 (85 mg, 54%) was synthesized from compound 18 by following general procedure C. $^1$H NMR (400 MHz, DMSO-$d_6$): δ 7.65; (d, J=1.4 Hz, 2H), 7.56; (d, J=3.4 Hz, 1H), 7.50; (t, J=1.7 Hz, 1H), 6.98; (d, J=4.1 Hz, 1H), 4.01; (s, 4H), 3.77; (dt, J=23.6; Hz, 5.2 Hz, 4H), 2.56; (q, 4H). MS: 371; (M+H)$^+$.

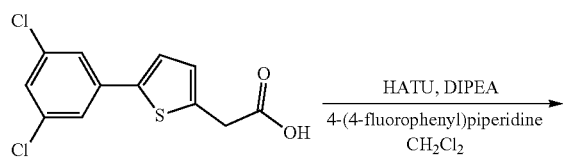

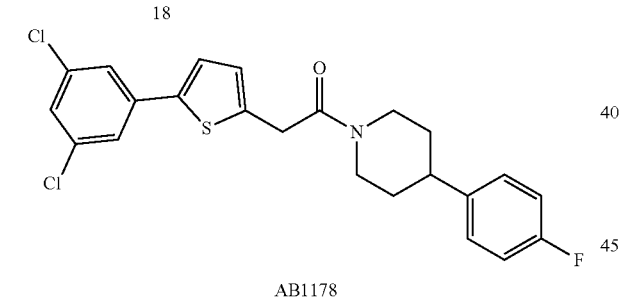

2-(5-(3,5-dichlorophenyl)thiophen-2-yl)-1-(4-(4-fluorophenyl)piperidin-1-yl)ethan-1-one (AB1178): Compound AB1178 (78 mg, 50%) was synthesized from compound 18 by following general procedure C. $^1$H NMR (DMSO-$d_6$, 500 MHz): δ 7.66; (d, J=2.1 Hz, 2H), 7.56; (d, J=4.1 Hz, 1H), 7.51; (t, J=1.7 Hz, 1H), 7.27-7.24; m, 2H), 7.09; (t, J=9.0 Hz, 2H), 6.99; (d, J=3.4 Hz, 1H), 4.55; (d, J=13.1 Hz, 1H), 4.12; (d, J=13.1 Hz, 1H), 4.04; (s, 2H), 3.15; (t, J=12.1 Hz, 1H), 2.81-2.77; (m, 1H), 2.65; (t, J=11.7 Hz, 1H), 1.77; (d, J=12.4 Hz, 2H). MS: 448 (M+H)$^+$.

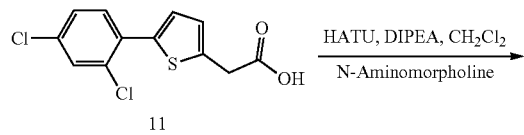

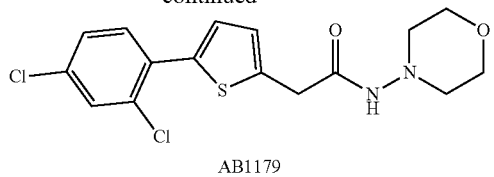

2-(5-(2,4-dichlorophenyl)thiophen-2-yl)-N-morpholinoacetamide (AB1179): Compound AB1179 (100 mg, 52%) was synthesized from compound 11 by following general procedure C. $^1$H NMR(CDCl$_3$, 500 MHz): δ 7.44-7.41; (m, 2H), 7.19; (d, J=3.4 Hz, 1H), 6.96-6.94; (m, 2H), 6.20; (s, 1H), 4.02; (s, 2H), 3.81-3.79; (m, 4H), 2.83; (t, J=4.8 Hz, 4H). MS: 371 (M+H)$^+$.

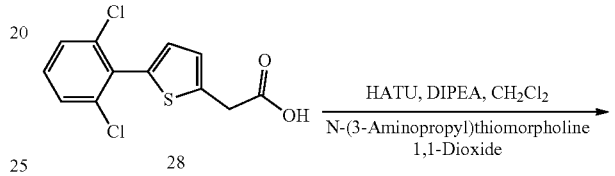

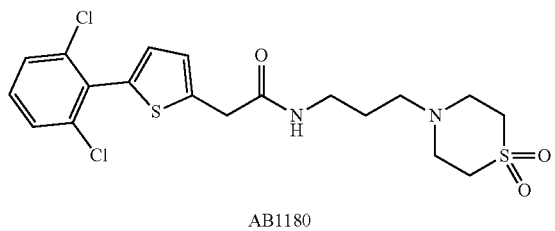

2-(5-(2,6-dichlorophenyl)thiophen-2-yl)-N-(3-(1,1-dioxidothiomorpholino)propyl)acetamide (AB1180): Compound AB1180 (177 mg) was synthesized from compound 28 by following general procedure C. $^1$H NMR(CDCl$_3$, 500 MHz): δ 7.41; (d, J=8.3 Hz, 2H), 7.29; (d, J=2.1, 1H), 6.95; (dd, J=25.5 Hz, 3.4 Hz, 2H), 3.82; (s, 2H), 3.35-3.32; (m, 2H), 3.01; (d, J=4.8 Hz, 4H), 2.95; (s, 4H), 2.50; (t, J=6.9 Hz, 2H), 1.68-1.64; (m, 2H).

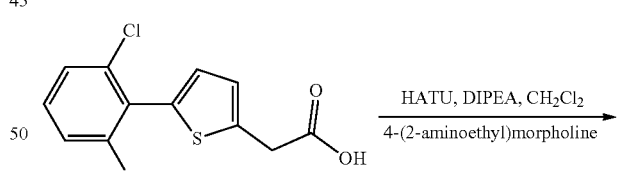

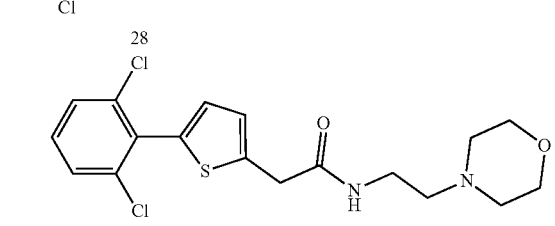

2-(5-(2,6-dichlorophenyl)thiophen-2-yl)-N-(2-morpholinoethyl)acetamide (AB1181): Compound AB1181 (248 mg) was synthesized from compound 28 by following general procedure C. $^1$H NMR(CDCl$_3$, 500 MHz): δ 7.41; (d, J=7.6 Hz, 2H), 7.25; (d, J=9.0 Hz, 1H), 6.98; (d, J=3.4 Hz, 1H), 6.93; (d, 1H), 6.36; (s, 1H), 3.64-3.62; (m, 2H), 3.37; (dd, J=11.7 Hz, 5.5 Hz, 2H), 2.47-2.45; (m, 2H), 2.40; (bs, 4H).

Experimental Data

Compounds as described in the present invention were synthesized and screened for their ability to rescue cells from stress induced death. The results obtained establish the remarkable effect of compounds of the present invention and show a promise towards the utility of these novel compounds in the treatment of ER stress related diseases, more specifically, autoimmune diseases.

Particularly, in-vitro studies were performed on mouse B16F10 and human A375 cells (cells of melanocyte origin) which showed that cells treated with tunicamycin suffered loss of cell viability. When they were treated with compounds of the present invention, cell viability was recovered to significant level, demonstrating the potential of compounds of present invention as efficacious compounds for utilization in treatment of skin autoimmune diseases including Vitiligo.

The table I below mentions the % recovery of cells by the compound at specific dose.

TABLE I

List of Compounds and their potency at 10 µM concentration in mouse B16F10 cells

|  | Compound No | B16F10 % Recovery |
|---|---|---|
| 1. | AB1014 | 32 |
| 2. | AB1045 | 46 |
| 3. | AB1051 | 22 |
| 4. | AB1062 | 21 |
| 5. | AB1078 | 59 |
| 6. | AB1080 | 44 |
| 7. | AB1094 | 48 |
| 8. | AB1097 | 57 |
| 9. | AB1099 | 37 |
| 10 | AB1109 | 26 |
| 11 | AB1110 | 50 |
| 12 | AB1114 | 21 |
| 13 | AB1117 | 21 |
| 14 | AB1118 | 44 |
| 15 | AB1119 | 30 |
| 16 | AB1120 | 23 |
| 17 | AB1151 | 23 |
| 18 | AB1152 | 27 |
| 19 | AB1162 | 71 |
| 20 | AB1164 | 45 |

TABLE II

List of Compounds and their potency at 10 µM concentration in human A375 cells

|  | Compound No | A375 % Recovery |
|---|---|---|
| 1. | AB1090 | 24 |
| 2. | AB1097 | 47 |
| 3. | AB1098 | 28 |
| 4. | AB1099 | 45 |
| 5. | AB1101 | 22 |
| 6. | AB1110 | 23 |
| 7. | AB1114 | 32 |
| 8. | AB1119 | 27 |
| 9. | AB1120 | 30 |
| 10. | AB1151 | 27 |
| 11. | AB1152 | 23 |
| 12. | AB1162 | 58 |
| 13. | AB1163 | 37 |
| 14. | AB1164 | 50 |
| 15. | AB1176 | 25 |
| 16. | AB1177 | 31 |
| 17. | AB1179 | 20 |

Table III and Table IV describe potency of the compounds as effective concentration 50 ($EC_{50}$) which means the dose of compound needed to achieve 50% of maximum effect.

TABLE III

EC50 (µM) of NCEs in mouse B16F10 cells

| Sr No | NCE | B16F10 EC50 (µM) |
|---|---|---|
| 1 | AB1010 | 6.55 |
| 2 | AB1062 | 32.1 |
| 3 | AB1093 | 36.2 |
| 4 | AB1099 | 10.0 |
| 5 | AB1102 | 55.7 |
| 6 | AB1108 | 43.7 |
| 7 | AB1109 | 6.49 |
| 8 | AB1110 | 6.24 |
| 9 | AB1113 | 46.7 |
| 10 | AB1114 | 12.5 |
| 11 | AB1115 | 53.44 |
| 12 | AB1116 | 13.7 |
| 13 | AB1117 | 20.7 |
| 14 | AB1118 | 19.5 |
| 15 | AB1119 | 9.51 |
| 16 | AB1164 | 9.72 |

TABLE IV

EC50 (µM) of NCEs in human A375 cells

| Sr No | NCE | A375 EC50 (µM) |
|---|---|---|
| 1 | AB1010 | 5.22 |
| 2 | AB1062 | 48.5 |
| 3 | AB1093 | 31.22 |
| 4 | AB1099 | 17.3 |
| 5 | AB1102 | 71.1 |
| 6 | AB1108 | 34.2 |
| 7 | AB1109 | 13.9 |
| 8 | AB1110 | 62.7 |
| 9 | AB1113 | 18.3 |
| 10 | AB1114 | 4.26 |
| 11 | AB1117 | 26.7 |
| 12 | AB1118 | 31.6 |
| 13 | AB1119 | 8.47 |
| 14 | AB1151 | 10.6 |
| 15 | AB1152 | 4.86 |
| 16 | AB1162 | 6.02 |
| 17 | AB1163 | 5.15 |
| 18 | AB1164 | 3.70 |

Methods used for Experimental Data: Mouse B16F10 or human A375 cells were seeded (5000 cells per well) in 96-well plates for 24 h. Cells were then treated in quadruplicate with multiple concentrations of compounds for 6 h. The compounds were dissolved in DMSO at 1000× concentration and then diluted to final concentration directly in cell culture medium. The vehicle control (VC) contains equal amount of DMSO. Cells were then treated with tunicamycin (Tm) (300 ng/ml for B16F10 and 100 ng/ml for A375 cells) and after 72 h of treatment, MTT assay was performed. Cell growth in vehicle control was calculated as 100% and effect of the compounds over tunicamycin treatment was calculated accordingly. $EC_{50}$ values were calculated using GraphPad Prism 7 software.

From the data provided in Table I and Table II it can be established that the compounds of the present invention are successful in rescuing cells from stress induced cell death.

Table I and Table-II clearly reflects the effectiveness of the compounds of the present invention in recovering cell viability in mouse B16F10 and human A375 cells.

Table III and Table-IV enunciates data reflecting the $EC_{50}$ of compounds of the present invention to achieve desired effect of recovery of cell viability.

Compounds of the present invention are therefore novel compounds that are potentially useful in applications related to the treatment and prevention of ER stress related diseases.

We claim:
1. A compound of Formula I represented by

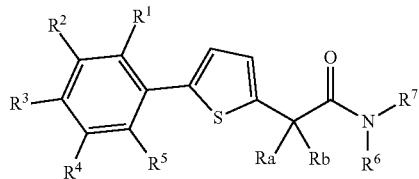

Formula I wherein
R1, R2, R3, R4, R5 are each independently selected from hydrogen, halogen, phenyl, straight chain or branched C1-C5 alkyl, straight chain or branched C2-C5 alkenyl, straight chain or branched C1-C5 alkoxyalkyl, straight chain or branched C1-C5 alkoxyaryl, aryl, CF3, C3-C7 aromatic or aliphatic heterocycle comprising at least one hetero atom selected from a group of O, N and S; or any of two adjacent R groups R1, R2, R3, R4, and R5 may together form (1) a naphthalene; or (2) a 5-6 membered aromatic or aliphatic ring comprising at least one hetero atom selected from a group of O, N and S;

Ra and Rb are each independently selected from hydrogen, straight chain or branched C1-C5 alkyl, straight chain or branched C1-C5 aralkyl, straight chain or branched C2-C5 alkenyl, straight chain or branched C2-C5 alkynyl, or both Ra, and Rb together form a 3-7 membered ring comprising at least one hetero atom selected from a group of O, N and S;

R6 and R7 are each independently selected from hydrogen, unsubstituted straight chain or branched C1-C5 alkyl, straight chain or branched C1-C5 aralkyl, straight chain or branched C2-C5 alkenyl, straight chain or branched C2-C5 alkynyl; or
—CH2(CH2)nNRcRd wherein n is 0-3, and Rc and Rd are both CH3 or together form a 3-7 membered aromatic or aliphatic heterocycle comprising at least one hetero atom selected from a group of O, N and S; or
both R6 and R7 may together form a 3-7 membered aliphatic heterocycle comprising at least one hetero atom selected from O, N and S;

provided that R6 and R7 are not both hydrogen;

or a stereoisomer; a racemic mixture; a geometrical isomer; a tautomer; a pharmaceutically acceptable salt, hydrate, or solvate; a solid form; or a mixture of solid forms thereof.

2. The compound of Formula I as claimed in claim 1, wherein $R^1$, $R^2$, $R^3$, $R^4$, and $R^5$ are each independently selected from a group consisting of F, Cl, Br and I.

3. The compound of Formula I as claimed in claim 1, wherein at least one of the substituents selected from R1, R2, R3, R4, and R5 is a phenyl group optionally substituted by straight chain or branched C1-C5 alkyl, or straight chain or branched C1-C5 alkoxyalkyl.

4. The compound of Formula I as claimed in claim 1, wherein at least one of the substituents selected from R1, R2, R3, R4, and R5 is a C3-C7 aromatic or aliphatic heterocycle comprising at least one hetero atom selected from a group of O, N and S, wherein it is optionally substituted with C1-C5 alkyl, C2-C5 alkenyl or C1-C5 alkoxyalkyl.

5. The compound of Formula I as claimed in claim 1, wherein R6 and R7, together form a 3-7 membered aliphatic heterocycle comprising at least one hetero atom selected from O, N and S, further wherein the heterocycle is optionally substituted with a substituent selected from the group consisting of halogen, CF3, straight chain or branched C1-C5 alkyl, straight chain or branched C2-C5 alkenyl, and straight chain or branched C1-C5 alkoxyalkyl.

6. The compound of Formula I as claimed in claim 1, wherein any two adjacent substituents selected from R1, R2, R3, R4 and R5, combine to form naphthalene.

7. The compound of Formula I as claimed in claim 1 wherein Rc, and Rd form a 3-7 membered aromatic or aliphatic heterocycle comprising at least one hetero atom selected from O, N and S, further wherein the heterocycle is optionally substituted with any substituent selected from the group of halogen, CF3, straight chain or branched C1-C5 alkyl, straight chain or branched C2-C5 alkenyl, and straight chain or branched C1-C5 alkoxyalkyl.

8. The compound of Formula I as claimed in claim 1, wherein Rc, and Rd together form a heterocycle dioxidothiomorpholine.

9. A compound selected from:
N-butyl-2-(5-(4-chlorophenyl)thiophen-2-yl)acetamide,
2-(5-(4-chlorophenyl)thiophen-2-yl)-N-(3-isopropoxypropyl)acetamide,
2-(5-(4-chlorophenyl)thiophen-2-yl)-1-(pyrrolidin-1-yl)ethan-1-one,
2-(5-(4-chlorophenyl)thiophen-2-yl)-1-(4-methylpiperazin-1-yl)ethan-1-one,
2-(5-(4-chlorophenyl)thiophen-2-yl)-N-(4-fluorophenethyl)acetamide,
2-(5-(4-chlorophenyl)thiophen-2-yl)-N-(2-(pyrrolidin-1-yl)ethyl)acetamide,
2-(5-(4-chlorophenyl)thiophen-2-yl)-1-(3,5-dimethylmorpholino)ethan-1-one,
2-(5-(4-chlorophenyl)thiophen-2-yl)-N-cyclopentylacetamide,
2-(5-(4-chlorophenyl)thiophen-2-yl)-N-(4-fluorophenyl)acetamide,
2-(5-(4-chlorophenyl)thiophen-2-yl)-N-(3-(trifluoromethyl)phenyl)acetamide,
2-(5-(4-chlorophenyl)thiophen-2-yl)-N-(3,5-difluorobenzyl)acetamide,
N-(3-(1H-imidazol-1-yl)propyl)-2-(5-(4-chlorophenyl)thiophen-2-yl)acetamide,
2-(5-(4-Chlorophenyl)thiophen-2-yl)-N-(2-(piperidin-1-yl)ethyl)acetamide, 2-(5-(4-Chlorophenyl)thiophen-2-yl)-N-(2-(dimethylamino)ethyl)acetamide,
2-(5-(4-chlorophenyl)thiophen-2-yl)-N-(2-morpholinoethyl)acetamide hydrochloride,
2-(5-(4-chlorophenyl)thiophen-2-yl)-2-methyl-1-(4-methylpiperazin-1-yl)propan-1-one,
2-(5-(4-chlorophenyl)thiophen-2-yl)-2-methyl-N-(2-(piperidin-1-yl)ethyl)propanamide,
N-(3-(1H-imidazol-1-yl)propyl)-2-(5-(4-chlorophenyl)thiophen-2-yl)-2-methylpropanamide,
2-(5-(4-chlorophenyl)thiophen-2-yl)-1-(4,4-difluoropiperidin-1-yl)ethan-1-one,
2-(5-(4-fluorophenyl)thiophen-2-yl)-1-(4-methylpiperazin-1-yl)ethan-1-one,
N-(4-fluorophenethyl)-2-(5-(4-fluorophenyl)thiophen-2-yl)acetamide,
2-(5-(4-fluorophenyl)thiophen-2-yl)-N-(2-morpholinoethyl)acetamide,
2-(5-(4-fluorophenyl)thiophen-2-yl)-N-(2-(piperidin-1-yl)ethyl)acetamide,
N-(3-(1H-imidazol-1-yl)propyl)-2-(5-(4-fluorophenyl)thiophen-2-yl)acetamide,
2-(5-(2,4-dichlorophenyl)thiophen-2-yl)-1-(4-methylpiperazin-1-yl)ethan-1-one,
2-(5-(2,4-dichlorophenyl)thiophen-2-yl)-N-(4-fluorophenethyl)acetamide,
2-(5-(2,4-dichlorophenyl)thiophen-2-yl)-N-(2-morpholinoethyl)acetamide,
1-(4-methylpiperazin-1-yl)-2-(5-phenylthiophen-2-yl)ethan-1-one,
N-(4-fluorophenethyl)-2-(5-phenylthiophen-2-yl)acetamide,
N-(2-morpholinoethyl)-2-(5-phenylthiophen-2-yl)acetamide,
2-(5-(2,4-dichlorophenyl)thiophen-2-yl)-N-(2-(piperidin-1-yl)ethyl)acetamide,
2-(5-phenylthiophen-2-yl)-N-(2-(piperidin-1-yl)ethyl)acetamide,
N-(3-(1H-imidazol-1-yl)propyl)-2-(5-phenylthiophen-2-yl)acetamide,
N-(3-(1H-imidazol-1-yl)propyl)-2-(5-(2,4-dichlorophenyl)thiophen-2-yl)acetamide,
2-(5-(3-fluorophenyl)thiophen-2-yl)-1-(4-methylpiperazin-1-yl)ethan-1-one,
2-(5-(3-fluorophenyl)thiophen-2-yl)-N-(2-morpholinoethyl)acetamide,
2-(5-(2,4-dichlorophenyl)thiophen-2-yl)-N-(2-(1,1-dioxidothiomorpholino)ethyl)acetamide,
2-(5-(2,4-dichlorophenyl)thiophen-2-yl)-N-(2-(4-methylpiperazin-1-yl)ethyl)acetamide,
2-(5-(3-chlorophenyl)thiophen-2-yl)-1-(4-methylpiperazin-1-yl)ethan-1-one,
2-(5-(3-chlorophenyl)thiophen-2-yl)-N-(2-morpholinoethyl)acetamide,
2-(5-(3,5-dichlorophenyl)thiophen-2-yl)-N-(2-morpholinoethyl)acetamide,
2-(5-(4-methoxyphenyl)thiophen-2-yl)-N-(2-morpholinoethyl)acetamide,
N-(2-morpholinoethyl)-2-(5-(4-(trifluoromethyl)phenyl)thiophen-2-yl)acetamide,
2-(5-(3-(3,5-dimethyl-1H-pyrazol-1-yl)phenyl)thiophen-2-yl)-N-(2-morpholinoethyl)acetamide,
2-(5-(4-chlorophenyl)thiophen-2-yl)-N-(3-morpholinopropyl)acetamide,
2-(5-(2,4-dichlorophenyl)thiophen-2-yl)-N-(3-(1,1-dioxidothiomorpholino)propyl)acetamide,
2-(5-(3-bromophenyl)thiophen-2-yl)-N-(2-morpholinoethyl)acetamide,
N-(2-morpholinoethyl)-2-(5-(3-morpholinophenyl)thiophen-2-yl)acetamide,
2-(5-(3-(1-methyl-1H-pyrazol-4-yl)phenyl)thiophen-2-yl)-N-(2-morpholinoethyl)acetamide,
2-(5-(3-(1-methyl-1H-pyrrol-2-yl)phenyl)thiophen-2-yl)-N-(2-morpholinoethyl)acetamide,
N-(2-morpholinoethyl)-2-(5-(3-(pyrazin-2-yl)phenyl)thiophen-2-yl)acetamide,
2-(5-(4-chlorophenyl)thiophen-2-yl)-1-morpholinoethan-1-one,
2-(5-(4-chlorophenyl)thiophen-2-yl)-1-thiomorpholinoethan-1-one,
2-(5-(3-(1-methyl-1H-imidazol-4-yl)phenyl)thiophen-2-yl)-N-(2-morpholinoethyl)acetamide,
2-(5-(3,5-dichlorophenyl)thiophen-2-yl)-N-(3-morpholinopropyl)acetamide,
2-(5-(3,5-dichlorophenyl)thiophen-2-yl)-N-(2-(1,1-dioxidothiomorpholino)ethyl)acetamide,
2-(5-(3,5-dichlorophenyl)thiophen-2-yl)-N-(3-(1,1-dioxidothiomorpholino)propyl)acetamide,
2-(5-(3,5-dichlorophenyl)thiophen-2-yl)-1-morpholinoethan-1-one,
2-(5-(3,5-dichlorophenyl)thiophen-2-yl)-1-thiomorpholinoethan-1-one,
2-(5-(3,5-dichlorophenyl)thiophen-2-yl)-1-(4-(4-fluorophenyl)piperidin-1-yl)ethan-1-one,
2-(5-(2,4-dichlorophenyl)thiophen-2-yl)-N-morpholinoacetamide,
2-(5-(2,6-dichlorophenyl)thiophen-2-yl)-N-(3-(1,1-dioxidothiomorpholino)propyl) acetamide,
2-(5-(2,6-dichlorophenyl)thiophen-2-yl)-N-(2-morpholinoethyl)acetamide,
2-(5-(2,4-dichlorophenyl)thiophen-2-yl)-N-(piperidin-1-yl)acetamide,
(1-(5-(4-chlorophenyl)thiophen-2-yl)cyclopropyl)(4-methylpiperazin-1-yl)methanone
(1-(5-(4-chlorophenyl)thiophen-2-yl)cyclobutyl)(4-methylpiperazin-1-yl)methanone,
(3-(5-(4-chlorophenyl)thiophen-2-yl)oxetan-3-yl)(4-methylpiperazin-1-yl)methanone,
(1-(5-(4-fluorophenyl)thiophen-2-yl)cyclopropyl)(4-methylpiperazin-1-yl)methanone,
(1-(5-(4-fluorophenyl)thiophen-2-yl)cyclobutyl)(4-methylpiperazin-1-yl)methanone,
(3-(5-(4-fluorophenyl)thiophen-2-yl)oxetan-3-yl)(4-methylpiperazin-1-yl)methanone,
N-butyl-2-(5-(naphthalen-1-yl)thiophen-2-yl)acetamide and
2-(5-(3,5-dichlorophenyl)thiophen-2-yl)-N-morpholinoacetamide;
or a stereoisomer; a racemic mixture; a geometrical isomer; a tautomer; a pharmaceutically acceptable salt, hydrate, or solvate; a solid form; or a mixture of solid forms thereof.

10. A process for the preparation of the compound of Formula I as claimed in claim 1, comprising the steps of:
a) Stirring thiophene acetonitrile in the presence of catalyst N-bromosuccinamide (NBS) in a solvent selected from a group consisting of dimethylformamide (DMF), dimethylsulfoxide (DMSO) and Tetrahydrofuran (THF) to obtain a bromo thiophene acetonitrile;
b) Reacting the bromo thiophene acetonitrile obtained from Step a, with substituted phenylboronic acid in the presence of a solvent selected from toluene, benzene, dimethyl formamide, dioxane, and tertiary butanol;

potassium carbonate; and triphenylphosphine palladium(0) or a Palladium (0) catalyst at a temperature of about 80° C.-100° C. for about 6-24 hours to obtain a compound of Formula II:

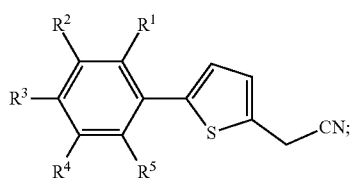

c Refluxing the compound of Formula II after stirring it in ethanol and aqueous sodium hydroxide to obtain a compound of Formula III:

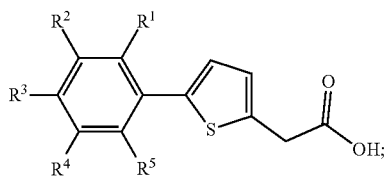

d) Coupling of the compound of Formula III with an amine, in the presence of a base selected from Hunigs base (N,N, Diisopropylethylamine), triethylamine, pyrrolidine, and piperidine; and an amide coupling reagent selected from a group consisting of HATU, HBTU, EDC, EDC-HOBt, EDC-DMAP, DCC, DCC-DMAP, DCC-HOBt, DIC, TBTU, and T3P added at 0° C. to obtain the compound of Formula I:

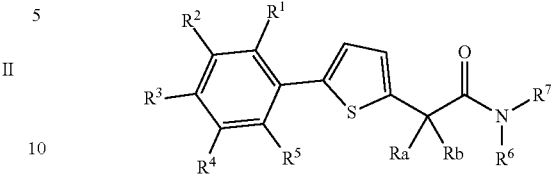

and e) Optionally purifying the compound of Formula I by column chromatography.

11. A pharmaceutical composition comprising an effective amount of one or more of the compounds as claimed in claim 1, or their stereoisomers, racemic mixtures, geometrical isomers, tautomers, pharmaceutically acceptable salts, hydrates, solvates, solid forms or mixtures thereof, as an active ingredient along with a pharmaceutically acceptable carrier.

12. A process for preparing a pharmaceutical composition as claimed in claim 11, comprising the step of mixing at least one of the compounds of Formula I with a pharmaceutically acceptable carrier.

13. The pharmaceutical composition as claimed in claim 11, wherein the composition is in the form of a formulation that is administered in unit-dosage forms selected from tablets, capsules, pills, powders, granules, sterile parenteral solutions or suspensions, oral solutions or suspensions, injections, syrup, liquid, microemulsion, topical creams, ointments, suppositories, sachets, troches and lozenges and oil-water emulsions containing suitable quantities of the compound of Formula I or multiple-dosage forms.

* * * * *